(12) United States Patent
Fyfe et al.

(10) Patent No.: US 8,207,147 B2
(45) Date of Patent: Jun. 26, 2012

(54) HETEROCYCLIC DERIVATIVES AS GPCR RECEPTOR AGONISTS

(75) Inventors: Matthew Colin Thor Fyfe, Oxford (GB); Lisa Sarah Gardner, Oxford (GB); John King-Underwood, Oxford (GB); Martin James Procter, Oxford (GB); Chrystelle Marie Rasamison, Oxford (GB); Karen Lesley Schofield, Oxford (GB); Gerard Hugh Thomas, Oxford (GB)

(73) Assignee: Prosidion Limited, Oxford (GB)

( * ) Notice: Subject to any disclaimer, the term of this patent is extended or adjusted under 35 U.S.C. 154(b) by 949 days.

(21) Appl. No.: 10/584,025

(22) PCT Filed: Dec. 23, 2004

(86) PCT No.: PCT/GB2004/050046
§ 371 (c)(1),
(2), (4) Date: Aug. 26, 2008

(87) PCT Pub. No.: WO2005/061489
PCT Pub. Date: Jul. 7, 2005

(65) Prior Publication Data
US 2009/0281060 A1    Nov. 12, 2009

Related U.S. Application Data

(60) Provisional application No. 60/532,370, filed on Feb. 24, 2003.

(51) Int. Cl.
*A61K 31/66* (2006.01)
*A61K 31/497* (2006.01)
*A61K 31/4523* (2006.01)
*C07D 401/14* (2006.01)
*C07F 9/02* (2006.01)
*C07D 211/00* (2006.01)
*C07D 413/14* (2006.01)

(52) U.S. Cl. ............ 514/89; 514/255.05; 514/318; 514/326; 544/405; 546/21; 546/193; 546/269.4

(58) Field of Classification Search .............. 514/89, 514/255.05, 318, 326; 544/405; 546/21, 546/193, 269.4
See application file for complete search history.

(56) References Cited

U.S. PATENT DOCUMENTS

| 3,647,809 A | * | 3/1972 | Reiter ............... 546/256 |
| 6,239,160 B1 | | 5/2001 | Tiebes et al. |
| 2003/0162812 A1 | | 8/2003 | Harmsen et al. |

FOREIGN PATENT DOCUMENTS

| CN | 1379775 A | 11/2002 |
| WO | WO-9746556 A1 | 12/1997 |
| WO | WO-9817652 A1 | 4/1998 |
| WO | WO-0024735 A1 | 5/2000 |
| WO | WO-0035913 A1 | 6/2000 |
| WO | WO-0108685 A1 | 2/2001 |
| WO | WO-0112627 A1 | 2/2001 |
| WO | WO 02/12229 * | 2/2002 |
| WO | WO-02068417 A2 | 9/2002 |
| WO | WO-2004026305 A1 | 4/2004 |
| WO | WO-2004060362 A2 | 7/2004 |

OTHER PUBLICATIONS

Overton, H.A. et al., "Deorphanization of a G-protein-coupled receptor for oleoylethanolamide and its use in the discovery of small-molecule hypophagic agents," *Cell Metabolism* 3, 167-175, Mar. 2006.

Overton, H.A. et al., "GPR119, a novel G protein-coupled receptor target for the treatment of type 2 diabetes and obesity," *British Journal of Pharmacology* (2008) 153, 576-581.

Williams, J.P. and Lavrador, K., "A Solution-Phase Combinatorial Synthesis of Selective Dopamine $D_4$ Ligands," *Combinatorial Chemistry & High Throughput Screening*, 2000, 3, 43-50.

* cited by examiner

*Primary Examiner* — Joseph Kosack
*Assistant Examiner* — Samantha Shterengarts
(74) *Attorney, Agent, or Firm* — Mintz Levin Cohn Ferris Glovsky and Popeo, P.C.; Ivor R. Elrifi; Heidi A. Erlacher

(57) ABSTRACT

Compounds of Formula (I), $R^1$-A-V—B—$R^2$; or pharmaceutically acceptable salts thereof, are agonists of GPR116 and are useful as regulators of satiety, e.g. for the treatment of obesity, and for the treatment of diabetes.

11 Claims, No Drawings

US 8,207,147 B2

HETEROCYCLIC DERIVATIVES AS GPCR RECEPTOR AGONISTS

RELATED APPLICATION

This application is a national stage application, filed under 35 U.S.C. §371, of International Application PCT/GB2004/050046 filed Dec. 23, 2004, which claims the benefit of and priority to U.S. Provisional Patent Application Ser. No. 60/532,370 filed Feb. 24, 2003 the disclosure of each is incorporated by reference herein.

BACKGROUND OF THE INVENTION

The present invention is directed to G-protein coupled receptor (GPCR) agonists. In particular, the present invention is directed to agonists of GPR116 that are useful as regulators of satiety, e.g. for the treatment of obesity, and for the treatment of diabetes.

Obesity is characterized by an excessive adipose tissue mass relative to body size. Clinically, body fat mass is estimated by the body mass index (BMI; weight(kg)/height(m)$^2$), or waist circumference. Individuals are considered obese when the BMI is greater than 30 and there are established medical consequences of being overweight. It has been an accepted medical view for some time that an increased body weight, especially as a result of abdominal body fat, is associated with an increased risk for diabetes, hypertension, heart disease, and numerous other health complications, such as arthritis, stroke, gallbladder disease, muscular and respiratory problems, back pain and even certain cancers.

Pharmacological approaches to the treatment of obesity have been mainly concerned with reducing fat mass by altering the balance between energy intake and expenditure. Many studies have clearly established the link between adiposity and the brain circuitry involved in the regulation of energy homeostasis. Direct and indirect evidence suggest that serotonergic, dopaminergic, adrenergic, cholinergic, endocannabinoid, opioid, and histaminergic pathways in addition to many neuropeptide pathways (e.g. neuropeptide Y and melanocortins) are implicated in the central control of energy intake and expenditure. Hypothalamic centres are also able to sense peripheral hormones involved in the maintenance of body weight and degree of adiposity, such as insulin and leptin, and fat tissue derived peptides.

Drugs aimed at the pathophysiology associated with insulin dependent Type I diabetes and non-insulin dependent Type II diabetes have many potential side effects and do not adequately address the dyslipidaemia and hyperglycaemia in a high proportion of patients. Treatment is often focused at individual patient needs using diet, exercise, hypoglycaemic agents and insulin, but there is a continuing need for novel antidiabetic agents, particularly ones that may be better tolerated with fewer adverse effects.

Similarly, metabolic syndrome (syndrome X) which is characterized by hypertension and its associated pathologies including atherosclerosis, lipidemia, hyperlipidemia and hypercholesterolemia have been associated with decreased insulin sensitivity which can lead to abnormal blood sugar levels when challenged. Myocardial ischemia and microvascular disease is an established morbidity associated with untreated or poorly controlled metabolic syndrome.

There is a continuing need for novel antiobesity and antidiabetic agents, particularly ones that are well tolerated with few adverse effects.

GPR116 is a GPCR identified as SNORF25 in WO00/50562 which discloses both the human and rat receptors, U.S. Pat. No. 6,468,756 also discloses the mouse receptor (accession numbers: AAN95194 (human), AAN95195 (rat) and ANN95196 (mouse)).

In humans, GPR116 is expressed in the pancreas, small intestine, colon and adipose tissue. The expression profile of the human GPR116 receptor indicates its potential utility as a target for the treatment of obesity and diabetes.

Williams J. P., Combinatorial Chemistry & High Throughput Screening, 2000, 3, 43-50 discloses the compounds 4-(5-piperidin-4-yl-[1,2,4]oxadiazol-3-yl)pyridine and 4-(3-pyridin-4-yl-[1,2,4]oxadiazol-5-yl)piperidine-1-carboxylic acid $^t$butyl ester, synthesised as part of a compound library designed to identify dopamine $D_4$ ligands.

The compounds 4-[5-(4-butylcyclohexyl)-[1,2,4]oxadiazol-3-yl]pyridine and 3-[5-(4-propylcyclohexyl)-[1,2,4]oxadiazol-3-yl]pyridine (Chem Div) and 3-[5-(4-butylcyclohexyl)-[1,2,4]oxadiazol-3-yl]pyridine (Chembridge) are/were commercially available. No pharmaceutical utility has been suggested for these compounds.

The present invention relates to agonists of GPR116 which are useful as peripheral regulators of satiety, e.g. for the treatment of obesity, and for the treatment of diabetes.

SUMMARY OF THE INVENTION

Compounds of formula (I):

$$R^1\text{-A-V}—B—R^2 \tag{I}$$

or pharmaceutically acceptable salts thereof are agonists of GPR116 and are useful as regulators of satiety, e.g. in the prophylactic or therapeutic treatment of obesity, and for the treatment of diabetes.

DETAILED DESCRIPTION OF THE INVENTION

The present invention is directed to a compound of formula (I), or a pharmaceutically acceptable salt thereof:

$$R^1\text{-A-V}—B—R^2 \tag{I}$$

wherein V is a 5-membered heteroaryl ring containing up to four heteroatoms selected from O, N and S, optionally substituted by $C_{1-4}$ alkyl;

A is —CH=CH— or $(CH_2)_n$;

B is —CH=CH— or $(CH_2)_n$, where one of the $CH_2$ groups may be replaced by O, $NR^5$, $S(O)_m$, $C(O)$ or $C(O)NR^{12}$;

n is independently 0, 1, 2 or 3;

m is independently 0, 1 or 2;

$R^1$ is 3- or 4-pyridyl, 4- or 5-pyrimidinyl or 2-pyrazinyl, any of which may be optionally substituted by one or more substituents selected from halo, $C_{1-4}$ alkyl, $C_{1-4}$ fluoroalkyl, $C_{2-4}$ alkenyl, $C_{2-4}$ alynyl, $C_{3-7}$ cycloalkyl, aryl, $OR^6$, CN, $NO_2$, $S(O)_mR^6$, $CON(R^6)_2$, $N(R^6)_2$, $NR^{10}COR^6$, $NR^{10}SO_2R^6$, $SO_2N(R^6)_2$, a 4- to 7-membered heterocyclyl group or a 5- or 6-membered heteroaryl group;

$R^2$ is 4- to 7-membered cycloalkyl substituted by $R^3$, C(O)$OR^3$, C(O)$R^3$ or S(O)$_2R^3$, or 4 to 7-membered heterocyclyl, containing one or two nitrogen atoms which is unsubstituted or substituted by C(O)$OR^4$, C(O)$R^3$, S(O)$_2R^3$, C(O)NHR$^4$, P(O)(OR$^{11}$)$_2$ or a 5- or 6-membered nitrogen containing heteroaryl group;

$R^3$ is $C_{3-8}$ alkyl, $C_{3-8}$ alkenyl or $C_{3-8}$ alkynyl, any of which may be optionally substituted with up to 5 fluoro or chloro atoms, and may contain a $CH_2$ group that may be replaced by O, or $C_{3-7}$ cycloalkyl, aryl, heterocyclyl, heteroaryl, $C_{1-4}$ alkyl$C_{3-7}$ cycloalkyl, $C_{1-4}$ alkylaryl, $C_{1-4}$ alkylheterocyclyl or $C_{1-4}$ alkylheteroaryl, any of which may be optionally substituted with one or more substituents selected from halo, $C_{1-4}$ alkyl, $C_{1-4}$ fluoroalkyl, $OR^6$, CN, $CO_2C_{1-4}$ alkyl, $N(R^6)_2$ and $NO_2$;

$R^4$ is $C_{2-8}$ alkyl, $C_{2-8}$ alkenyl or $C_{2-8}$ alkynyl, any of which may be optionally substituted with up to 5 fluoro or chloro atoms, and may contain a $CH_2$ group that may be replaced by O, or $C_{3-7}$ cycloalkyl, aryl, heterocyclyl, heteroaryl, $C_{1-4}$ alkyl$C_{3-7}$ cycloalkyl, $C_{1-4}$ alkylaryl, $C_{1-4}$ alkylheterocyclyl or $C_{1-4}$ alkylheteroaryl, any of which may be substituted with one or more substituents selected from halo, $C_{1-4}$ alkyl, $C_{1-4}$ fluoroalkyl, $OR^6$, CN, $CO_2C_{1-4}$ alkyl, $N(R^6)_2$ and $NO_2$;

$R^5$ is hydrogen, $C(O)R^7$, $S(O)_2R^8$, $C_{3-7}$ cycloalkyl or $C_{1-4}$ alkyl optionally substituted by $OR^6$, $C_{3-7}$ cycloalkyl, aryl, heterocyclyl or heteroaryl, wherein the cyclic groups may be substituted with one or more substituents selected from halo, $C_{1-2}$ alkyl, $C_{1-2}$ fluoroalkyl, $OR^6$, CN, $N(R^6)_2$ and $NO_2$;

$R^6$ are independently hydrogen, $C_{1-4}$ alkyl, $C_{3-7}$ cycloalkyl, aryl, heterocyclyl or heteroaryl, wherein the cyclic groups may be substituted with one or more substituents selected from halo, $C_{1-4}$ alkyl, $C_{1-4}$ fluoroalkyl, $OR^9$, CN, $SO_2CH_3$, $N(R^{10})_2$ and $NO_2$; or a group $N(R^{10})_2$ may form a 4- to 7-membered heterocyclic ring optionally containing a further heteroatom selected from O and $NR^{10}$;

$R^7$ is hydrogen, $C_{1-4}$ alkyl, $OR^6$, $N(R^6)_2$, aryl or heteroaryl;
$R^8$ is $C_{1-4}$ alkyl, $C_{1-4}$ fluoroalkyl, aryl or heteroaryl;
$R^9$ is hydrogen, $C_{1-2}$ alkyl or $C_{1-2}$ fluoroalkyl;
$R^{10}$ is hydrogen or $C_{1-4}$ alkyl;
$R^{11}$ is phenyl; and
$R^{12}$ is hydrogen, $C_{1-4}$ alkyl or $C_{3-7}$ cycloalkyl;
provided that the compound is not:
a) 4-(5-piperidin-yl-[1,2,4]oxadiazol-3-yl)pyridine;
b) 4-(3-pyridin-4-yl-[1,2,4]oxadiazol-5-yl)piperidine-1-carboxylic acid ′butyl ester;
c) 4-[5-(4-butylcyclohexyl)-[1,2,4]oxadiazol-3-yl]pyridine;
d) 3-[5-(4-butylcyclohexyl)-[1,2,4]oxadiazol-3-yl]pyridine; or
e) 3-[5-(4-propylcyclohexyl)-[1,2,4]oxadiazol-3-yl]pyridine.

The molecular weight of the compounds of formula (I) is preferably less than 800, more preferably less than 600, especially less than 500.

In the compounds of formula (I) V is preferably a 5-membered heteroaryl ring containing up to three heteroatoms selected from O, N and S of the formula:

wherein W, X and Y represent the positions of the heteroatom(s) or otherwise represent CH.

Particular heterocyclic rings which V may represent include oxadiazole, oxazole, isoxazole, thiadiazole, thiazole and pyrazole.

Preferably two of W, X and Y are N, and the other is O.
W is preferably N.
Preferably the n groups of A and B do not both represent 0.
In A, n is preferably 0, 1 or 2, more preferably 0.
In B, n is preferably 2 or 3, more preferably 2.
When one of the $CH_2$ groups in B is replaced, it is preferably replaced by O, $NR^5$, $S(O)_m$ or C(O); more preferably it is replaced by O or $NR^5$.

$R^1$ is preferably 4-pyridyl optionally substituted by 1 or 2 halo, $C_{1-4}$ alkyl, $C_{1-4}$ fluoroalkyl, $C_{2-4}$ alkenyl, $C_{2-4}$ alynyl, $C_{3-4}$ cycloalkyl, aryl, $OR^6$, CN, $NO_2$, $S(O)_mR^6$, $CON(R^6)_2$, $N(R^6)_2$, $NR^{10}COR^6$, $NR^{10}SO_2^6$, $SO_2N(R^6)$, 4- to 7-membered heterocyclyl or 5- or 6-membered heteroaryl groups; more preferably 4-pyridyl optionally substituted by halo, $C_{1-4}$ alkyl $C_{1-4}$ alkoxy or CN; even more preferably 4-pyridyl, optionally substituted by halo, $C_{1-4}$ alkyl or CN; and especially 4-pyridyl, optionally substituted by CN.

When $R^2$ is a 4- to 7-membered heterocyclyl, containing one or two nitrogen atoms it is preferably substituted, the substitution is preferably on the nitrogen atom $R^2$ is preferably a 4- to 7-membered cycloalkyl substituted by $R^3$ or $C(O)OR^3$, especially $R^3$, or 4- to 7-membered heterocyclyl containing one nitrogen atom which is substituted by $C(O)OR^4$ or a 6-membered nitrogen containing heteroaryl group, more preferably a 4- to 7-membered heterocyclyl containing one nitrogen atom which is substituted by $C(O)OR^4$.

A particularly preferred $R^2$ group is piperidinyl, especially 4-piperidinyl, which is substituted on the nitrogen atom by $C(O)OR^4$.

$R^3$ is preferably $C_{3-8}$ alkyl which may contain a $CH_2$ group that may be replaced by O, or $C_{3-7}$ cycloalkyl, more preferably $R^3$ is $C_{3-8}$ alkyl.

$R^4$ is preferably $C_{2-8}$ alkyl, $C_{2-8}$ alkenyl or $C_{2-8}$ alkynyl, any of which may be optionally substituted with up to 5 fluoro or chloro atoms, and may contain a $CH_2$ group that may be replaced by O, or $C_{3-7}$ cycloalkyl, aryl, 5- to 6-membered heteroaryl containing one or two nitrogen atoms, $C_{1-4}$ alkyl$C_{3-7}$ cycloalkyl or $C_{1-4}$ alkylaryl, any of which may be substituted with one or more substituents selected from halo, $C_{1-4}$ alkyl, $C_{1-4}$ fluoroalkyl, $OR^6$ and $CO_2C_{1-4}$ alkyl.

More preferably $R^4$ is $C_{3-6}$ alkyl optionally substituted with up to 5 fluoro or chloro atoms, e.g. 3 fluoro or chloro atoms, and which may contain a $CH_2$ group that may be replaced by O, or $C_{3-7}$ cycloalkyl.

$R^5$ is preferably hydrogen or $C_{1-4}$ alkyl, more preferably $C_{1-4}$ alkyl.

$R^6$ is preferably hydrogen, $C_{1-4}$ alkyl or $C_{3-7}$ cycloalkyl, more preferably $C_{1-4}$ alkyl.

$R^7$ is preferably hydrogen or $C_{1-4}$ alkyl.

$R^8$ is preferably $C_{1-4}$ alkyl or $C_{1-4}$ fluoroalkyl.

While the preferred groups for each variable have generally been listed above separately for each variable, preferred compounds of this invention include those in which several or each variable in formula (I) is selected from the preferred, more preferred or particularly listed groups for each variable. Therefore, this invention is intended to include all combinations of preferred, more preferred and particularly listed groups. The preferences listed above also apply, where applicable, to the compounds of formula (Ia) to (Ie) below.

A particular group of compounds which may be mentioned are the compounds of formula (Ia) and pharmaceutically acceptable salts thereof:

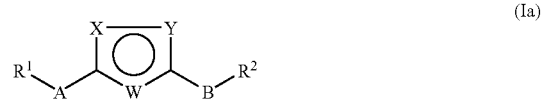

(Ia)

where two of W, X and Y are N, and the other is O;
A is —CH=CH— or $(CH_2)_n$;
B is —CH=CH— or $(CH_2)_n$, where one of the $CH_2$ groups may be replaced by O, $NR^5$, $S(O)_m$, C(O) or $C(O)NR^{12}$;
n is independently 0, 1, 2 or 3;
m is 0, 1 or 2;
$R^1$ is 3- or 4-pyridyl, 4-pyrimidinyl or 2-pyrazinyl, any of which may be optionally substituted by one or more substituents selected from halo, $C_{1-4}$ alkyl, $C_{1-4}$ fluoroalkyl, $C_{3-7}$ cycloalkyl, $OR^{6a}$, CN, $NO_2$, $S(O)_m R^{6b}$, $N(R^6)_2$, $CON(R^{6b})_2$ or a 5- or 6-membered heteroaryl group;

$R^2$ is 4- to 7-membered cycloalkyl substituted by $R^3$, C(O)$OR^3$, $C(O)R^3$ or $S(O)_2 R^3$, or 4- to 7-membered heterocyclyl, containing one or two nitrogen atoms, which is unsubstituted or substituted by C(O)$OR^4$, $C(O)R^3$, $S(O)_2 R^3$, C(O)$NHR^4$, $P(O)(OR^{11})_2$ or a 5- or 6-membered nitrogen containing heteroaryl group;

$R^3$ is $C_{3-8}$ alkyl, $C_{3-8}$ alkenyl or $C_{3-8}$ alkynyl, any of which may be optionally substituted with up to 5 chloro or fluoro atoms, and which may also contain a $CH_2$ group that may be replaced by O, or $C_{3-7}$ cycloalkyl $C_{1-4}$ alkyl$C_{3-7}$ cycloalkyl, aryl or $C_{1-4}$ alkylaryl, wherein the cycloalkyl groups may be optionally substituted by one or more substituents selected from halo and $C_{1-4}$ alkyl, and the aryl groups may be substituted with one or more substituents selected from halo, $C_{1-4}$ alkyl, $C_{1-4}$ fluoroalkyl, $OR^{6a}$, $COOR^{6a}$, CN, $N(R^{6b})_2$ and $NO_2$;

$R^4$ is $C_{2-8}$ alkyl, $C_{2-8}$ alkenyl or $C_{2-8}$ alkynyl, any of which may be optionally substituted with up to 5 chloro or fluoro atoms, and which may also contain a $CH_2$ group that may be replaced by O, or $C_{3-7}$ cycloalkyl, $C_{1-4}$ alkyl$C_{3-7}$ cycloalkyl, aryl or $C_{1-4}$ alkylaryl, wherein the cycloalkyl groups may be optionally substituted by one or more substituents selected from halo and $C_{1-4}$ alkyl, and the aryl groups may be substituted with one or more substituents selected from halo, $C_{1-4}$ alkyl, $C_{1-4}$ fluoroalkyl, $OR^{6a}$, $COOR^{6a}$, CN, $N(R^{6b})_2$ and $NO_2$;

$R^5$ are independently hydrogen, $C_{1-4}$ alkyl or $C_{1-4}$ alkyl$C_{3-7}$ cycloalkyl;

$R^{6a}$ are independently hydrogen, $C_{1-4}$ alkyl or $C_{1-4}$ fluoroalkyl;

$R^{6b}$ are independently hydrogen, $C_{1-4}$ alkyl or $C_{1-4}$ alkyl$C_{3-7}$ cycloalkyl;

$R^{11}$ is phenyl; and $R^{12}$ is hydrogen, $C_{1-4}$ alkyl or $C_{3-7}$ cycloalkyl;

provided that the compound is not:
a) 4-5-piperidin-4-yl-[1,2,4]oxadiazol-3-yl)pyridine;
b) 4-(3-pyridin-4-yl-[1,2,4]oxadiazol-5-yl)piperidine-1-carboxylic acid ᵗbutyl ester;
c) 4-[5-(4-butylcyclohexyl)-[1,2,4]oxadiazol-3-yl]pyridine;
d) 3-[5-(4-butylcyclohexyl)-[1,2,4]oxadiazol-3-yl]pyridine; or
e) 3-[5-(4-propylcyclohexyl)-[1,2,4]oxadiazol-3-yl]pyridine.

A further group of compounds which may be mentioned are the compounds of formula (Ib) and pharmaceutically acceptable salts thereof:

$$R^1\text{-A-V}\text{—B—}R^2 \quad \text{(Ib)}$$

wherein V is a 5-membered heteroaryl ring containing up to four heteroatoms selected from O, N and S;

A is $(CH_2)_n$;

B is $(CH_2)_n$, where one of the $CH_2$ groups may be replaced by O, $NR^5$, $S(O)_m$ or C(O);

n is independently 0, 1, 2 or 3;

m is 0, 1 or 2;

$R^1$ is 3- or 4-pyridyl or 4- or 5-pyrimidinyl, any of which may be optionally substituted by one or more substituents selected from halo, $C_{1-4}$ alkyl, $C_{1-4}$ fluoroalkyl, $C_{2-4}$ alkenyl, $C_{2-4}$ alkynyl, $C_{3-7}$ cycloalkyl, aryl, $OR^5$, CN, $NO_2$, $S(O)_m R^6$, $CON(R^6)_2$, $N(R^6)_2$, $NR^{10}COR^6$, $NR^{10}SO_2 R^6$, $SO_2 N(R^6)_2$, a 4- to 7-membered heterocyclyl group or a 5- or 6-membered heteroaryl group;

$R^2$ is 4- to 7-membered cycloalkyl substituted by $R^3$, C(O)$OR^3$, $C(O)R^3$ or $S(O)_2 R^3$, or 4- to 7-membered heterocyclyl, containing one or two nitrogen atoms, which are unsubstituted or substituted by C(O)$OR^4$, $C(O)R^3$ or $S(O)_2 R^3$;

$R^3$ is $C_{3-7}$ alkyl, $C_{3-7}$ alkenyl or $C_{3-7}$ alkynyl which may contain a $CH_2$ group that may be replaced by O, $C_{3-7}$ cycloalkyl, aryl, heterocyclyl, heteroaryl, $C_{1-4}$ alkyl$C_{3-7}$ cycloalkyl, $C_{1-4}$ alkylaryl, $C_{1-4}$ alkylheterocyclyl or $C_{1-4}$ alkylheteroaryl, any of which may be substituted with one or more substituents selected from halo, $C_{1-4}$ alkyl, $C_{1-4}$ fluoroalkyl, $OR^6$, CN, $N(R^6)_2$ and $NO_2$;

$R^4$ is $C_{2-7}$ alkyl, $C_{2-7}$ alkenyl or $C_{2-7}$ alkynyl which may contain a $CH_2$ group that may be replaced by O, or $C_{3-7}$ cycloalkyl, aryl, heterocyclyl, heteroaryl, $C_{1-4}$ alkyl$C_{3-7}$ cycloalkyl, $C_{1-4}$ alkylaryl, $C_{1-4}$ alkylheterocyclyl or $C_{1-4}$ alkylheteroaryl, any of which may be substituted with one or more substituents selected from halo, $C_{1-4}$ alkyl, $C_{1-4}$ fluoroalkyl, $OR^6$, CN, $N(R^6)_2$ and $NO_2$;

$R^5$ is hydrogen, $C(O)R^7$, $S(O)_2 R^8$ or $C_{1-4}$ alkyl optionally substituted by $OR^6$, $C_{3-7}$ cycloalkyl, aryl, heterocyclyl or heteroaryl, wherein the cyclic groups may be substituted with one or more substituents selected from halo, $C_{1-2}$ alkyl, $C_{1-2}$ fluoroalkyl, $OR^6$, CN, $N(R^6)_2$ and $NO_2$;

$R^6$ are independently hydrogen, or $C_{1-4}$ alkyl, $C_{3-7}$ cycloalkyl, aryl, heterocyclyl group or heteroaryl, wherein the cyclic groups may be substituted with one or more substituents selected from halo, $C_{1-4}$ alkyl, $C_{1-4}$ fluoroalkyl, $OR^9$, CN, $SO_2 CH_3$, $N(R^{10})_2$ and $NO_2$; or a group $N(R^{10})_2$ may form a 4- to 7-membered heterocyclic ring optionally containing a further heteroatom selected from O and $NR^{10}$;

$R^7$ is hydrogen, $C_{1-4}$ alkyl, $OR^6$, $N(R^6)_2$ aryl or heteroaryl;

$R^8$ is $C_{1-4}$ alkyl, $C_{1-4}$ fluoroalkyl, aryl or heteroaryl;

$R^9$ is hydrogen, $C_{1-2}$ alkyl or $C_{1-2}$ fluoroalkyl; and $R^{10}$ is hydrogen or $C_{1-4}$ alkyl;

provided that the compound is not:
a) 4-(5-piperidin-4-yl-[1,2,4]oxadiazol-3-yl)pyridine;
b) 4-(3-pyridin-4-yl-[1,2,4]oxadiazol-5-yl)piperidine-1-carboxylic acid ᵗbutyl ester;
c) 4-[5-(4-butylcyclohexyl)-[1,2,4]oxadiazol-3-yl]pyridine;
d) 3-[5-(4-butylcyclohexyl)-([2,4]oxadiazol-3-yl]pyridine; or
e) 3-[5-(4-propylcyclohexyl)-[1,2,4]oxadiazol-3-yl]pyridine.

A further specific group of compounds of the invention which may be mentioned are those of formula (Ie), or a pharmaceutically acceptable salt thereof:

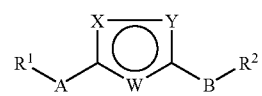

(Ic)

where two of W, X and Y are N, and the other is O;

A is $(CH_2)_n$;

B is $(CH_2)_n$, where one of the $CH_2$ groups may be replaced by O, $NR^6$, $S(O)_m$ or C(O);

n is independently 0, 1, 2 or 3;

m is 0, 1 or 2;

$R^1$ is 3- or 4-pyridyl or 4-pyrimidinyl any of which may be optionally substituted by one or more substituents selected from halo, CIA alkyl, $C_{1-4}$ fluoroalkyl, $C_{3-7}$ cycloalkyl, $OR^5$, CN, $NO_2$, $N(R^6)_2$, $CON(R^6)_2$ or a 5- or 6-membered heteroaryl group;

$R^2$ is 4- to 7-membered cycloalkyl substituted by $R^3$, C(O)$OR^3$, $C(O)R^3$ or $S(O)_2 R^3$, or 4- to 7-membered heterocyclyl, containing one or two nitrogen atoms, which is unsubstituted or substituted by C(O)$OR^4$, $C(O)R^3$ or $S(O)_2 R^3$;

$R^3$ is $C_{3-7}$ alkyl, $C_{3-7}$ alkenyl or $C_{3-7}$ alkynyl any of which may contain a $CH_2$ group that may be replaced by O, or $C_{3-7}$ cycloalkyl, aryl or $C_{1-4}$ alkylaryl, wherein the aryl groups may be substituted with one or more substituents selected from halo, $C_{1-4}$ alkyl, $C_{1-4}$ fluoroalkyl, $OR^5$, CN, $N(R^6)_2$ and $NO_2$;

$R^4$ is $C_{2-7}$ alkyl, $C_{2-7}$ alkenyl or $C_{2-7}$ alkynyl any of which may contain a $CH_2$ group that may be replaced by O, or $C_{3-7}$ cycloalkyl, aryl or $C_{1-4}$ alkylaryl, wherein the aryl groups may be substituted with one or more substituents selected from halo, $C_{1-4}$ alkyl, $C_{1-4}$ fluoroalkyl, $OR^5$, CN, $N(R^6)_2$ and $NO_2$;

$R^5$ are independently hydrogen, $C_{1-4}$ alkyl or $C_{1-4}$ fluoroalkyl; and $R^6$ are independently hydrogen and $C_{1-4}$ alkyl;

provided that the compound is not:
a) 4-(5-piperidin-4-yl-[1,2,4]oxadiazol-3-yl)pyridine;
b) 4-(3-pyridin-4-yl-[1,2,4]oxadiazol-5-yl)piperidine-1-carboxylic acid 'butyl ester;
c) 4-[5-(4-butylcyclohexyl)-[1,2,4]oxadiazol-3-yl]pyridine;
d) 3-[5-(4-butylcyclohexyl)-[1,2,4]oxadiazol-3-yl]pyridine; or
e) 3-[5-(4-propylcyclohexyl)-[1,2,4]oxadiazol-3-yl]pyridine.

A preferred group of compounds of the invention are the compounds of formula (Id), and pharmaceutically acceptable salts thereof:

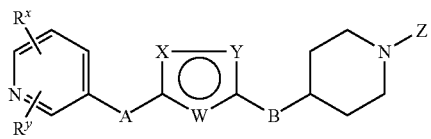

(Id)

where two of W, X and Y are N, and the other is O;
A is —CH=CH— or $(CH_2)_n$;
B is —CH=CH— or $(CH_2)_n$, where one of the $CH_2$ groups may be replaced by O, $NR^5$, $S(O)_m$ or $C(O)$;
n is independently 0, 1, 2 or 3, provided that not both n are 0;
m is independently 0, 1 or 2;
$R^x$ and $R^y$ are independently selected from hydrogen, halo, $C_{1-4}$ alkyl, $C_{1-4}$ fluoroalkyl, $C_{2-4}$ alkenyl, $C_{2-4}$ alkynyl, $C_{3-7}$ cycloalkyl, aryl, $OR^6$, CN, $NO_2$, $S(O)_mR^6$, $CON(R^6)_2$, $N(R^6)_2$, $NR^{10}COR^6$, $NR^{10}SO_2R^6$, $SO_2N(R^6)_2$, a 4- to 7-membered heterocyclyl group and a 5- or 6-membered heteroaryl group;
Z is $C(O)OR^4$, $C(O)R^3$, $S(O)_2R^3$, $C(O)NHR^4$ or a 5- or 6-membered nitrogen containing heteroaryl group;

$R^3$ is $C_{3-8}$ alkyl, $C_{3-8}$ alkenyl or $C_{3-8}$ alkynyl, any of which may be optionally substituted with up to 5 fluoro or chloro atoms, and may contain a $CH_2$ group that may be replaced by O, or $C_{3-7}$ cycloalkyl, aryl, heterocyclyl, heteroaryl, $C_{1-4}$ alkyl$C_{3-7}$ cycloalkyl, $C_{1-4}$ alkylaryl, $C_{1-4}$ alkylheterocyclyl or $C_{1-4}$ alkylheteroaryl, any of which may be optionally substituted with one or more substituents selected from halo, $C_{1-4}$ alkyl, $C_{1-4}$ fluoroalkyl, $OR^6$, CN, $CO_2C_{1-4}$ alkyl, $N(R^6)_2$ and $NO_2$;

$R^4$ is $C_{2-4}$ alkyl, $C_{2-8}$ alkenyl or $C_{2-8}$ alkynyl, any of which may be optionally substituted with up to 5 fluoro or chloro atoms, and may contain a $CH_2$ group that may be replaced by O, or $C_{3-7}$ cycloalkyl, aryl, heterocyclyl, heteroaryl, $C_{1-4}$ alkyl$C_{3-7}$ cycloalkyl, $C_{1-4}$ alkylaryl, $C_{1-4}$ alkylheterocyclyl or $C_{1-4}$ alkylheteroaryl, any of which may be substituted with one or more substituents selected from halo, $C_{1-4}$ alkyl, $C_{1-4}$ fluoroalkyl, $OR^6$, CN, $CO_2C_{1-4}$ alkyl, $N(R^6)_2$ and $NO_2$;

$R^6$ are independently hydrogen, or $C_{1-4}$ alkyl, $C_{3-7}$ cycloalkyl, aryl, heterocyclyl or heteroaryl, wherein the cyclic groups may be substituted with one or more substituents selected from halo, $C_{1-4}$ alkyl, $C_{1-4}$ fluoroalkyl, $OR^9$, CN, $SO_2CH_3$, $N(R^{10})_2$ and $NO_2$; or a group $N(R^{10})_2$ may form a 4- to 7-membered heterocyclic ring optionally containing a further heteroatom selected from O and $NR^{10}$;

$R^9$ is hydrogen, $C_{1-2}$ alkyl or $C_{1-2}$ fluoroalkyl; and
$R^{10}$ is hydrogen or $C_{1-4}$ alkyl.

A further preferred group of compounds of the invention are the compounds of formula (Ie), and pharmaceutically acceptable salts thereof:

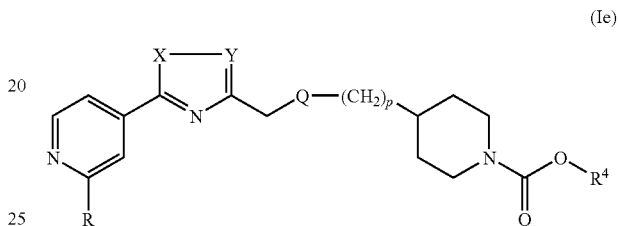

(Ie)

wherein one of X and Y is N, and the other is O;
Q is O, $NR^5$ or $CH_2$;
R is hydrogen, halo, $C_{1-4}$ alkyl, $C_{1-4}$ fluoroalkyl, $C_{2-4}$ alkenyl, $C_{2-4}$ alkynyl, $C_{3-7}$ cycloalkyl, aryl, $OR^6$, CN, $NO_2$, $S(O)_m R^6$, $CON(R^6)_2$, $N(R^6)_2$, $NR^{10}COR^6$, $NR^{10}SO_2R^6$, $SO_2N(R^6)_2$, a 4- to 7-membered heterocyclyl group or a 5- or 6-membered heteroaryl group;
$R^4$ is $C_{2-8}$ alkyl, $C_{2-8}$ alkenyl or $C_{2-8}$ alkynyl, any of which may be optionally substituted with up to 5 fluoro or chloro atoms, and contain a $CH_2$ group that may be replaced by O, or $C_{3-7}$ cycloalkyl, aryl, heterocyclyl, heteroaryl, $C_{1-4}$ alkyl$C_{3-7}$ cycloalkyl, $C_{1-4}$ alkylaryl, $C_{1-4}$ alkylheterocyclyl or $C_{1-4}$ alkylheteroaryl, any of which may be substituted with one or more substituents selected from halo, $C_{1-4}$ alkyl, $C_{1-4}$ fluoroalkyl, $OR^6$, CN, $CO_2C_{1-4}$ alkyl, $N(R^6)_2$ and $NO_2$;
$R^5$ is $C_{1-4}$ alkyl;
$R^6$ are independently hydrogen, or $C_{1-4}$ allyl, $C_{3-7}$ cycloalkyl, aryl, heterocyclyl or heteroaryl, wherein the cyclic groups may be substituted with one or more substituents selected from halo, $C_{1-4}$ alkyl, $C_{1-4}$ fluoroalkyl, $OR^9$, CN, $SO_2CH_3$, $N(R^{10})_2$ and $NO_2$; or a group $N(R^{10})_2$ may form a 4- to 7-membered heterocyclic ring optionally containing a further heteroatom selected from O and $NR^{10}$;
$R^9$ is hydrogen, $C_{1-2}$ alkyl or $C_{1-2}$ fluoroalkyl;
$R^{10}$ is hydrogen or $C_{1-4}$ alkyl; and
p is 0 or 1.

In the compounds of formula (Ie) R is preferably hydrogen, halo, $C_{1-4}$ alkyl, $C_{1-4}$ alkoxy or CN.

Specific compounds of the invention which may be mentioned are those included in the Examples and pharmaceutically acceptable salts thereof.

Particular compounds which may be mentioned are:
4-(3-Pyridin-4-yl-[1,2,4]oxadiazol-5-ylmethoxy)piperidine-1-carboxylic acid tert-butyl ester,
4-[5-(2-Cyanopyridin-4-yl)-[1,2,4]oxadiazol-3-ylmethoxy]piperidine-1-carboxylic acid tert-butyl ester,
4-(3-Pyridin-4-yl-[1,2,4]oxadiazol-5-ylmethoxy)piperidine-1-carboxylic acid cyclopentyl ester,
4-(3-Pyridin-4-yl-[1,2,4]oxadiazol-5-ylmethoxy)piperidine-1-carboxylic acid 2,2,2-trichloroethyl ester, 4-[Ethyl(3-pyridin-4-yl-[1,2,4]oxadiazol-5-ylmethyl) amino]piperidine-1-carboxylic acid tert-butyl ester,
4-[Methyl-(3-pyridin 4-yl-[1,2,4]oxadiazol-5-ylmethyl) amino]piperidine-1-carboxylic acid cyclopentyl ester, and
4-{[Methyl-(3-pyridin-4-yl-[1,2,4]oxadiazol-5-ylmethyl) amino]methyl}piperidine-1-carboxylic acid 2,2,2-trichloroethyl ester,
and pharmaceutically acceptable salts thereof.

As used herein, unless stated otherwise, "alkyl" as well as other groups having the prefix "alk" such as, for example, alkenyl, alkynyl, and the like, means carbon chains which may be linear or branched or combinations thereof. Examples of alkyl groups include methyl, ethyl, propyl, isopropyl, butyl, sec- and tert-butyl, pentyl, hexyl, heptyl and the like. "Alkenyl", "alkynyl" and other like terms include carbon chains having at least one unsaturated carbon-carbon bond.

The term "fluoroalkyl" includes alkyl groups substituted by one or more fluorine atoms, e.g. $CH_2F$, $CHF_2$ and $CF_3$.

The term "cycloalkyl" means carbocycles containing no heteroatoms, and includes monocyclic saturated carbocycles. Examples of cycloalkyl include cyclopropyl, cyclobutyl, cyclopentyl, cyclohexyl and cycloheptyl.

The term "halo" includes fluorine, chlorine, bromine, and iodine atoms.

The term "aryl" includes phenyl and naphthyl, in particular phenyl.

Unless otherwise indicated the term "heterocyclyl" and "heterocyclic ring" includes 4 to 10-membered monocyclic and bicyclic saturated rings, e.g. 4 to 7-membered monocyclic saturated rings, containing up to three heteroatoms selected from N, O and S. Examples of heterocyclic rings include oxetane, tetrahydrofuran, tetrahydropyran, oxepane, oxocane, thietane, tetrahydrothiophene, tetrahydrothiopyran, thiepane, thiocane, azetidine, pyrrolidine, piperidine, azepane, azocane, [1,3]dioxane, oxazolidine, piperazine, and the like. Other examples of heterocyclic rings include the oxidised forms of the sulfur-containing rings. Thus, tetrahydrothiophene 1-oxide, tetrahydrothiophene 1,1-dioxide, tetrahydrothiopyran 1-oxide, and tetrahydrothiopyran 1,1-dioxide are also considered to be heterocyclic rings.

Examples of heterocyclic rings that $R^2$ may represent include azetidine, pyrrolidine, piperidine and piperazine. $R^2$ heterocyclyl groups may also contain additional heteroatoms, e.g. morpholine.

Unless otherwise stated, the term "heteroaryl" includes mono- and bicyclic 5- to 10-membered, e.g. monocyclic 5- or 6-membered, heteroaryl rings containing up to 4 heteroatoms selected from N, O and S. Examples of such heteroaryl rings are furyl, thienyl, pyrrolyl pyrazolyl, imidazolyl oxazolyl, isoxazolyl, thiazolyl, isothiazolyl, triazolyl, oxadiazolyl, thiadiazolyl, tetrazolyl, pyridinyl, pyridazinyl, pyrimidinyl, pyrazinyl and triazinyl. Bicyclic heteroaryl groups include bicyclic heteroaromatic groups where a 5- or 6-membered heteroaryl ring is fused to a phenyl or another heteroaromatic group. Examples of such bicyclic heteroaromatic rings are benzofuran, benzothiophene, indole, benzoxazole, benzothiazole, indazole, benzimidazole, benzotriazole, quinoline, isoquinoline, quinazoline, quinoxaline and purine.

Compounds described herein may contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above formula (I) is shown without a definitive stereochemistry at certain positions. The present invention includes all stereoisomers of formula (I) and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

When a tautomer of the compound of formula (I) exists, the present invention includes any possible tautomers and pharmaceutically acceptable salts thereof and mixtures thereof, except where specifically drawn or stated otherwise.

When the compound of formula (I) and pharmaceutically acceptable salts thereof exist in the form of solvates or polymorphic forms, the present invention includes any possible solvates and polymorphic forms. A type of a solvent that forms the solvate is not particularly limited so long as the solvent is pharmacologically acceptable. For example, water, ethanol, propanol, acetone or the like can be used.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like Since the compounds of formula (I) are intended for pharmaceutical use they are preferably provided in substantially pure form, for example at least 60% pure, more suitably at least 75% pure, especially at least 98% pure (% are on a weight for weight basis).

The compounds of formula (I) can be prepared as described below, in which, for illustrative purposes, —V— is shown as a group of the formula:

and $R^1$, $R^2$, $R^3$, $R^4$, A, B, W, X and Y are as defined above.

The compounds of formula (I), in which X=N, Y=O and W=N, may be prepared according to the method illustrated in Scheme 1. The nitriles of formula 2 are either commercially available or can be synthesised using known techniques. Compounds of formula 2 are treated with hydroxylamine in a suitable solvent, such as ethanol-water, at elevated temperature, to afford amidoximes of formula 3 (synthesis of amidoximes is further described by A. R. Martin et al, J. Med. Chem., 2001, 44, 1560). Compounds of formula 3 are subsequently condensed with acids of formula 4, which are themselves either commercially available or can be readily synthesised using known techniques. The condensation firstly entails activation of compounds of formula 4 by, for example, formation of the mixed anhydride, in which the acid is treated with a chloroformate, such as isobutylchloroformate, in the presence of a suitable base, such as triethylamine, in a suitable solvent, such as THF or toluene, followed by addition of compounds of formula 3. Alternatively, compounds of formula 4 may be activated by conversion to the acid halide, generated by treatment of the acid with, for example, oxalyl chloride in a suitable solvent, such as $CH_2Cl_2$-DMF. The intermediates arising from the condensation of amidoximes of formula 3 and acids of formula 4 are dissolved in an appropriate solvent, such as toluene or xylene, and heated under reflux, with concomitant removal of water by Dean-Stark apparatus or by molecular sieves, to form oxadiazoles of formula (I). Alternatively, amidoximes of formula 3 can firstly be treated with a suitable base, for example sodium hydride, in an appropriate solvent, such as THF, and subsequently esters of formula 5. Heating of this mixture also generates oxadiazoles of formula (I) (this process is further illustrated by R. H. Mach et al, Bioorg. Med. Chem., 2001, 9, 3113).

Scheme 1

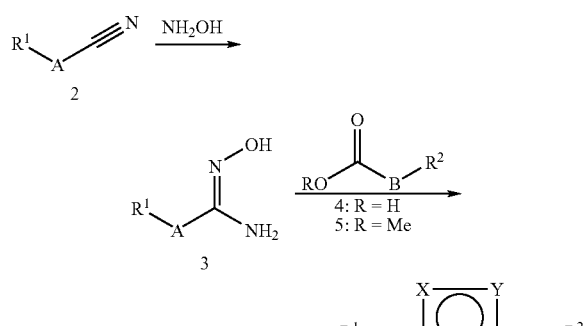

Compounds of formula (I) in which X=O, Y=N and W=N may be prepared according to the method outlined in Scheme 2. The nitriles of formula 6 are either commercially available or can be synthesised using known techniques. These are converted to the corresponding amidoximes of formula 7, as described above, and subsequently condensed with acids of formula 8, which are commercially available or can readily be synthesised by those skilled in the art. This condensation is performed in a fashion analogous to that described in Scheme 1, to afford the corresponding oxadiazoles of formula (I).

Scheme 2

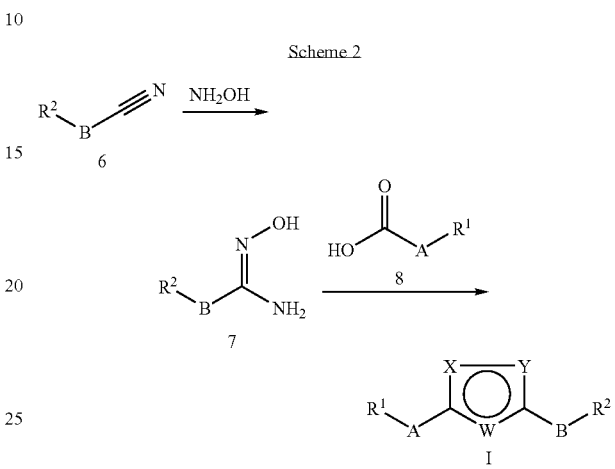

Compounds of formula (I) in which X=N, Y=N and W=O can be synthesised as outlined in Scheme 3. The acyl chlorides of formula 9 are either commercially available or may be synthesised using known methods. The acid hydrazides of formula 10 can be readily obtained by, for example, treating an ethanolic solution of the corresponding ester with hydrazine (for further details see K. M. Kahn et al, Bioorg. Med. Chem., 2003, 11, 1381). Treating the acyl chlorides of formula 9 with the acid hydrazides of formula 10 in a suitable solvent, such as pyridine, affords compounds of formula 11 (further illustrated by V. N. Kerr et al, J. Am. Chem. Soc., 1960, 82, 186), which are then converted by $POCl_3$ at elevated temperature to compounds of formula (I) (this process is further described by S-A. Chen et al., J. Am. Chem. Soc., 2001, 123, 2296). Similarly, compounds of formula (I) where X=Y=W=N can be prepared via the condensation of the amidrazone analogue of 10 with the appropriate activated carboxylic acid derivative, such as 9. The reactive groups in this reaction may be exchanged, i.e., an amidrazone of formula $R^1$-A-C(=NH)NHNH$_2$ can form a compound of formula (I) by condensation with an activated carboxylic acid derivative
LG-C(=O)—B—$R^2$ where LG is halogen or oxycarbonyl (P. H. Olesen et al., J. Med. Chem., 2003, 46, 3333-3341).

Scheme 3

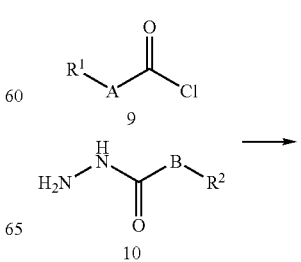

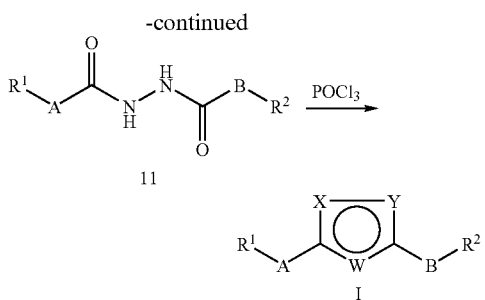

Compounds of formula (I) where X=N, Y=N, and W=S can also be prepared from compounds of formula 11 by heating with Lawesson's reagent in a suitable solvent, such as toluene or acetonitrile (D. Alker et al., J. Med. Chem., 1989, 32, 2381-2388). Compounds of formula (I) where X=S, Y=N and W=N can be formed from compounds of formula 12 (Scheme 4) which are commercially available, or can be readily synthesised from the corresponding carbonyl compound and Lawesson's reagent under standard conditions. Treating a compound of formula 12 with a compound of formula 13 in a suitable solvent such as dichloromethane at about 20° C. gives compounds of formula 14. Compounds of formula 13 can be obtained by treating the corresponding dimethylamide with Meerwein's reagent (for details see M. Brown U.S. Pat. No. 3,092,637). Compounds of formula 14 are then cyclised using hydroxylamine-sulfonic acid in the presence of a base, such as pyridine, in a suitable solvent such as methanol (for further details, see A. MacLeod et al, L Med. Chem., 1990, 33, 2052).

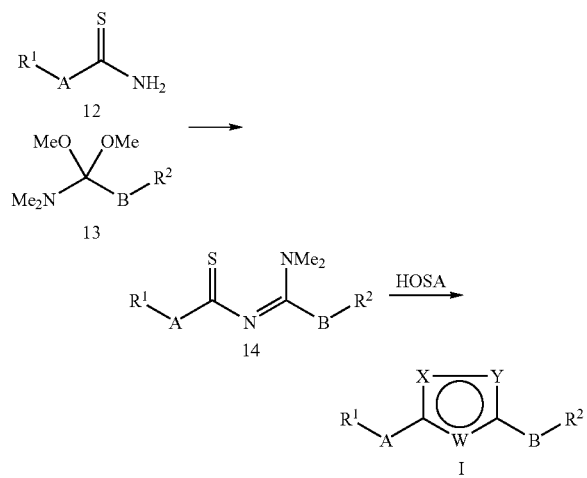

The regioisomeric derivatives of formula (I), where X=N, Y=S and W=N, can be formed in a similar manner by reversing the functionality of the reactants so the $R^1$ fragment contains the acetal moiety and the $R^2$ fragment contains the thiocarbonyl.

Compounds of formula (I) where W=O, X=N and Y=CH can be formed from compounds of formula 15 (Scheme 5). Compounds of formula 15 are commercially available or synthesised using known techniques. Chlorides of formula 16 are commercially available, or can readily be formed by chlorinating the corresponding ketone using standard conditions, for example, bubbling chlorine gas through a methanol solution of the ketone (for further details see R. Gallucci & R. Going, J. Org. Chem., 1981, 46, 2532). Mixing a compound of formula 15 with a chloride of formula 16 in a suitable solvent, such as toluene, with heating, for instance at about 100° C. gives compounds of formula (I) (for further information, see k Hassner et al, Tetrahedron, 1989, 45, 6249). Compounds of formula (I) where W=O, X=CH and Y=N can be formed is a similar fashion by reversing the functionality of the reactants so the $R^1$ fragment contains the haloketone moiety and the $R^2$ fragment contains the C(O)NH$_2$.

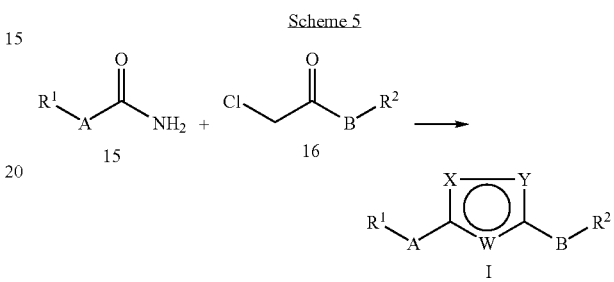

Alternatively, compounds of formula (I) where X=S, W=N and Y=CH can also be formed from compounds of formula 16. Heating an compound of formula 15 with phosphorus pentasulfide, followed by the addition of a compound of formula 16 followed by further heating gives compounds of formula (I) (for further details, see R. Kurkjy & E. Brown, J. Am. Chem. Soc., 1952, 74, 5778). The regioisomeric compounds where X=CH, W=N and Y=S can be formed is a similar fashion by reversing the functionality of the reactants, so the $R^1$ fragment contains the haloketone moiety and the $R^2$ fragment contains the C(O)NH$_2$.

Compounds of formula I where W=N, X=O and Y=CH can be formed from compounds of formula 15 and formula 17 (Scheme 6) under similar conditions to those outlined for Scheme 5. Compounds of formula I where W=S, X=N and Y=CH can also be formed from compounds of formula 15 and formula 17 using the conditions involving phosphorus pentasulfide described above.

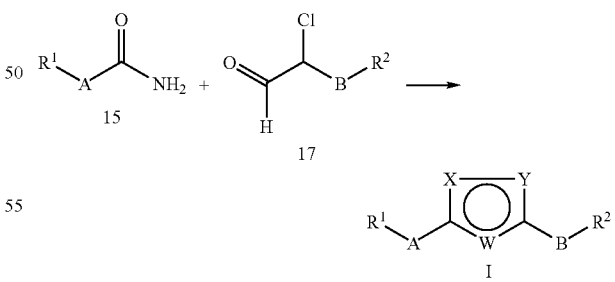

Compounds of formula (I) where X=O, Y=N and W=CH, and where X=N, Y=O and W=CH and can be formed from compounds of formula 20 (Scheme 7). Acylation of compounds of formula 18 with a compound of formula 19, where Q is alkoxide or chloride, can occur under standard conditions, for example, deprotonation of ketone 18 with a suitable base, such as lithium diisopropylamide or potassium ethoxide, in a suitable solvent, such as tetrahydrofuran, generally at low temperature. Treatment of compounds of formula 20 with hydroxylamine, in a suitable solvent, such as ethanol, at elevated temperature, for example 75° C., yields compounds of formula (I) as a mixture of both regioisomers of the isoxazole. Using standard separation techniques, such as chromatography on silica gel, the individual isomers can be isolated (for further details, see M. Rowley et al, J. Med. Chem., 1997, 40, 2374).

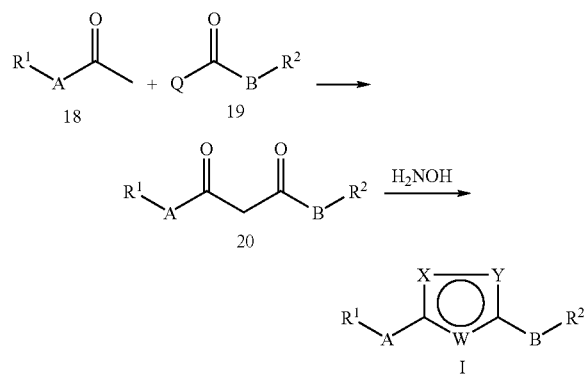

Scheme 7

Compounds of formula (I) where X=S, Y=N and W=CH can be formed by hydrogenation of a compound of formula (I) where X=O, Y=N and W=CH, with platinum oxide in a suitable solvent such as ethanol, followed by heating with phosphorus pentasulfide to give compounds of formula (I) where X=S, Y=N and W=CH (for further details, see G. Wiegand et al, J. Med. Chem., 1971, 14, 1015). For details of the synthesis of the regioisomer where X=N, Y=S and W=CH also see G. Wiegand ibid).

Compounds of formula (I) where X=N, Y=N and W=CH can be formed from compounds of formula 20. Treatment of compounds of formula 20 with hydrazine in a suitable solvent, such as methanol, would give rise to compounds of formula (I) where X=N, Y=N and W=CH (this process is further illustrated by R. Baker et al, J. Med. Chem., 1997, 40, 2374).

Compounds of formula (I) in which X=CH, Y=N and W=N can be synthesised as described in Scheme 8. Bromides of formula 23 are either commercially available or may be synthesised from the corresponding ketone by, for example, treating an aqueous solution of the ketone with $Br_2$ and HBr (as described by J. Y. Becker et al, Tetrahedron Lett., 2001, 42, 1571). The amidines of formula 22 may be synthesised by known methods, for example by treatment of the corresponding alkyl imidates of formula 21 with ammonia in a suitable solvent, such as ethanol (as detailed by D. A. Pearson et al, J. Med. Chem., 1996, 39, 1372). The imidates of formula 21 may in turn be generated by, for example, treatment of the corresponding nitrile with HCl in a suitable solvent, such as methanol (for further details see 3. P. Lokensgard et al, J. Org. Chem., 1985, 50, 5609). Reaction of amidines of formula 22 with bromides of formula 23 in a suitable solvent, such as DMF, affords compounds of formula (I) (illustrated by N. J. Liverton et al, J. Med. Chem., 1999, 42, 2180).

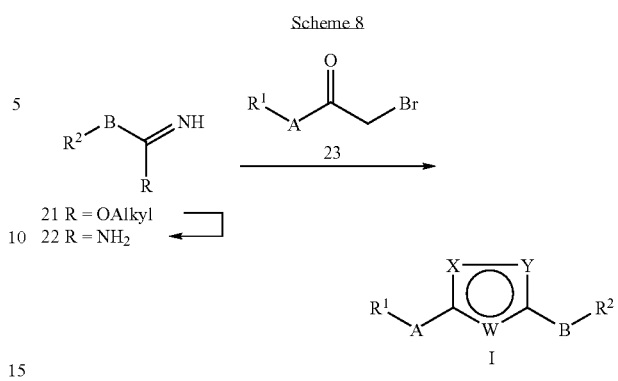

Scheme 8

The regioisomeric compounds where X=N, Y=CH and W=N can be formed in a similar fashion by reversing the functionality of the reactants, so the $R^1$ fragment contains the amidine moiety and the $R^2$ fragment contains the bromide.

Compounds of formula (I) in which X=CH, Y=CH and W=N can be synthesised as illustrated in Scheme 9. Diketones of formula 25 are readily accessible by, for example, the condensation of ketones of formula 24, which are commercially available or are readily synthesised using known techniques, with bromides of formula 23 in a suitable solvent, such as benzene using an appropriate catalyst. Illustrative examples are described by O. G. Kulinkovich et al, Synthesis, 2000, 9, 1259. Using a Paal-Knorr reaction, diketones of formula 25 may be treated with, for example, ammonium carbonate in a suitable solvent, such as ethanol at elevated temperature (for further details see R. A. Jones et al, Tetrahedron, 1996, 52, 8707) to afford compounds of formula (I).

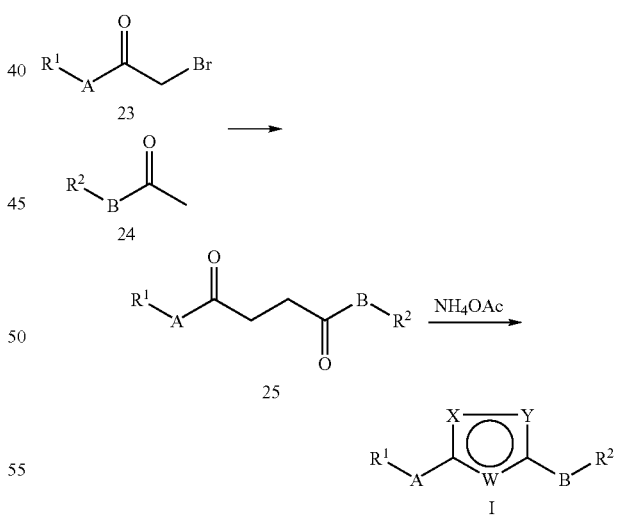

Scheme 9

Compounds of formula (I) in which $R^2$ contains either a carbamate or a sulfonamide group may be synthesised as described in Scheme 10. Compounds of formula 26, in which P represents a suitable protecting group, for example tert-butoxycarbonyl (Boc), may be synthesised as outlined in Schemes 1-9 above. The protecting group is firstly removed under suitable conditions to afford compounds of formula 27. In the case of the Boc group this can be achieved by treatment of compounds of formula 26 with a suitable acid, such as trifluoroacetic acid, in an appropriate solvent, such as CH$_2$Cl$_2$. Treatment of compounds of formula 27 with chloroformates of formula 28, which are generally commercially available or can be readily synthesised, in a suitable solvent such as CH$_2$Cl$_2$, in the presence of a suitable base, such as triethylamine, affords compounds of formula (I). Similarly, compounds of formula 27 may be reacted with sulfonyl chlorides of formula 29, which are generally commercially available or can readily be synthesised, in a suitable solvent, such as CH$_2$Cl$_2$, in the presence of a suitable base, such as triethylamine, to afford compounds of formula (I). Compounds of formula (I) in which R$^2$ contains a urea moiety may be prepared by reacting a compound of formula 13 with an isocyanate of formula O=C=N—R$^4$. Furthermore, compounds of formula (I) in which R$^2$ is 4-7-membered heterocyclyl substituted with a heteroaryl group may be prepared by reacting the amine 27 with the appropriate heteroaryl chloride or bromide under Pd(0) catalysis in the presence of a suitable ligand and base (Urgaonkar, S.; Hu, J.-H.; Verkade, J. G. *J. Org. Chem.* 2003, 68, 8416-8423).

Scheme 10

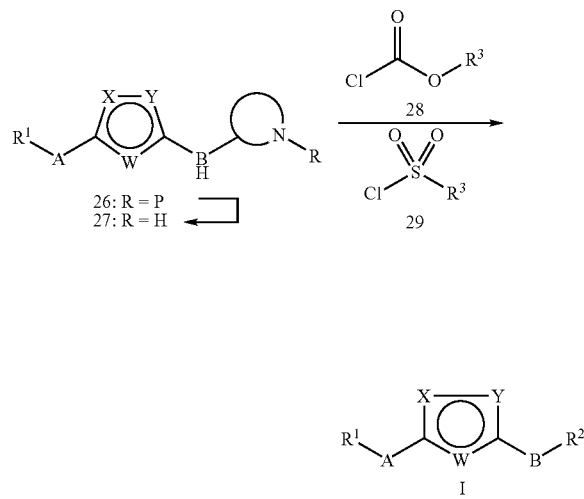

Compounds of formula (I) in which R$^2$ contains an amide group may be synthesised from compounds of formula 27 and a suitable acid (R$^3$COOH), or activated derivative thereof, in an amide bond forming reaction.

Compounds of formula (I) where R$^2$ contains an ester moiety may be synthesised as illustrated in Scheme 11. Compounds of formula 30 in which R is an alkyl group, for sample a methyl group, may be synthesised using procedures described in Schemes 1-9. The alkyl group is firstly removed under appropriate conditions to afford compounds of formula 31. For example, when R=Me compounds of formula 30 may be hydrolysed in the presence of a suitable alkali, for example LiOH, in a suitable solvent, such as water-methanol. The acids of formula 31 are then condensed with alcohols of formula 32, which are commercially available or can be synthesised using known techniques. The condensation may be achieved by, for example, treating compounds of formula 31 with alcohols of formula 32 in the presence of thionyl chloride, giving rise to compounds of formula (I).

Scheme 11

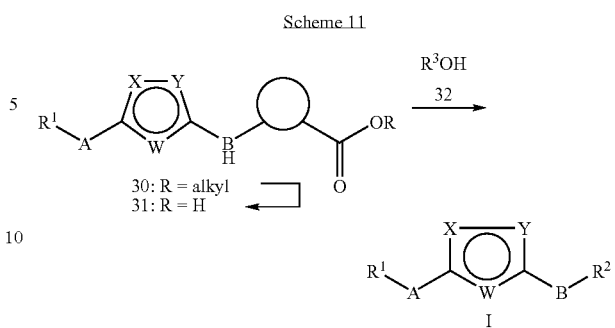

Compounds of formula (I) where R$^3$ contains an ether group may also be synthesised from compounds of formula 30 as illustrated in Scheme 12. Compounds of formula 30 may be converted to the corresponding alcohol 33 by the action of a suitable reducing agent, for example diisobutylaluminum hydride, in a suitable solvent, such as CH$_2$Cl$_2$, and can then be treated firstly with a suitable base, such as sodium hydride, in a suitable solvent, such as THF, followed by an appropriate alkylating agent, such as an alkyl halide of formula 34 to afford compounds of formula (I).

Scheme 12

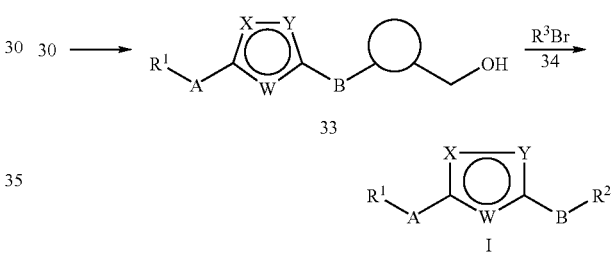

Compounds of formula (I) where B contains a NR$^5$ group where R$^5$ is hydrogen can be further transformed into compounds of formula (I) where R$^5$ is C(O)R$^7$, S(O)$_2$R$^8$, or an optionally substituted C$_{1-4}$ alkyl group using standard techniques known to those with skill in the art for acylation, sulfonylation and reductive amination, respectively.

Compounds of the formula (I) where R$^1$ is pyridyl optionally substituted with CN can be prepared from the corresponding unsubstituted pyridine by the Reissert reaction (Fife, W. K. *J. Org. Chem.* 1983, 48, 1375-1377). Similar reactions can be used to prepare the compounds where R$^1$ is pyridyl optionally substituted with halogen (Walters, M. A.; Shay, J. J. *Tetrahedron Lett.* 1995, 36, 7575-7578). The compounds where R$^1$ is pyridyl optionally substituted with halogen can be transformed into the corresponding compounds where R$^1$ is pyridyl optionally substituted with C$_{1-4}$ alkyl by transition metal-catalysed cross-coupling reactions (Fürstner, A., et al. *J. Am. Chem. Soc.* 2002, 124, 13856-13863).

Other compounds of formula (I) may be prepared by methods analogous to those described above or by methods known per se.

Further details for the preparation of the compounds of formula (I) are found in the examples.

The compounds of formula (I) may be prepared singly or as compound libraries comprising at least 2, for example 5 to 1,000, compounds and more preferably 10 to 100 compounds of formula (I). Compound libraries may be prepared by a combinatorial "split and mix" approach or by multiple parallel synthesis using either solution or solid phase chemistry, using procedures known to those skilled in the art.

During the synthesis of the compounds of formula (I), labile functional groups in the intermediate compounds, e.g. hydroxy, carboxy and amino groups, may be protected. The protecting groups may be removed at any stage in the synthesis of the compounds of formula (I) or may be present on the final compound of formula (I). A comprehensive discussion of the ways in which various labile functional groups may be protected and methods for cleaving the resulting protected derivatives is given in, for example, Protective Groups in Organic Chemistry, T. W. Greene and P. G. M. Wuts, (1991) Wiley-Interscience, New York, $2^{nd}$ edition.

Any novel intermediates as defined above are also included within the scope of the invention.

As indicated above the compounds of formula (I) are useful as GPR116 agonists, e.g. for the treatment and/or prophylaxis of obesity and diabetes. For such use the compounds of formula (I) will generally be administered in the form of a pharmaceutical composition.

The invention also provides a compound of formula (I), including the compounds of provisos c) to e), or a pharmaceutically acceptable salt thereof, for use as a pharmaceutical.

The invention also provides a pharmaceutical composition comprising a compound of formula (I), including the compounds of provisos c) to e), in combination with a pharmaceutically acceptable carrier.

Preferably the composition is comprised of a pharmaceutically acceptable carrier and a non-toxic therapeutically effective amount of a compound of formula (I), including the compounds of provisos c) to e), or a pharmaceutically acceptable salt thereof.

Moreover, the invention also provides a pharmaceutical composition for the treatment of disease by modulating GPR116, as a regulators of satiety, e.g. resulting in the prophylactic or therapeutic treatment of obesity, or for the treatment of diabetes, comprising a pharmaceutically acceptable carrier and a non-toxic therapeutically effective amount of compound of formula (I), including the compounds of provisos a) to e), or a pharmaceutically acceptable salt thereof.

The pharmaceutical compositions may optionally comprise other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds of formula (I), including the compounds of provisos a) to e), or pharmaceutically acceptable salts thereof can be combined as the active ingredient in intimate admixture with a pharmaceutical carrier according to conventional pharmaceutical compounding techniques. The carrier may take a wide variety of forms depending on the form of preparation desired for administration, e.g. oral or parenteral (including intravenous).

Thus, the pharmaceutical compositions can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a nonaqueous liquid, as an oil-in-water emulsion, or as a water-in-oil liquid emulsion. In addition to the common dosage forms set out above, the compound of formula (I), including the compounds of provisos a) to e), or a pharmaceutically acceptable salt thereof may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

The compounds of formula (I), including the compounds of provisos a) to e), or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent Molded tablets may be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient For example, a formulation intended for the oral administration to humans may contain from about 0.5 mg to about 5 g of active agent, compounded with an appropriate and convenient amount of carrier material which may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, using a compound of formula (I), or a pharmaceutically acceptable salt thereof; via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of formula (I), or pharmaceutically acceptable salts thereof, may also be prepared in powder or liquid concentrate form.

Generally, dosage levels on the order of 0.01 mg/kg to about 150 mg/kg of body weight per day are useful in the treatment of the above-indicated conditions, or alternatively about 0.5 mg to about 7 g per patient per day. For example, obesity may be effectively treated by the administration of from about 0.01 to 50 mg of the compound per kilogram of body weight per day, or alternatively about 0.5 mg to about 3.5 g per patient per day.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

The compounds of formula (I), including the compounds of provisos a) to e), may be used in the treatment of diseases or conditions in which GPR116 plays a role.

Thus the invention also provides a method for the treatment of a disease or condition in which GPR116 plays a role comprising a step of administering to a subject in need thereof an effective amount of a compound of formula (I), including the compounds of provisos a) to e), or a pharmaceutically acceptable salt thereof.

Diseases or conditions in which GPR116 plays a role include obesity and diabetes. In the context of the present application the treatment of obesity is intended to encompass the treatment of diseases or conditions such as obesity and other eating disorders associated with excessive food intake e.g. by reduction of appetite and body weight, maintenance of weight reduction and prevention of rebound and diabetes (including Type 1 and Type 2 diabetes, impaired glucose tolerance, insulin resistance and diabetic complications such as neuropathy, nephropathy, retinopathy, cataracts, cardiovascular complications and dyslipidaemia). And the treatment of patients who have an abnormal sensitivity to ingested fats leading to functional dyspepsia The invention also provides a method for the regulation of satiety comprising a step of administering to a subject in need thereof an effective amount of a compound of formula (I), including the compounds of provisos a) to e), or a pharmaceutically acceptable salt thereof.

The invention also provides a method for the treatment of obesity comprising a step of administering to a subject in need thereof an effective amount of a compound of formula (I), including the compounds of provisos a) to e), or a pharmaceutically acceptable salt thereof.

The invention also provides a method for the treatment of diabetes, including Type 1 and Type 2 diabetes comprising a step of administering to a patient in need thereof an effective amount of a compound of formula (I), including the compounds of provisos a) to e), or a pharmaceutically acceptable salt thereof.

The invention also provides a compound of formula (I), including the compounds of provisos a) to e), or a pharmaceutically acceptable salt thereof, for use in the treatment of a condition as defined above.

The invention also provides the use of a compound of formula (I), including the compounds of provisos a) to e), or a pharmaceutically acceptable salt thereof; in the manufacture of a medicament for the treatment of a condition as defined above.

In the methods of the invention the term "treatment" includes both therapeutic and prophylactic treatment.

The compounds of formula (I), including the compounds of provisos a) to e), or pharmaceutically acceptable salts thereof, may be administered alone or in combination with one or more other therapeutically active compounds. The other therapeutically active compounds may be for the treatment of the same disease or condition as the compounds of formula (I), including the compounds of provisos a) to e), or a different disease or condition. The therapeutically active compounds may be administered simultaneously, sequentially or separately.

The compounds of formula (I), including the compounds of provisos a) to e), may be administered with other active compounds for the treatment of obesity and/or diabetes, for example insulin and insulin analogs, gastric lipase inhibitors, pancreatic lipase inhibitors, sulfonyl ureas and analogs, biguanides, α2 agonists, glitazones, PPAR-γ agonists, mixed PPAR-α/γ agonists, RXR agonists, fatty acid oxidation inhibitors, α-glucosidase inhibitors, β-agonists, phosphodiesterase inhibitors, lipid lowering agents, glycogen phosphorylase inhibitors, antiobesity agents e.g. pancreatic lipase inhibitors, MCH-1 antagonists and CB-1 antagonists (or inverse agonists), amylin antagonists, lipoxygenase inhibitors, somostatin analogs, glucokinase activators, glucagon antagonists, insulin signalling agonists, PTP1B inhibitors, gluconeogenesis inhibitors, antilypolitic agents, GSK inhibitors, galanin receptor agonists, anorectic agents, CCK receptor agonists, leptin, serotonergic/dopaminergic antiobesity drugs, CRF antagonists, CRF binding proteins, thyromimetic compounds, aldose reductase inhibitors, glucocorticoid receptor antagonists, NHE-1 inhibitors or sorbitol dehydrogenase inhibitors.

Combination therapy comprising the administration of a GPR116 agonist and at least one other antiobesity agent represents a further aspect of the invention.

The present invention also provides a method for the treatment of obesity in a mammal, such as a human, which method comprises administering an effective amount of a GPR116 agonist and another antiobesity agent, to a mammal in need thereof.

The invention also provides the use of a GPR116 agonist and another antiobesity agent for the treatment of obesity.

The invention also provides the use of a GPR116 agonist in the manufacture of a medicament for use in combination with another antiobesity agent, for the treatment of obesity.

The GPR116 agonist and the other antiobesity agent(s) may be co-administered or administered sequentially or separately.

Co-administration includes administration of a formulation which includes both the GPR116 agonist and the other antiobesity agent(s), or the simultaneous or separate administration of each agent. Where the pharmacological profiles of the GPR116 agonist and the other antiobesity agent(s) allow it, coadministration of the two agents may be preferred.

The invention also provides the use of a GPR116 agonist and another antiobesity agent in the manufacture of a medicament for the treatment of obesity.

The invention also provides a pharmaceutical composition comprising a GPR116 agonist and another antiobesity agent, and a pharmaceutically acceptable carrier. The invention also encompasses the use of such compositions in the methods described above.

GPR116 agonists which may be used in the combination therapies according to this aspect of the invention include those compounds described herein and also those disclosed in WO04/065380 and WO04/076413.

GPR116 agonists are of particular use in combination with centrally acting antiobesity agents as such combinations may avoid the risk of adverse side effects which may be encountered if two centrally acting antiobesity agents are administered in combination.

The other antiobesity agent for use in the combination therapies according to this aspect of the invention is preferably a CB-1 modulator, e.g. a CB-1 antagonist or inverse agonist. Examples of CB-1 modulators include SR141716 (rimonabant) and SLV-319 ((4S)-(-)-3-(4-chlorophenyl)-N-methyl-N-[(4-chlorophenyl)sulfonyl]-4-phenyl-4,5-dihydro-IH-pyrazole-1-carboxamide); as well as those compounds disclosed in EP576357, EP656354, WO 03/018060, WO 03/020217, WO 03/020314, WO 03/026647, WO 03/026648, WO 03/027076, WO 03/040105, WO 03/051850, WO 03/051851, WO 03/053431, WO 03/063781, WO 03/075660, WO 03/077847, WO 03/078413, WO 03/082190, WO 03/082191, WO 03/082833, WO 03/084930, WO 03/084943, WO 03/086288, WO 03/087037, WO 03/088968, WO 04/012671, WO 04/013120, WO 04/026301, WO 04/029204, WO 04/034968, WO 04/035566, WO 04/037823 WO 04/052864, WO 04/058145, WO 04/058255, WO 04/060870, WO 04/060888, WO 04/069837, WO 04/069837, WO 04/072076, WO 04/072077, WO 04/078261 and WO 04/108728, and the references disclosed therein.

Other diseases or conditions in which GPR116 has been suggested to play a role include those described in WO 00/50562 and U.S. Pat. No. 6,468,756, for example cardiovascular disorders, hypertension, respiratory disorders, gestational abnormalities, gastrointestinal disorders, immune disorders, musculoskeletal disorders, depression, phobias, anxiety, mood disorders and Alzheimer's disease.

All publications, including, but not limited to, patents and patent application cited in this specification, are herein incorporated by reference as if each individual publication were specifically and individually indicated to be incorporated by reference herein as fully set forth.

The invention will now be described by reference to the following examples which are for illustrative purposes and are not to be construed as a limitation of the scope of the present invention.

EXAMPLES

Materials and Methods

Column chromatography was carried out on $SiO_2$ (40-63 mesh) unless specified otherwise.

LCMS data were obtained as follows: Atlantis 3μ $C_{18}$ column (2.1×30.0 mm, flow rate 0.85 ml/min) eluting with a $H_2O$-MeCN solution containing 0.1% $HCO_2H$ over 6 min with UV detection at 220 nm Gradient information: 0.0-0.3 min 100% $H_2O$; 0.3-4.25 min: Ramp to 10% $H_2O$-90% $CH_3CN$; 4.25 min 4.4 min: Ramp to 100% $CH_3CN$; 4.4-4.9 min: Hold at 100% MeCN; 4.9-6.0 min: Return to 100% $H_2O$. The mass spectra were obtained using an electrospray ionisation source in either the positive ($ES^+$) ion or negative ion ($ES^-$) mode. Atmospheric Pressure Chemical Ionisation (APCI) spectra were obtained on a FinniganMat SSQ 7000C instrument.

$^1H$ nmr spectra were recorded on a Varian Mercury 400 spectrometer, operating at 400 MHz. Chemical shifts are reported as ppm relative to tetramethylsilane ($\delta$=0).

HPLC was performed using a Phenomenex™ 10 $\mu C_{18}$ column (210×21 mm) eluting with a $H_2O$—$CH_3CN$ solution at 20 ml/min, with UV detection at 220 nm. Typical gradient 0-0.5 min, 10% $CH_3CN$-90% $H_2O$; 0.5 min-10 min, ramp to 90% $CH_3CN$-10% $H_2O$ and hold at 90% $CH_3CN$-10% $H_2O$ for 5 min; 15 min-16 min, return to 10% $CH_3CN$-90% $H_2O$.

The syntheses of the following compounds have been reported previously:

3-(2-Cyanopyridin-4-yl)propyl acetate: P. L. Ornstein et al., J. Med. Chem., 1991, 34, 90-97;

(N-Hydroxycarbamimidoylmethyl)carbamic acid tert-butyl ester: WO03/082861;

N-Hydroxyisonicotinamidine and N-hydroxynicotinamidine: A. R. Martin et al, J. Med. Chem., 2001, 44, 1560-1563;

N-Hydroxy-2-pyridin-3-ylacetamidine and N-hydroxy-2-pyridin-4-ylacetamidine: WO 01/047901;

4-Mercaptopiperidine-1-carboxylic acid tert-butyl ester: U.S. Pat. No. 5,317,025;

4-Pentylcyclohexanecarbonitrile: J. C. Liang and J. O. Cross, Mol. Cryst. Liq. Cryst, 1986, 133, 235-244;

3-Pyridin-4-yl-[1,2,4]oxadiazole-5-carboxylic acid ethyl ester: EP647635;

4-(3-Bromo-2-oxopropyl)piperidine-1-carboxylic acid tert-butyl ester: WO04/013137.

Abbreviations and acronyms: Ac: Acetyl; Boc: tert-Butoxycarbonyl; t-Bu: tert-Butyl; CDI: 1,1'-Carbonyldiimidazole; dba: dibenzylideneacetone; DMF: N,N-Dimethylformamide; Et Ethyl; HPLC: High performance liquid chromatography; IH: Isohexane; LDA: Lithium diisopropylamide; mCPBA: 3-Chloroperoxybenzoic acid; Me: Methyl; PDC: Pyridinium dichromate; RP-HPLC: Reverse phase high performance liquid chromatography; RT: Retention time; rt: Room temperature; TFA: Trifluoroacetic acid; THF: Tetrahydrofuran; TMS: Trimethylsilyl.

Preparation 1:
4-Carboxymethoxypiperidine-1-carboxylic acid tert-butyl ester

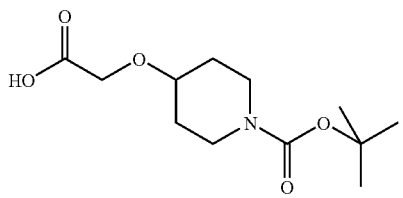

Sodium hydride (596 mg of a 60% dispersion in oil, 14.9 mmol) was added portionwise to a stirred solution of tert-butyl-4-hydroxypiperidine-1-carboxylate (1.0 g, 5 mmol) in anhydrous THF (20 ml) at rt. After 15 min, bromoacetic acid (1.38 g, 9.94 mmol) was introduced and stirring continued for 5 h. Additional bromoacetic acid (5 mmol) and sodium hydride (5 mmol) were added and stirring continued for 24 h. The reaction was quenched with water (2 ml) and diluted with EtOAc (20 ml), which was washed with saturated aqueous NaHCO$_3$ (20 ml). Using dilute HCl, the aqueous phase was acidified to pH 2 and the precipitate extracted into EtOAc (50 ml). The organic phase was dried (MgSO$_4$), evaporated and the residue was purified by flash chromatography (5% AcOH in IH-EtOAc, 7:3 to 1:1) to afford the title acid: RT=2.89 min; m/z (ES$^+$)=260.3 [M+H]$^+$.

Preparation 2:
2-Chloro-N-hydroxyisonicotintamidine

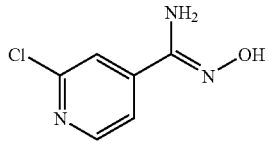

A solution of sodium carbonate (382 mg, 3.61 mmol) and ammonium hydroxide hydrochloride salt (502 mg, 7.22 mmol) in water (10 ml) was added to 2-chloro-4-cyanopyridine (1.0 g, 7.22 mmol) and the mixture heated to 80° C. Sufficient ethanol (10 ml) was then added to give a homogeneous solution. After 18 h, the solution was cooled and the ethanol removed in vacuo. The solid precipitate was collected by filtration, washed with ethanol and CH$_2$Cl$_2$ then dried, affording the title compound: RT=0.86 min; m/z (ES$^+$)=172.1 [M+H]$^+$.

Preparation 3: trans-4-(3-Pyridinyl-[1,2,4]oxadiazol-5-yl)cyclohexanecarboxylic acid methyl ester

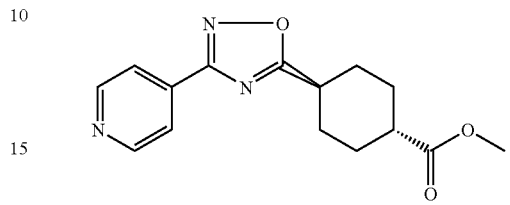

A solution of cyclohexane-1,4-dicarboxylic acid monomethyl ester (1.053 g, 5.66 mmol) and triethylamine (800 µl, 5.66 mmol) in toluene (30 ml) was cooled to 0° C. and isobutylchloroformate (735 µl, 5.66 mmol) introduced dropwise. The mixture was stirred at rt for 30 min whereupon activated, powdered 3 Å molecular sieves (5 g) and N-hydroxyisonicotinamidine (705 mg, 5.14 mmol) were added. The mixture was heated under reflux for 18 h, cooled and filtered through celite. The solvent was removed in vacuo and the residue purified by flash chromatography (IH-EtOAc, 1:1) to afford the title compound: RT=3.20 min; m/z (ES$^-$) =288.2 [M+H]$^+$.

Preparation 4: trans-4-(3-Pyridin-4-yl-[1,2,4]oxadiazol-5-yl)cyclohexanecarboxylic acid

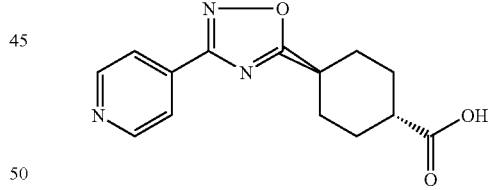

Water (0.5 ml) and lithium hydroxide (9.2 mg, 0.22 mmol) were added to a stirred solution of 4-(3-pyridin-4-yl-[1,2,4] oxadiazol-5-yl)cyclohexanecarboxylic acid methyl ester (Preparation 3, 30 mg, 104 µmol) in THF (1.5 ml). The mixture was heated at 60° C. for 1.5 h, cooled and the THF removed in vacuo. Water (5 ml) was added, the aqueous washed with EtOAc (5 ml) and carefully acidified with 1M HCl to pH 4. The resulting precipitate was extracted into 3% MeOH in EtOAc (2×15 ml) and the combined organic phases dried (MgSO₄) and evaporated to afford the title compound: RT=2.74 min, m/z (ES⁺)=274.2 [M+H]⁺.

Preparation 5: cis-[3-(3-Pyridin 4-yl-[1,2,4]oxadiazol-5-yl)cyclopentyl]methanol

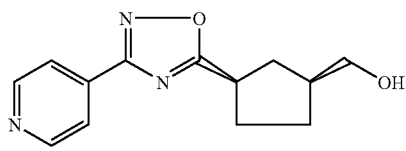

Sodium hydride (10 mg of a 60% dispersion in oil, 2.5 mmol) was added to a solution of N-hydroxyisonicotinamidine (344 mg, 2.5 mmol) in anhydrous THF (3 ml) and the mixture heated under reflux for 1 h. cis-Methyl-3-hydroxymethylcyclopentane-1-carboxylate (396 mg, 2.5 mmol) was added in one portion and heating was continued for 18 h. After cooling, the solution was filtered through celite and the filtrate concentrated in vacuo. The residue was purified by flash chromatography (IH-EtOAc, 1:1 to 0:1) to afford the title compound: RT=2.59 min, m/z (ES⁺)=246.1 [M+H]⁺.

Preparation 6: trans-4-(3-Pyridin-4-yl-[2,4]oxadiazol-5-yl)cyclohexylmethanol

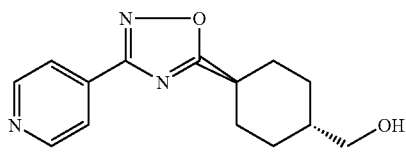

A solution of trans-4-(3-pyridin-4-yl-[1,2,4]oxadiazol-5-yl)cyclohexanecarboxylic acid methyl ester (Preparation 3, 200 mg, 0.696 mmol) in dry CH₂Cl₂ (13 ml) was cooled to −30° C. and diisobutylaluminum hydride (1.59 ml of a 1M solution in toluene, 1.59 mmol) introduced dropwise. After 30 min the reaction was quenched with 2M HCl (6 ml), the mixture warmed to rt and partitioned between 2M HCl (10 ml) and CH₂Cl₂ (10 ml). The aqueous phase was neutralised using 2M NaOH then extracted with CH₂Cl₂ (4×20 ml). The combined organics were dried (MgSO₄) and evaporated to afford the title compound: RT=2.59 min, m/z (ES⁻)=260.2 [M+H]⁺.

Preparation 7: trans-N-Hydroxy-4-pentylcyclohexylamidine

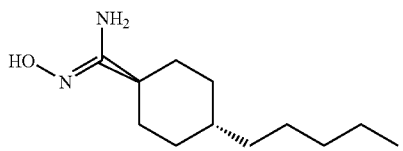

A solution of potassium carbonate (2.49 g, 18 mmol) and NH₂OH.HCl (2.50 g, 36 mmol) in water (15 ml) was added to trans-4-pentylcyclohexanecarbonitrile (4.30 g, 24 mmol) and the mixture heated to 80° C. Sufficient ethanol (approx. 45 ml) was then added to give a homogeneous solution. After 10 h, the solution was cooled, diluted with water (200 ml) and the solid material collected by filtration. The solid was dissolved in EtOAc (150 ml) and the resulting solution washed with brine (50 ml) and dried (MgSO₄). The solvent was reduced in volume to 15 ml and hexane (60 ml) added to precipitate the title compound, which was collected by filtration: RT=2.86 min, m/z (ES⁺)=213.2 [M+H]⁺.

Preparation 8: (3-Pyridin-4-yl-[1,2,4]oxadiazol-5-ylmethyl)carbamic acid tert-butyl ester

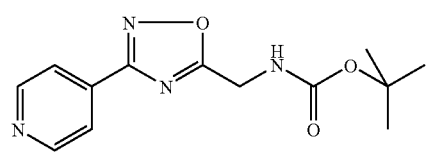

A solution of tert-butoxycarbonylaminoacetic acid (11.0 g, 5.71 mmol) and triethylamine (802 µl, 5.71 mmol) in toluene (30 ml) was cooled to 0° C. and isobutylchloroformate (740 µl, 5.71 mmol) introduced dropwise. The reaction mixture was stirred at 0° C. for 10 min and at rt for 30 min, whereupon N-hydroxyisonicotinamidine (652 mg, 4.76 mmol) and powdered 3 Å molecular sieves (4 g) were added. After heating under reflux for 12 h the reaction was cooled, filtered through celite and the solvent removed in vacuo. The residue was dissolved in EtOAc (200 ml) and washed with water (30 ml) and saturated aqueous NaHCO₃ (30 ml), then dried (MgSO₄). The solvent was removed and the residue purified by flash chromatography (IH-EtOAc, 2:3) to afford the title compound: RT=2.97 min; m/z (ES⁺)=277.1 [M+H]⁺.

Preparation 9: C-(3-Pyridin-4-yl-[1,2,4]oxadiazol-5-yl)methylamine

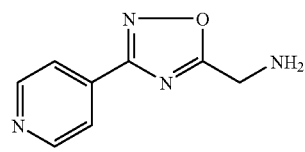

Trifluoroacetic acid (6.5 ml) was added to a solution of (3-pyridin-4-yl-[1,2,4]oxadiazol-5-ylmethyl)carbamic acid tert-butyl ester (Preparation 8, 420 mg, 1.52 mmol in CH₂Cl₂ (10 ml) and the mixture stirred at rt for 2 h. The solvent was evaporated and the residue dissolved in EtOAc (100 ml). After washing with saturated aqueous Na₂CO₃ (25 ml), the aqueous phase was re-extracted with 5% MeOH in CH₂Cl₂ (7×25 ml) and the combined organic phases dried (MgSO₄).

The solvent was removed to afford the title compound: RT=0.25 min; m/z (ES⁺)=177.1 [M+H]⁺.

Preparation 10:
3-Pyridin-4-yl-[1,2,4]oxadiazol-5-ylmethylcarbonic acid isobutyl ester

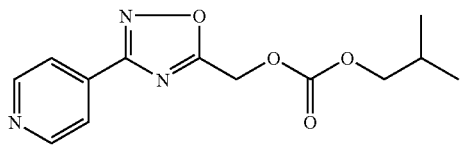

Isobutylchloroformate (11.67 ml, 90 mmol) was added to a solution of hydroxyacetic acid (3.42 g, 45 mmol) and triethylamine (12.65 ml, 90 mmol) in toluene (220 ml) at 0° C. After string at rt for 1 h, N-hydroxyisonicotinamidine (6.17 g, 45 mmol) and powdered 3 Å molecular sieves (20 g) were added. After heating under reflux for 18 h, the cooled mixture was filtered through celite, the solvent evaporated and the residue purified by flash chromatography (IH-EtOAc, 1:1) to afford the title compound: RT=3.51 min; m/z (ES⁺)=278.0 [M+H]⁺.

Preparation 11:
(3-Pyridin-4-yl-[1,2,4]oxadiazol-5-yl)methanol

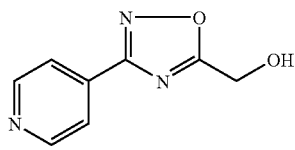

A stirred solution of 3-pyridin-4-yl-[1,2,4]oxadiazol-5-ylmethylcarbonic acid isobutyl ester (Preparation 10, 5.94 g, 21.45 mmol) in methanol (75 ml) at rt was treated with 2M aqueous sodium hydroxide (11.8 ml, 23.6 mmol). After 10 min the solvent was removed and the residue purified by flash chromatography (EtOAc) to afford the title compound: RT=1.30 min; m/z (ES⁺))=178.0 [M+H]⁺.

Preparation 12: Methanesulfonic acid 3-pyridin-4-yl-[1,2,4]oxadiazol-5-ylmethyl ester

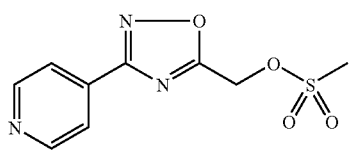

Methanesulfonyl chloride (0.50 ml, 6.50 mmol) was added to a stirred solution of (3-pyridin-4-yl-[1,2,4]oxadiazol-5-yl) methanol (1 g, 5.65 mmol) and triethylamine (0.953 ml, 6.78 mmol) in CH₂Cl₂ (30 ml) at 0° C. After 10 min, water (20 ml) was added and the aqueous phase extracted with CH₂Cl₂ (20 ml). The combined organic phases were dried (MgSO₄) and evaporated to afford the title compound: RT=2.32 min; m/z (ES⁺)=256.0 [M+H]⁺.

Preparation 13:
4-Carbamoylmethoxypiperidine-1-carboxylic acid tert-butyl ester

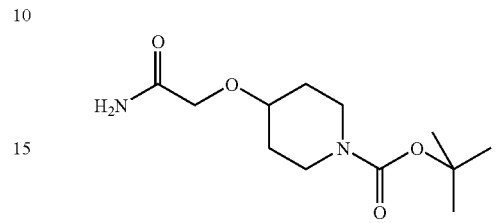

A solution of 4-carboxymethoxypiperidine-1-carboxylic acid tert-butyl ester (Preparation 1, 14.13 g, 54.7 mmol) and triethylamine (7.68 ml, 65.6 mmol) in anhydrous THF (250 ml) was cooled to 0° C. and isobutylchloroformate (8.51 ml, 65.6 mmol) introduced dropwise. After stirring at 0° C. for 30 min, the reaction mixture was cooled to −20° C. and added rapidly via cannula to a solution of 0.7M ammonia in anhydrous CH₂Cl₂ (250 ml, 180 mmol) at −70° C. The reaction was allowed to warm to rt and stirred for 1 h. The mixture was diluted with CH₂Cl₂ (250 ml) and washed with saturated aqueous NaHCO₃ (200 ml), 0.5M HCl (200 ml) and brine (200 ml) then dried (MgSO₄). The solvent was evaporated and the residue purified by flash chromatography IH-THF 3:7) to afford the title compound: $\delta_H$ (CDCl₃) 1.49 (9H, s), 1.53-1.60 (2H, m), 1.85-1.92 (2H, m), 3.11 (2H, m), 3.58 (1H, m), 3.76-3.83 (2H, m), 3.98 (2H, s), 6.19 (1H, bs), 6.56 (1H, bs).

Preparation 14:
4-Cyanomethoxypiperidine-1-carboxylic acid tert-butyl ester

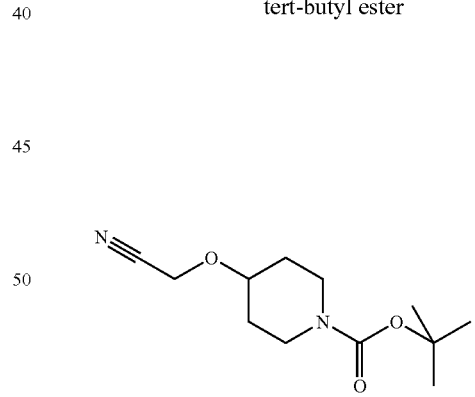

A solution of 4-carbamoylmethoxypiperidine-1-carboxylic acid tert-butyl ester (Preparation 13, 235 mg, 0.91 mmol) and triethylamine (140 μl, 1 mmol) in anhydrous CH₂Cl₂ (5 ml) was cooled to 0° C. and a solution of trichloroacetyl chloride (174 mg, 0.96 mmol) in anhydrous CH₂Cl₂ added dropwise. The reaction mixture was stirred at rt for 1 h, the solvent was removed and the residue purified by flash chromatography (IH-EtOAc, 1:1) to afford the title compound: $\delta_H$ (CDCl$_3$) 1.50 (9H, s), 1.58-1.65 (2H, m), 1.89-1.95 (2H, m), 3.20 (2H, m), 3.74-3.79 (3H, m), 4.33 (2H, s).

Preparation 15: 4-(N-Hydroxycarbamimidoyl-methoxy)piperidine-1-carboxylic acid tert-butyl ester

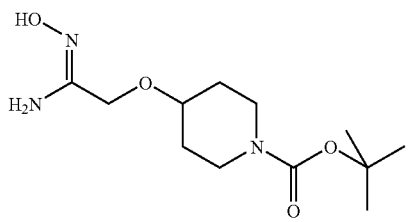

A solution of potassium carbonate (119 mg, 0.86 mmol) and NH$_2$OH.HCl (119 mg, 1.71 mmol) in water (0.5 ml) was added to 4-cyanomethoxypiperidine-1-carboxylic acid tert-butyl ester (Preparation 14, 206 mg, 0.857 mmol) in ethanol (2 ml). The mixture was heated at 75° C. for 0.75 h, cooled and the ethanol evaporated. The residue was diluted with EtOAc (50 ml) and washed with water (2×10 ml) and brine (10 ml) then dried (MgSO$_4$). The solvent was removed to afford the title compound: δ$_H$(CDCl$_3$) 1.50 (9H, s), 1.50-1.60 (2H, m), 1.85-1.92 (2H, m), 3.13 (2H, m), 3.56 (1H, m), 3.77-3.84 (2H, m), 4.05 (2H, s), 4.82 (2H, bs); RT=2.70 min, m/z (ES$^+$)=274.0 [M+H]$^+$.

Preparation 16: 4-{2-Oxo-2-[N'-(pyridine-4-carbonyl)hydrazino]ethoxy}piperidine-1-carboxylic acid tert-butyl ester

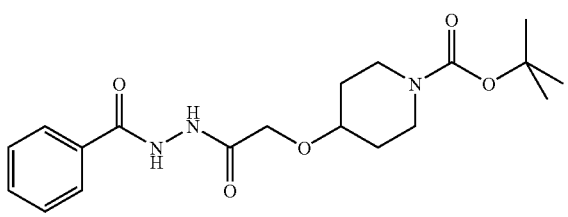

A solution of 4-carboxymethoxypiperidine-1-carboxylic acid tert-butyl ester (Preparation 1, 1.25 g, 4.82 mmol), ethyl-(3-dimethylaminopropyl)carbodiimide (924 mg, 4.82 mmol) and N-hydroxybenzotriazole (651 mg, 4.82 mmol) in anhydrous CH$_2$Cl$_2$ (30 ml) were stirred at rt for 10 min. Isonicotinic acid hydrazide (601 mg, 4.38 mmol) was added in one portion and stirring continued for a further 18 h. The reaction mixture was diluted with CH$_2$Cl$_2$ (150 ml) and washed with water (30 ml), saturated aqueous NaHCO$_3$ (30 ml) and brine (30 ml). After drying (MgSO$_4$) the solvent was removed to afford the title compound: RT=2.89 min; m/z (ES$^+$)=379.1 [M+H]$^+$.

Preparation 17: 4-[5-(Piperidin-4-yloxymethyl)-[1,2,4]oxadiazol-3-yl]pyridine

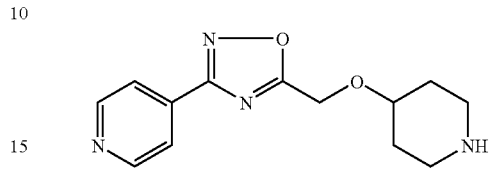

The tert-butoxycarbonyl group of 4-(3-pyridin-4-yl-[1,2,4]oxadiazol-5-ylmethoxy)piperidine-1-carboxylic acid tert-butyl ester (Example 1) was removed using the procedure described in Example 51, affording the title compound: RT=1.84 min; m/z (ES$^+$)=261.2 [M+H]$^+$.

Preparation 18: 4-Thiocarbamoylmethoxypiperidine-1-carboxylic acid tert-butyl ester

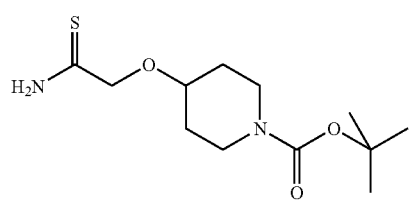

A solution of 4-carbamoylmethoxypiperidine-1-carboxylic acid tert-butyl ester (Preparation 13, 67.5 mg, 260 µmol) and Lawesson's reagent (116 mg, 287 µmol) in dimethoxyethane (1.5 ml) was stirred at rt for 24 h. The solvent was evaporated and the residue purified by flash chromatography (5% MeOH in CH$_2$Cl$_2$) to afford the title compound: δ$_H$ (CDCl$_3$) 1.50 (9H, s), 1.55-1.63 (2H, m), 1.88-1.95 (2H, m), 3.12 (2H, ddd), 3.59-3.66 (1H, m), 3.79-3.87 (2H, m), 4.40, (2H, s), 7.65 (1H, bs), 8.04 (1H, bs).

Preparation 19: trans 4 Pentyl-cyclohexanecarboxylic acid N'-(pyridine-4-carbonyl)hydrazide

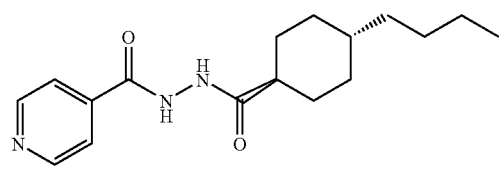

Isonicotinic acid hydrazide was reacted with 4-pentylcyclohexane carboxylic acid in a similar fashion to that

Preparation 20: 3-(2-Cyanopyridin-4-yl)propionic acid

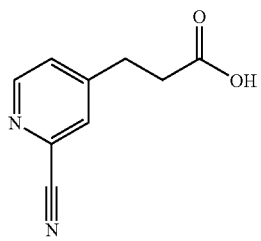

A solution of $K_2CO_3$ (1.67 g, 12.1 mmol) in $H_2O$ (30 ml) was added to a stirred solution of 3-(2-cyanopyridin-4-yl)propyl acetate (4.94 g, 24.2 mmol) in MeOH (130 ml). After 25 min, the MeOH was removed under reduced pressure, then the aqueous phase was extracted three times with EtOAc. The combined organic extracts were dried ($MgSO_4$), filtered, and concentrated to give a residue that was purified by column chromatography (IH-EtOAc, 1:3) to furnish 4-(3-hydroxypropyl)pyridine-2-carbonitrile: m/z ($ES^+$)=163.1 $[M+H]^+$. A solution of this alcohol (500 mg, 3.1 mmol) in DMF (20 ml) was treated with PDC (7 g, 18.6 mmol) and $H_2O$ (0.5 ml). The reaction was stirred for 16 h, before being partitioned between $H_2O$ and EtOAc. The aqueous phase was extracted twice with EtOAc, then the combined organic extracts were washed with brine, before being dried ($MgSO_4$), filtered, and concentrated to give the title compound: m/z ($ES^-$)=177.0 $[M+H]^+$.

Preparation 21: 4-(3-Aminomethyl-[1,2,4]oxadiazol-5-yl)pyridine-2-carbonitrile

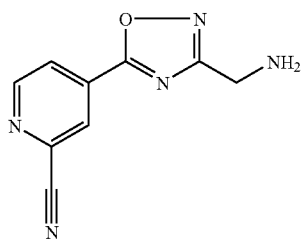

$NEt_3$ (6.6 ml, 47.3 mmol) was added to a stirred solution of 2-cyanoisonicotinic acid (7.00 g, 47.3 mmol) in toluene (500 ml). The mixture was cooled to 0° C., before being treated with isobutyl chloroformate (6.1 ml, 47.3 mmol). Stirring was continued at 0° C. for 10 min, then the mixture was allowed to warm to rt over 1 h, before being treated with (N-hydroxycarbamimidoylmethyl)carbamic acid tert-butyl ester (7.44 g, 39.4 mmol) and dried 4 Å molecular sieves (40 g). The reaction was heated under reflux for 16 h. On cooling, the mixture was filtered through celite, washing with MeOH. The combined filtrates were concentrated in vacuo, then the residue was dissolved in EtOAc. The EtOAc solution was washed with saturated aqueous $Na_2CO_3$ and brine, before being dried ($MgSO_4$). Filtration, solvent evaporation, and column chromatography (IH-EtOAc, 7:3) furnished [5-(2-cyanopyridin-4-yl)-[1,2,4]oxadiazol-3-ylmethyl]carbamic acid tert-butyl ester m/z ($ES^+$)=603.2 $[2M+H]^+$. A stirred solution of this carbamate (1.95 g, 6.5 mmol) in $CHCl_3$ (50 ml) was treated with TMS-I (2.2 ml, 15.6 mmol). After 10 min, the reaction was treated with MeOH (2.5 ml, 62.2 mmol), then stirring was continued for a further 10 min. The solvents were evaporated off under reduced pressure, then the residue was dissolved in MeOH and adsorbed onto $SiO_2$. Column chromatography (EtOAc then EtOAc-MeOH, 9:1) afforded the title compound: m/z ($ES^+$)=202.0 $[M+H]^+$.

Preparation 22: 4-(3,5-Dioxo-5-pyridin-4-ylpentyl)piperidine-1-carboxylic acid tert-butyl ester

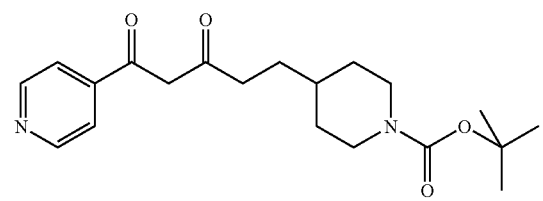

CDI (0.63 g, 3.9 mmol) was added to a solution of 4-(2-carboxyethyl)piperidine-1-carboxylic acid tert-butyl ester (1.00 g, 3.9 mmol) in anhydrous THF (7.6 ml), then the mixture was stirred for 45 min. In a separate vessel, 4-acetylpyridine (0.49 g, 4.1 mmol) was added slowly to a stirred solution of LDA (2.04 ml of a 2.0M solution in heptane-THF-ethylbenzene, 4.1 mmol) in anhydrous THF (15.3 ml) at −78° C. After 45 min, the solution of the acylimidazole was added slowly via cannula to the lithiated 4-acetylpyridine while maintaining the temperature at −78° C. The reaction was allowed to warm to rt over 2 h, before being diluted with EtOAc (150 ml). The solution was washed with 10% aqueous citric acid (2×15 ml), saturated aqueous $NaHCO_3$ (2×15 ml), and brine (20 ml), before being dried ($MgSO_4$). Filtration, concentration, and purification by RP-HPLC afforded the title compound: m/z ($ES^+$)=261.2 $[M-Boc+H]^+$.

Preparation 23: 4-(2,4-Dioxo-4-pyridin-4-ylbutoxy)piperidine-1-carboxylic acid tert-butyl ester

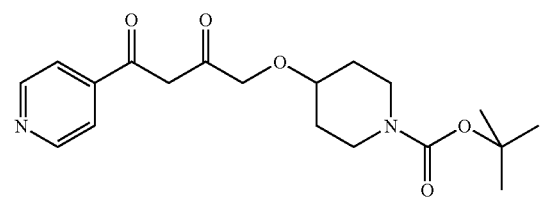

Condensation of 4-acetylpyridine with 4-carboxymethoxypiperidine-1-carboxylic acid tert-butyl ester (Preparation 1), employing the protocol described in Preparation 22, afforded the title compound: m/z (ES+)=263.2 [M-Boc+H]+.

Preparation 24: 4-(2,4-Dioxo-4-pyridin-4-ylbutyl)piperidine-1-carboxylic acid tert-butyl ester

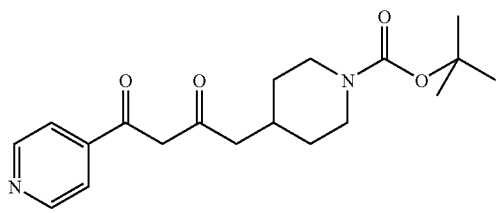

Condensation of 4-acetylpyridine with 4-carboxymethylpiperidine-1-carboxylic acid tert-butyl ester, utilising the protocol described in Preparation 22, afforded the title compound: m/z (ES+)=247.2 [M-Boc+H]+.

Preparation 25: 4-[3-(Piperidin-4-yloxymethyl)-[1,2,4]oxadiazol-5-yl]pyridine-2-carbonitrile

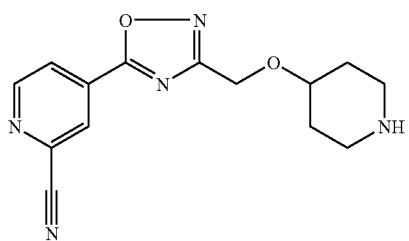

To a stirred solution of 4-[5-(2-cyanopyridin-4-yl)[1,2,4]oxadiazol-3-ylmethoxy]piperidine-1-carboxylic acid tert-butyl ester (Example 42, 2.0 g, 5.2 mmol) in chloroform (100 ml) under argon, was added trimethylsilyl iodide (2.95 ml, 20.8 mmol) and the reaction mixture stirred for 1 h MeOH was added until a solution formed then sodium thiosulphate (6.6 g, 41.5 mmol) was added and the reaction mixture stirred vigorously for 10 min. The solids were removed by filtration and the filtrate adsorbed onto silica gel. Purification via column chromatography (DCM-MeOH, 9:1) afforded the title compound: RT=1.92 min; m/z (ES+)=286.0 [M+H]+.

Example 1

4-(3-Pyridin-yl-[1,2,4]oxadiazol-5-ylmethoxy)piperidine-1-carboxylic acid tert-butyl ester

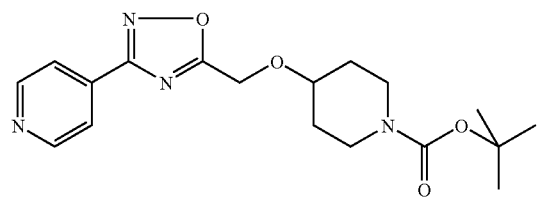

A stirred solution of triethylamine (123 µl, 0.87 mmol) and 4-carboxymethoxypiperidine-1-carboxylic acid tert-butyl ester (Preparation 1, 227 mg, 0.87 mmol) in toluene (10 ml) was treated with isobutylchloroformate (113 µl, 0.87 mmol). After 20 min, activated powdered 3 Å molecular sieves (0.7 g) and N-hydroxyisonicotinamidine (100 mg, 0.73 mmol) were added and the mixture heated under reflux for 18 h. On cooling, the mixture was filtered through celite, the solvent removed in vacuo and the residue purified by flash chromatography (IH-EtOAc, 7:13) to afford the title compound: RT=3.29 min; m/z (ES+) 361.3 [M+H]+; $\delta_H$ (CDCl$_3$) 1.40 (9H, s), 1.55-1.63 (2H, m), 1.80-1.92 (2H, m), 3.05-3.15 (2H, m), 3.64-3.79 (3H, m), 4.80 (2H, s), 7.90 (2H, d), 8.75 (2H, d).

The [1,2,4]oxadiazoles in Table 1 were synthesised from the appropriate amidoxime and the corresponding acid, in a similar manner to that described in Example 1.

TABLE 1

| Ex | Structure | Name | RT (min) | m/z (ES+) |
|---|---|---|---|---|
| 2 | 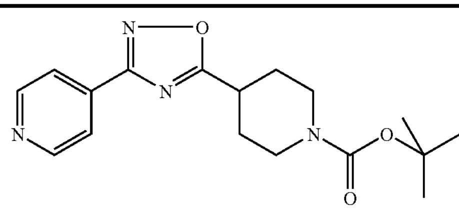 | 4-(3-Pyridin-4-yl-[1,2,4]oxadiazol-5-yl)piperidine-1-carboxylic acid tert-butyl ester | 3.52 | 331.3 [M + H]+ |
| 3 | 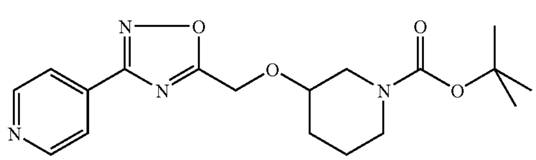 | 3-(3-Pyridin-4-yl-[1,2,4]oxadiazol-5-ylmethoxy)piperidine-1-carboxylic acid tert-butyl ester | 3.29 | 361.3 [M + H]+ |
| 4 | 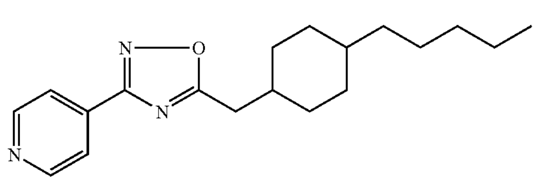 | 4-[5-(4-Pentylcyclohexylmethyl)-[1,2,4]oxadiazol-3-yl]pyridine | 4.97 | 314.3 [M + H]+ |

TABLE 1-continued

| Ex | Structure | Name | RT (min) | m/z (ES+) |
|---|---|---|---|---|
| 5 | 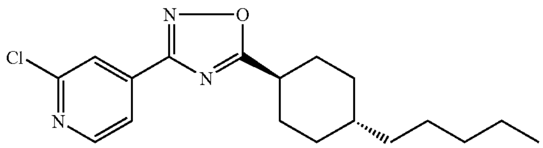 | trans-2-Chloro-4-[5-(4-pentylcyclohexane)-[1,2,4]oxadiazol-3-yl]pyridine | 5.19 | 334.3 [M + H]+ |
| 6 | 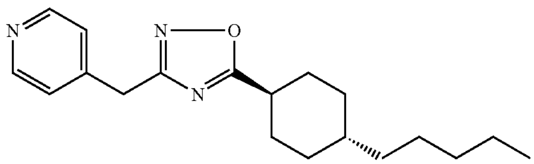 | trans-4-[5-(4-Pentylcyclohexane)-[1,2,4]oxadiazol-3-ylmethyl]pyridine | 3.77 | 314.3 [M + H]+ |
| 7 | 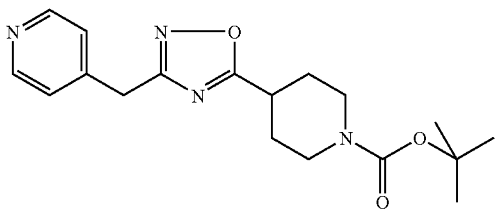 | 4-(3-Pyridin-4-ylmethyl [1,2,4]oxadiazol-5-yl)piperidine-1-carboxylic acid tert-butyl ester | 2.67 | 345.2 [M + H]+ |
| 8 | 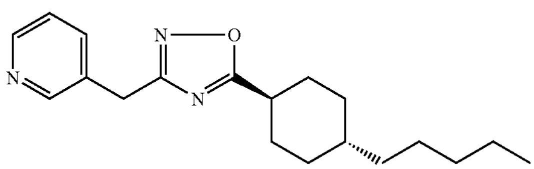 | trans-3-[5-(4-Pentylcyclohexyl)-[1,2,4]oxadiazol-3-ylmethyl]pyridine | 3.92 | 314.3 [M + H]+ |
| 9 | 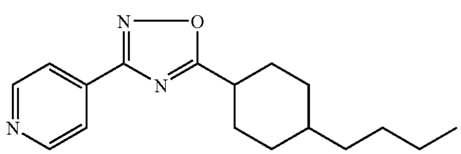 | 4-[5-(4-Butylcyclohexane)-[1,2,4]oxadiazol-3-yl]pyridine | 4.69 | 286.2 [M + H]+ |
| 10 | 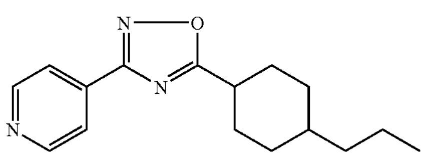 | 4-[5-(4-n-Propylcyclohexyl)-[1,2,4]oxadiazol-3-yl]pyridine | 4.42 | 272.3 [M + H]+ |
| 11 | 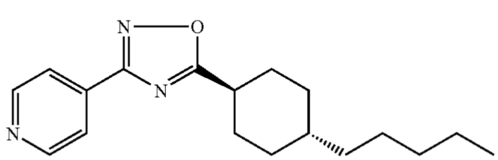 | trans-4-[5-(4-Pentylcyclohexane)-[1,2,4]oxadiazol-3-yl]pyridine | 4.87 | 300.3 [M + H]+ |
| 12 | 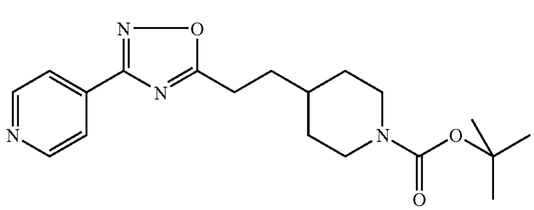 | 4-[2-(3-Pyridin-4-yl-[1,2,4]oxadiazol-5-yl)-ethyl]piperidine-1-carboxylic acid tert-butyl ester | 3.84 | 359.2 [M + H]+ |

TABLE 1-continued

| Ex | Structure | Name | RT (min) | m/z (ES+) |
|---|---|---|---|---|
| 13 | 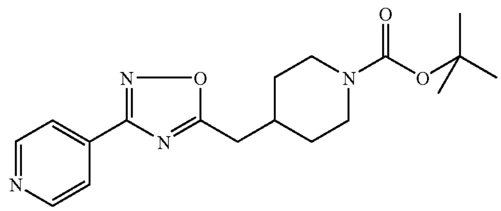 | 4-(3-Pyridin-4-yl-[1,2,4]oxadiazol-5-ylmethyl)piperidine-1-carboxylic acid tert-butyl ester | 3.67 | 345.2 [M + H]+ |

The compounds in Table 2 were also prepared according to the method described in Example 1.

TABLE 2

| Ex | Structure | Name | RT (min) | m/z (ES+) |
|---|---|---|---|---|
| 14 | 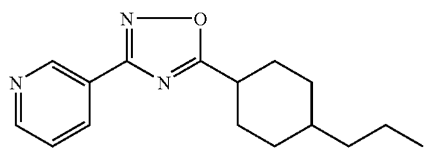 | 3-[5-(4-Propylcyclohexyl)-[1,2,4]oxadiazol-3-yl]pyridine | 4.42 | 272.3 [M + H]+ |
| 15 | 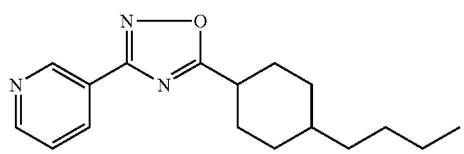 | 3-(5-(4-Butylcyclohexane)-[1,2,4]oxadiazal-3-yl]pyridine | 4.76 | 286.3 [M + H]+ |

Example 16 trans-4-[3-(4-Pentylcyclohexyl)[1,2,4]oxadiazol-5-yl]pyridine-2-carboxylic acid methylamide

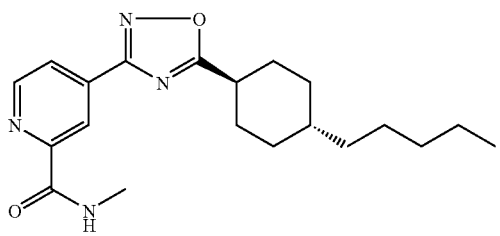

A stirred solution of trans-4-[5-(4-pentylcyclohexane)-[1,2,4]oxadiazol-3-yl]pyridine (Example 11, 100 mg, 0.33 mmol) and $H_2SO_4$ (17.8 μl, 0.33 mmol) in N-methylformamide (2 ml) was cooled to 0° C. Solid $FeSO_4.7H_2O$ (23 mg, 83 μmol) was added followed by $H_2O_2$ (63 μl of a 27% solution in water, 0.5 mmol) and the mixture stirred at 0° C. for 2 h. A solution of 1M aqueous sodium citrate (1 ml) was added and the mixture extracted with $CH_2Cl_2$ (2×5 ml). The combined organic phases were washed with water (2×5 ml), saturated aqueous $NaHCO_3$ (2×5 ml) and brine (5 ml) then dried ($MgSO_4$). The solvent was removed and the residue purified by flash chromatography (IH-EtOAc, 17:3 to 7:3) to afford the title compound: RT=4.86 min, m/z (ES+)=357.4 [M+H]+.

Example 17 trans-4-[5-(4-Pentylcyclohexyl)-[1,2,4]oxadiazol-3-yl]pyridine-2-carboxylic acid amide

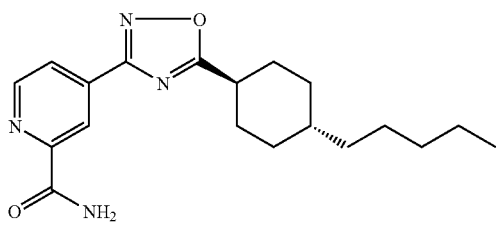

A stirred solution of trans-4-[5-(4-pentylcyclohexane)-[1,2,4]oxadiazol-3-yl]pyridine (Example 11) and $H_2SO_4$ in formamide was treated with $FeSO_4.7H_2O$ and $H_2O_2$ in a similar way to that described in Example 16 to afford the title compound: RT=4.66 min, m/z (ES+)=343.4 [M+]+.

Example 18 trans-4-[3-(4-Pentylcyclohexyl)-[1,2,4]oxadiazol-5-yl]pyridine

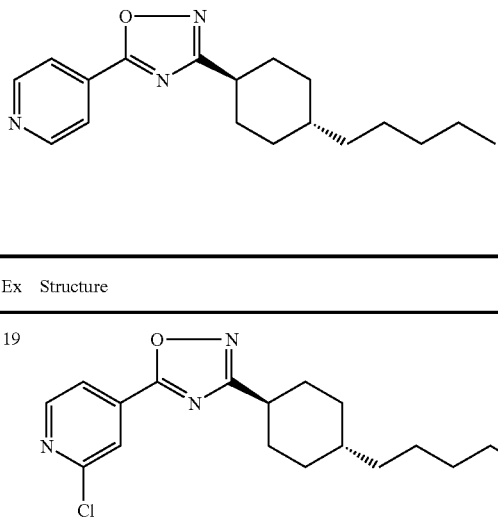

A solution of isonicotinic acid (36.2 mg, 290 μmol) and triethylamine (30 mg, 290 μmol) in anhydrous THF (3 ml) was cooled to 0° C. and isobutylchloroformate (39 mg, 280 μmol) was added. The mixture was stirred at rt for 1 h and solid trans-N-hydroxy-4-pentylcyclohexylamidine (Preparation 7, 50 mg, 235 μmmol) added in one portion. After 45 min the reaction was diluted with EtOAc (12 ml), washed with saturated aqueous NaHCO$_3$ (3 ml) and brine (6 ml), then dried (MgSO$_4$). After evaporation of the solvent, the residue was dissolved in toluene (5 ml) and solution heated under gentle reflux for 2 h. The solvent was removed and the residue purified by flash chromatography (IH-EtOAc, 2:1) to afford the title compound: RT=4.97 min; m/z (ES+)=300.3 [M+H]+.

The [1,2,4]oxadiazoles in Table 3 were synthesized by reacting the appropriate acid with trans-N-hydroxy-4-pentyl-cyclohexylamidine (Preparation 7), in a manner similar to that described in Example 18.

TABLE 3

| Ex | Structure | Name | RT (min) | m/z (ES+) |
|---|---|---|---|---|
| 19 | 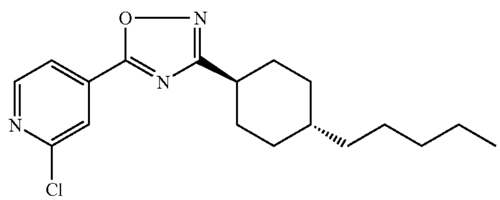 | trans-2-Chloro-4-[3-(4-pentylcyclohexyl)-[1,2,4]oxadiazol-5-yl]pyridine | 5.14 | 334.3 [M + H]+ |
| 20 | 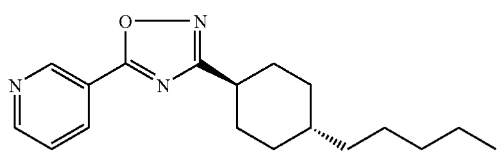 | trans-3-[3-(4-Pentylcyclohexyl)-[1,2,4]oxadiazol-5-yl]pyridine | 5.11 | 300.3 [M + H]+ |
| 21 | 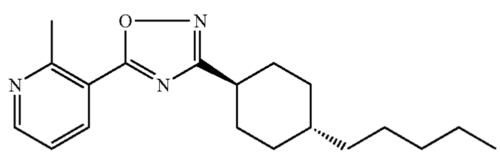 | trans-2-Methyl-3-[3-(4-pentylcyclohexyl)-[1,2,4]oxadiazol-5-yl]pyridine | 4.92 | 314.3 [M + H]+ |
| 22 | 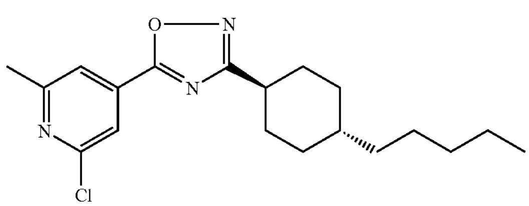 | trans-2-Chloro-6-methyl-4-[3-(4-pentylcyclohexyl)-[1,2 4]oxadiazol-5-yl]-pyridine | 5.39 | 348.3 [M + H]+ |
| 23 | 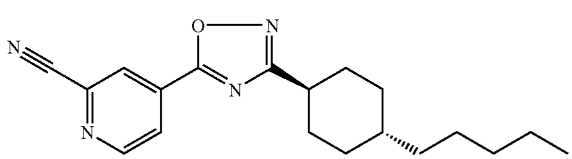 | trans-4-[3-(4-Pentylcyclohexyl)-[1,2,4]oxadiazol-5-yl]pyridine-2-carbonitrile | 4.91 | 366.4 [M + H + CH$_3$CN]+ |
| 24 | 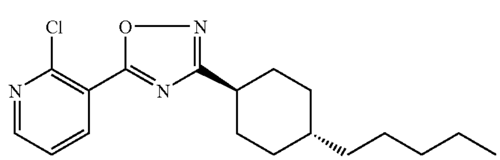 | trans-2-Chloro-3-[3-(4-pentylcyclohexyl)-[1,2,4]oxadiazol-5-yl]pyridine | 4.99 | 334.3 [M + H]+ |

TABLE 3-continued

| Ex | Structure | Name | RT (min) | m/z (ES+) |
|---|---|---|---|---|
| 25 | 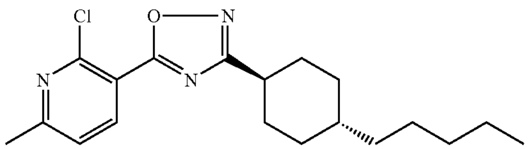 | trans-2-Chloro-6-methyl-3-[3-(4-pentylcyclohexyl)-[1,2,4]oxadiazol-5-yl]pyridine | 5.34 | 348.3 [M + H]+ |
| 26 | 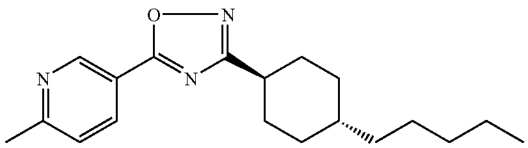 | trans-2-Methyl-5-[3-(4-pentylcyclohexyl)-[1,2,4]oxadiazol-5-yl]pyridine | 4.80 | 314.3 [M + H]+ |
| 27 | 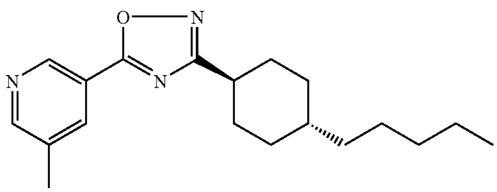 | trans-3-Methyl-5-[3-(4-pentylcyclohexyl)-[1,2,4]oxadiazol-5-yl]pyridine | 4.94 | 314.3 [M + H]+ |
| 28 | 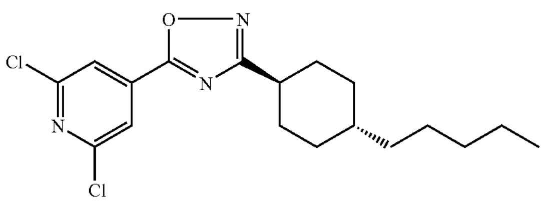 | trans-2,6-Dichloro-4-[3-(4-pentylcyclohexyl)-[1,2,4]oxadiazol-5-yl]pyridine | 5.37 | 368.3 [M + H]+ |
| 29 | 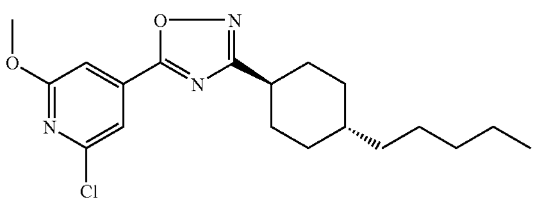 | trans-2-Chloro-6-methoxy-4-[3-(4-pentylcyclohexyl)-[1,2,4]oxadiazol-5-yl]pyridine | 5.44 | 364.3 [M + H]+ |
| 30 | 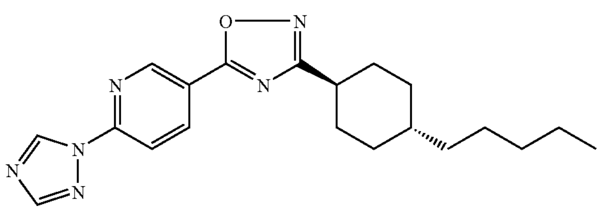 | trans-5-[3-(4-Pentylcyclohexyl)-[1,2,4]oxadiazol-5-yl]-2-[1,2,4]triazol-1-ylpyridine | 5.36 | 367.4 [M + H]+ |
| 31 | 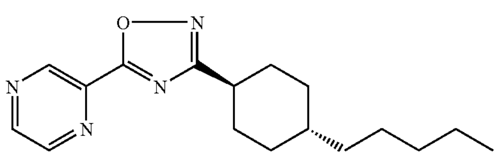 | 2-[3-(4-Pentylcyclohexyl)-[1,2,4]oxadiazol-5-yl]pyrazine | 4.72 | 301.2 [M + H]+ |
| 32 | 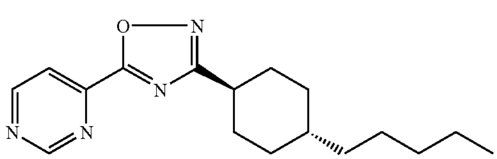 | 4-[3-(4-Pentylcyclohexyl)-[1,2,4]oxadiazol-5-yl]pyrimidine | 4.86 | 301.2 [M + H]+ |

TABLE 3-continued

| Ex | Structure | Name | RT (min) | m/z (ES+) |
|---|---|---|---|---|
| 33 | 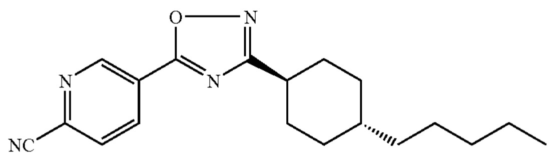 | trans-5-[3-(4-Pentylcyclohexyl)-[1,2,4]oxadiazol-5-yl]pyridine-2-carbonitrile | 5.16 | 325.2 [M + H]+ |
| 34 | 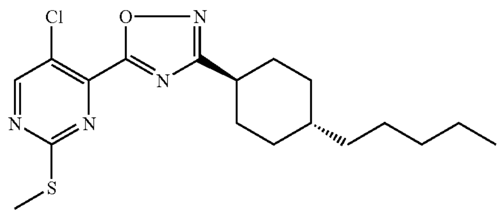 | trans-5-Chloro-2-methylsulfanyl-4-[3-(4-pentylcyclohexyl)-[1,2,4]oxadiazol-5-yl]pyrimidine | 5.32 | 381.1 [M + H]+ |
| 35 | 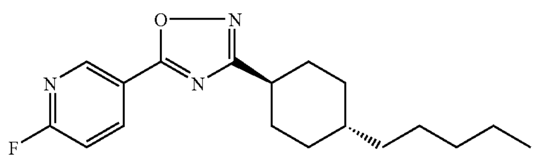 | trans-2-Fluoro-5-[3-(4-pentylcyclohexyl)-[1,2,4]oxadiazol-5-yl]pyrimidine | 5.12 | 318.2 [M + H]+ |
| 36 | 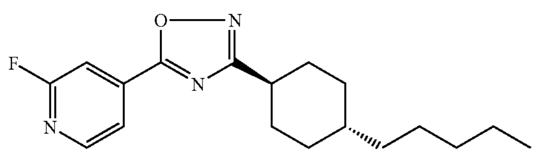 | trans-2-Fluoro-4-[3-(4-pentylcyclohexyl)-[1,2,4]oxadiazol-5-yl]pyridine | 5.07 | 318.2 [M + H]+ |
| 37 | 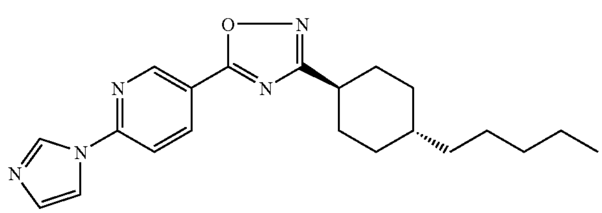 | trans-2-Imidazol-1-yl-5-[3-(4-pentylcyclohexyl)-[1,2,4]oxadiazol-5-yl]pyridine | 4.49 | 366.2 [M + H]+ |
| 38 | 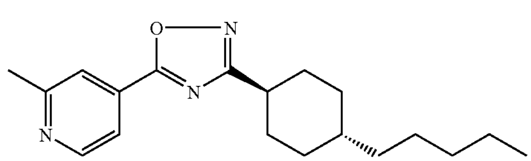 | trans-2-Methyl-4-[3-(4-pentylcyclohexyl)-[1,2,4]oxadiazol-5-yl]pyridine | 5.05 | 314.2 [M + H]+ |
| 39 | 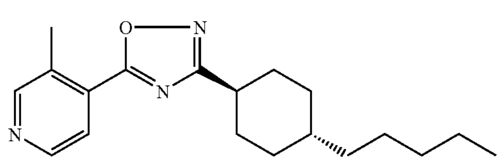 | trans-3-Methyl-4-[3-(4-pentylcyclohexyl)-[1,2,4]oxadiazol-5-yl]pyridine | 5.16 | 314.2 [M + H]+ |
| 40 | 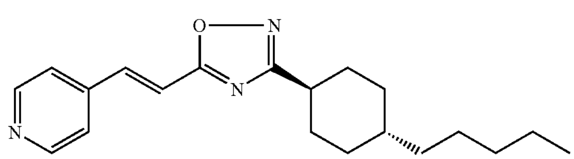 | trans-4-{2-[3-(4-Pentylcyclohexyl)-[1,2,4]oxadiazol-5-yl]vinyl}pyridine | 4.62 | 326.2 [M + H]+ |

Example 41

4-(5-Pyridin-4-yl-[1,2,4]oxadiazol-3-ylmethoxy) piperidine-1-carboxylic acid tert-butyl ester

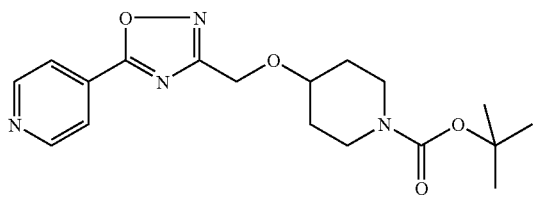

A solution of isonicotinic acid (31 mg, 250 µmol) and triethylamine (51 mg, 500 µmol) in anhydrous THF was cooled to 0° C. and isobutylchloroformate (34 mg, 250 µmol) was added. The reaction was stirred at rt for 0.5 h and solid 4-(N-hydroxycarbamimidoylmethoxy)piperidine-1-carboxylic acid tert-butyl ester (Preparation 15, 54.5 mg, 200 µmol) added in one portion. After stirring for 40 min the solvent was removed, EtOAc added to the residue, and the mixture passed through a small plug of silica, eluting with EtOAc. Following evaporation, the residue was dissolved in toluene (4 ml) and heated under reflux for 15 h. The solvent was then evaporated and the residue purified by flash chromatography (EtOAc) to afford the title compound: RT=3.65 min, m/z (ES$^+$)=361.2 [M+H]$^+$.

The [1,2,4]oxadiazoles in Table 4 were synthesized by condensing the appropriate acid with a suitable amidoxime, in a manner similar to that described in Example 41.

TABLE 4

| Ex | Structure | Name | RT (min) | m/z (ES$^+$) |
|---|---|---|---|---|
| 42 | 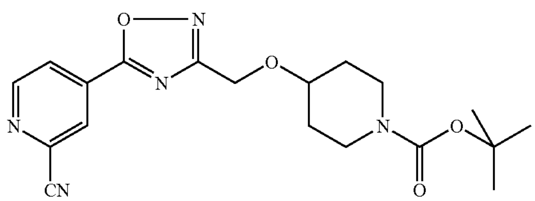 | 4-[5-(2-Cyanopyridin-4-yl)-[1,2,4]oxadiazol-3-ylmethoxy]piperidine-1-carboxylic acid tert-butyl ester | 3.82 | 386.1 [M + H]$^+$ |
| 43 | 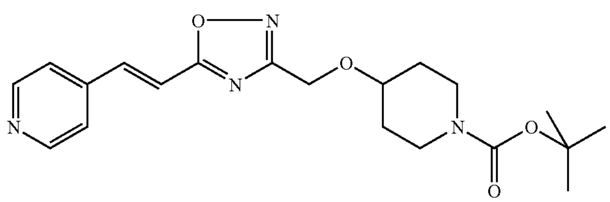 | (E)-4-[5-(2-Pyridin-3-yl-vinyl)-[1,2,4]oxadiazol-3-ylmethoxy]piperidine-1-carboxylic acid tert-butyl ester | 3.49 | 387.2 [M + H]$^+$ |
| 44 | 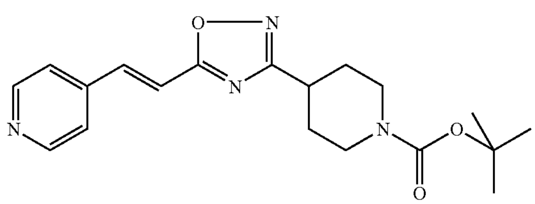 | (E)-4-[5-(2-Pyridin-3-yl-vinyl)-[1,2,4]oxadiazol-3-yl]piperidine-1-carboxylic acid tert-butyl ester | 3.52 | 357.2 [M + H]$^+$ |
| 45 | 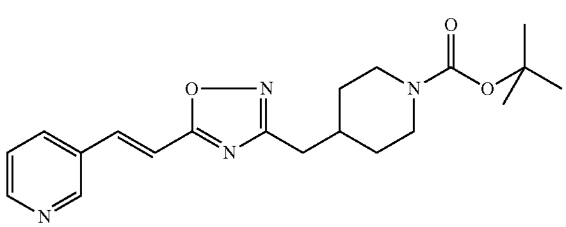 | (E)-4-[5-(2-Pyridin-3-yl-vinyl)-[1,2,4]oxadiazol-3-ylmethyl]piperidine-1-carboxylic acid tert-butyl ester | 3.62 | 271.2 [M − Boc + H]$^+$ |
| 46 | 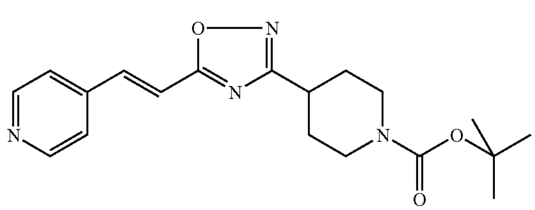 | (E)-4-[5-(2-Pyridin-4-yl-vinyl)-[1,2,4]oxadiazol-3-yl]piperidine-1-carboxylic acid tert-butyl ester | 3.26 | 357.2 [M + H]$^+$ |

TABLE 4-continued

| Ex | Structure | Name | RT (min) | m/z (ES+) |
|---|---|---|---|---|
| 47 | 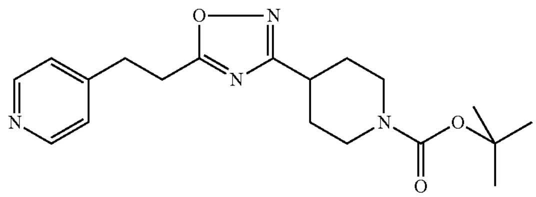 | 4-[5-(2-Pyridin-4-yl-ethyl)-[1,2,4]oxadiazol-3-yl]-piperidine-1-carboxylic acid tert-butyl ester | 2.76 | 359.1 [M + H]+ |
| 48 | 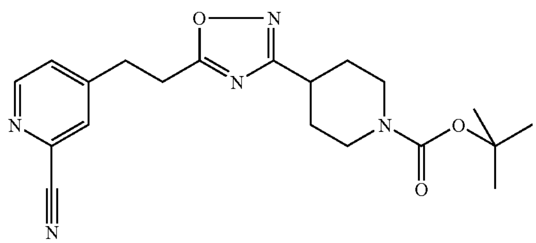 | 4-{5-[2-(2-Cyanopyridin-4-yl)ethyl]-[1,2,4]oxadiazol-3-yl}piperidine-1-carboxylic acid tert-butyl ester | 3.70 | 384.2 [M + H]+ |
| 49 | 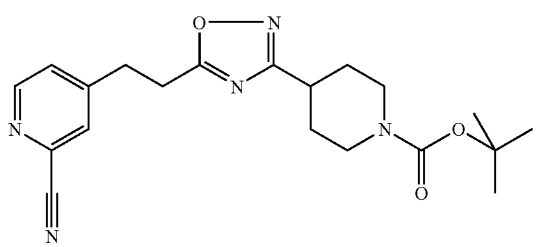 | 4-{5-[2-(2-Cyanopyridin-4-yl)ethyl]-[1,2,4]oxadiazol-3-ylmethoxy}piperidine-1-carboxylic acid tert-butyl ester | 3.74 | 414.2 [M + H]+ |
| 50 | 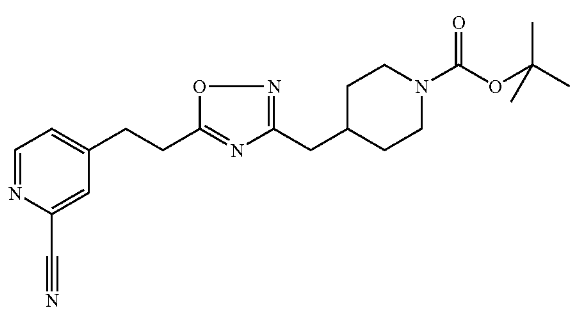 | 4-{5-[2-(2-Cyanopyridin-4-yl)ethyl]-[1,2,4]oxadiazol-3-ylmethyl}piperidine-1-carboxylic acid tert-butyl ester | 3.76 | 398.2 [M + H]+ |

Example 51

4-(5-Piperidin-4-yl-[1,2,4]oxadiazol-3-yl)pyridine

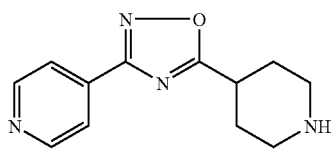

Trifluoroacetic acid (20 ml) was added to a stirred solution of 4-(3-pyridin-4-yl-[1,2,4]oxadiazol-5-yl)piperidine-1-carboxylic acid tert-butyl ester (Example 2, 1.64 g, 4.96 mmol) in $CH_2Cl_2$ (35 ml). After 2.5 h at rt, the solvent was evaporated under reduced pressure. The residual solid was suspended in EtOAc (150 ml) and washed with saturated aqueous $Na_2CO_3$ (20 ml). The aqueous was separated and extracted with EtOAc (3×30 ml). The combined organic extracts were dried ($MgSO_4$) and evaporated under reduced pressure to afford the title compound: RT=3.48 min, m/z ($ES^+$)=231.2 $[M+H]^+$.

Example 52

4-(3-Pyridin-4-yl-[1,2,4]oxadiazol-5-yl)piperidine-1-carboxylic acid isobutyl ester

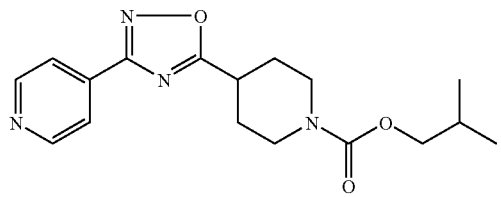

A solution of pyridine (18 μl, 0.22 mmol) and 4-(5-piperidin-4-yl-[1,2,4]oxadiazol-3-yl)pyridine (Example 51, 50 mg, 0.22 mmol) in $CH_2Cl_2$ (4 ml) was treated with isobutylchloroformate (54 mg, 0.43 mmol). The reaction was stirred at rt for 18 h then quenched with saturated aqueous $NaHCO_3$ (1 ml). The organic phase was separated, evaporated and the residue purified by flash chromatography (IH-EtOAc, 1:1 to 0:1) to afford the title compound: RT=3.42 min, m/z ($ES^+$) =331.2 $[M+H]^+$.

The [1,2,4]oxadiazoles in Table 4 were synthesized in a manner similar to that described in Example 52.

TABLE 4

| Ex | Structure | Name | RT (min) | m/z ($ES^+$) |
|----|-----------|------|----------|--------------|
| 53 | 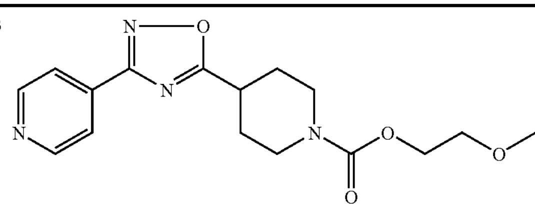 | 4-(3-Pyridin-4-yl-[1,2,4]oxadiazol-5-yl)piperidine-1-carboxylic acid 2-methoxyethyl ester | 2.77 | 333.2 $[M + H]^+$ |
| 54 | 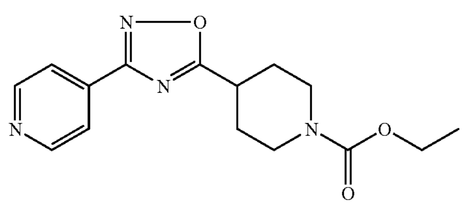 | 4-(3-Pyridin-4-yl-[1,2,4]oxadiazol-5-yl)piperidine-1-carboxylic acid ethyl ester | 3.19 | 303.2 $[M + H]^+$ |

Example 55

3,3-Dimethyl-1-[4-(3-pyridin-4-yl-[1,2,4]oxadiazol-5-yl)piperidin-1-yl]butan-1-one

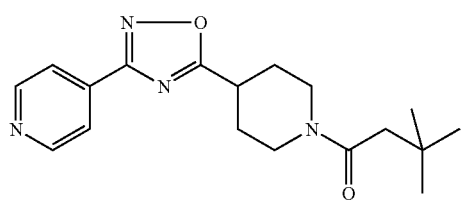

A solution of pyridine (18 μl, 0.22 mmol) and 4-(5-piperidin-4-yl-[1,2,4]oxadiazol-3-yl)pyridine (Example 51, 50 mg, 022 mmol) in $CH_2Cl_2$ (4 ml) was treated with 3,3-dimethylbutanoyl chloride (58 mg, 0.43 mmol). The reaction was stirred at rt for 18 h then quenched with saturated aqueous $NaHCO_3$ (1 ml). The organic phase was separated, evaporated

Example 56

2-Cyclopentyl-1-[4-(3-pyridin-4-yl-[1,2,4]oxadiazol-5-yl)piperidin-1-yl]ethanone

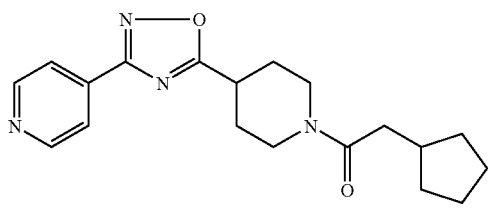

4-[5-(Piperidin-4-yloxymethyl)-[1,2,4]oxadiazol-3-yl]pyridine (Example 51) was reacted with cyclopentylacetyl chloride, in a similar manner to that described in Example 55, to afford the title compound: RT=3.44 min, m/z (ES⁺)=341.3 [M+H]⁺.

Example 57

4-{5-[1-(Butane-1-sulfonyl)piperidin-4-yl]-[1,2,4]oxadiazol-3-yl}pyridine

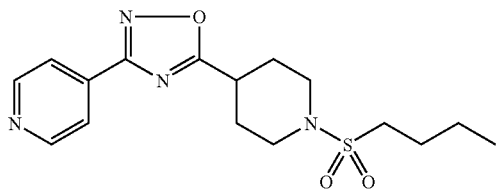

A solution of pyridine (18 µl, 0.22 mmol) and 4-(5-piperidin-4-yl-[1,2,4]oxadiazol-3-yl)pyridine (Example 51, 50 mg, 0.22 mmol) in CH₂Cl₂ (4 ml) was treated with butane-1-sulfonyl chloride (56 µl, 0.43 mmol). The reaction was stirred at rt for 18 h then quenched with saturated aqueous NaHCO₃ (1 ml). The organic phase was separated, dried (MgSO₄) and evaporated. The residue was dissolved in EtOAc (5 ml) and extracted into 2M HCl (10 ml). The aqueous phase was then basified using 2M NaOH to pH=8 and extracted with CH₂Cl₂ (2×10 ml). The combined organic phases were dried (MgSO₄) and evaporated to afford the title compound: RT=3.29 min, m/z (ES⁺)=351.2 [+H]⁺.

Example 58

4-(3-Pyridin-4-yl-[1,2,4]oxadiazol-5-yl)piperidine-1-carboxylic acid propylamide

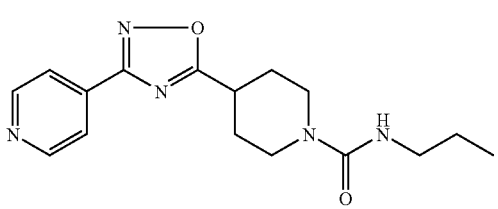

1-Propylisocyanate (13 µl, 137 µmol) was added to a solution of 4-(5-piperidin-4-yl-[1,2,4]oxadiazol-3-yl)pyridine (Example 51, 15.8 mg, 691 mol) in CH₂Cl₂ (0.7 ml). After stirring 18 h at rt, the solvent was removed to afford the title compound: RT=2.72 min; m/z (ES⁺)=316.3 [M+H]⁺.

Example 59

4-(3-Pyridin-4-yl-[2,4]oxadiazol-5-yl)piperidine-1-carboxylic acid tert-butylamide

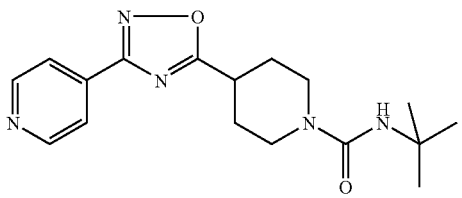

tert-Butylisocyanate was reacted with 4-(5-piperidin-4-yl-[1,2,4]oxadiazol-3-yl)pyridine (Example 51) in a similar fashion to that described in Example 58 to afford the title compound RT=3.04 min; m/z (ES⁺)=330.3 [M+H]⁺.

The carbamate esters in Table 5 were produced by reaction of 4-[5-(piperidin-4-yloxymethyl)[1,2,4]oxadiazol-3-yl]pyridine (Preparation 17) with the appropriate chloroformate, in a fashion similar to that described in Example 52.

TABLE 5

| Ex | Structure | Name | RT (min) | m/z (ES⁺) |
|---|---|---|---|---|
| 60 | 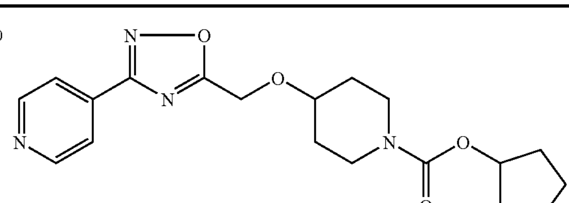 | 4-(3-Pyridin-4-yl-[1,2,4]oxadiazol-5-ylmethoxy)piperidine-1-carboxylic acid cyclopentyl ester | 3.51 | 373.4 [M + H]⁺ |

TABLE 5-continued

| Ex | Structure | Name | RT (min) | m/z (ES+) |
|---|---|---|---|---|
| 61 | 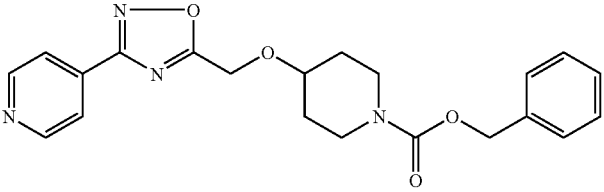 | 4-(3-Pyridin-4-yl-[1,2,4]oxadiazol-5-ylmethoxy)piperidine-1-carboxylic acid benzyl ester | 3.64 | 395.3 [M + H]+ |
| 62 | 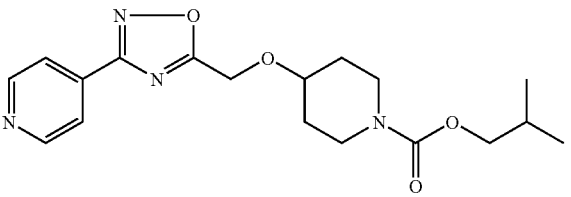 | 4-(3-Pyridin-4-yl-[1,2,4]oxadiazol-5-ylmethoxy)piperidine-1-carboxylic acid isobutyl ester | 3.49 | 361.3 [M + H]+ |
| 63 | 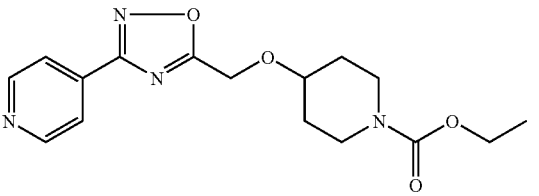 | 4-(3-Pyridin-4-yl-[1,2,4]oxadiazol-5-ylmethoxy)piperidine-1-carboxylic acid ethyl ester | 3.03 | 333.3 [M + H]+ |
| 64 | 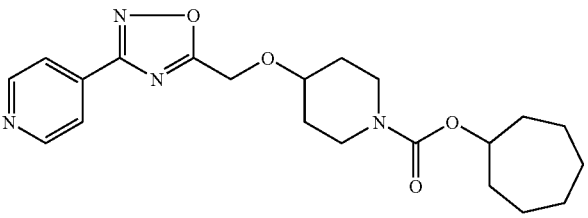 | 4-(3-Pyridin-4-yl-[1,2,4]oxadiazol-5-ylmethoxy)piperidine-1-carboxylic acid cycloheptyl ester | 3.92 | 401.1 [M + H]+ |
| 65 | 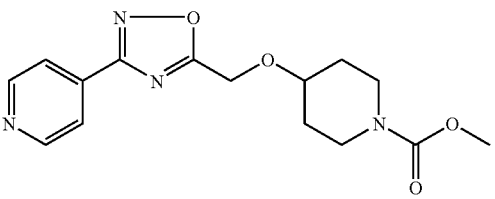 | 4-(3-Pyridin-4-yl-[1,2,4]oxadiazol-5-ylmethoxy)piperidine-1-carboxylic acid methyl ester | 2.86 | 319.3 [M + H]+ |
| 66 | 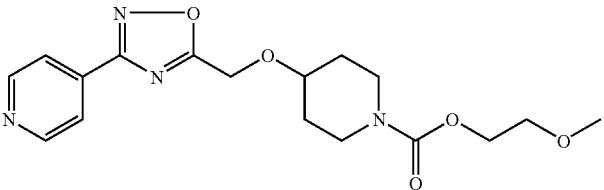 | 4-(3-Pyridin-4-yl-[1,2,4]oxadiazol-5-ylmethoxy)piperidine-1-carboxylic acid 2-methoxy-ethyl ester | 2.95 | 363.2 [M + H]+ |
| 67 | 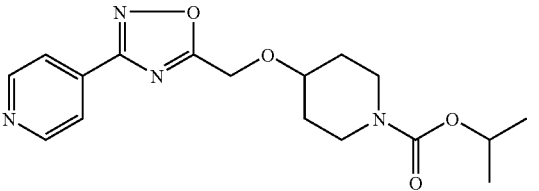 | 4-(3-Pyridin-4-yl-[1,2,4]oxadiazol-5-ylmethoxy)piperidine-1-carboxylic acid isopropyl ester | 3.34 | 347.2 [M + H]+ |

TABLE 5-continued

| Ex | Structure | Name | RT (min) | m/z (ES⁺) |
|---|---|---|---|---|
| 68 | 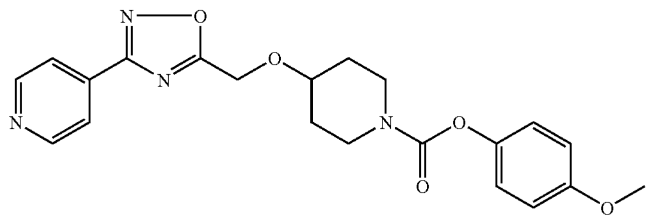 | 4-(3-Pyridin-4-yl-[1,2,4]oxadiazol-5-ylmethoxy)piperidine-1-carboxylic acid 4-methoxyphenyl ester | 3.74 | 411.1 [M + H]⁺ |
| 69 | 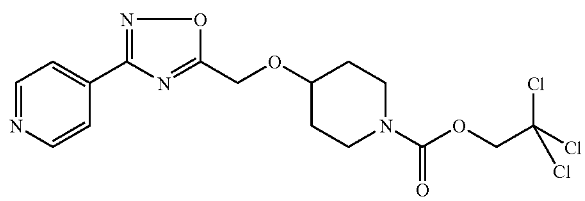 | 4-(3-Pyridin-4-yl-[1,2,4]oxadiazol-5-ylmethoxy)piperidine-1-carboxylic acid 2,2,2-trichloroethyl ester | 3.81 | 434.8 [M + H]⁺ |
| 70 | 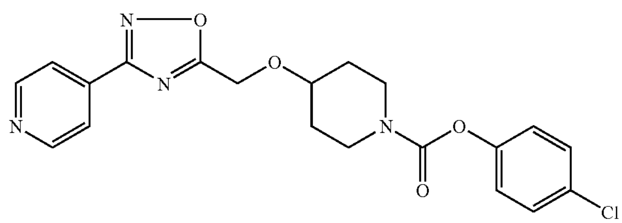 | 4-(3-Pyridin-4-yl-[1,2,4]oxadiazol-5-ylmethoxy)piperidine-1-carboxylic acid 4-chlorophenyl ester | 3.79 | 415.1 [M + H]⁺ |
| 71 | 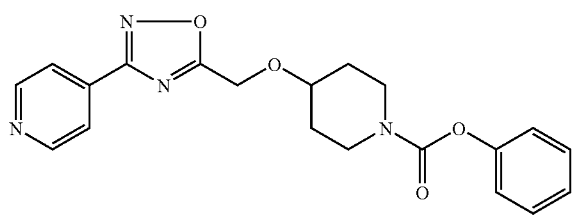 | 4-(3-Pyridin-4-yl-[1,2,4]oxadiazol-5-ylmethoxy)piperidine-1-carboxylic acid phenyl ester | 3.54 | 381.1 [M + H]⁺ |
| 72 | 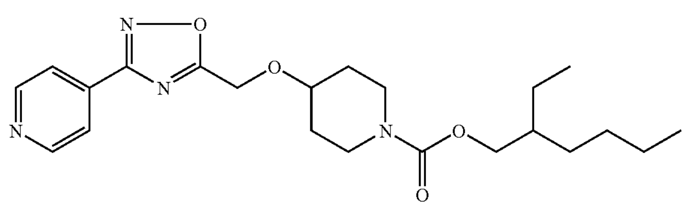 | 4-(3-Pyridin-4-yl-[1,2,4]oxadiazol-5-ylmethoxy)piperidine-1-carboxylic acid 2-ethylhexyl ester | 4.27 | 417.2 [M + H]⁺ |
| 73 | 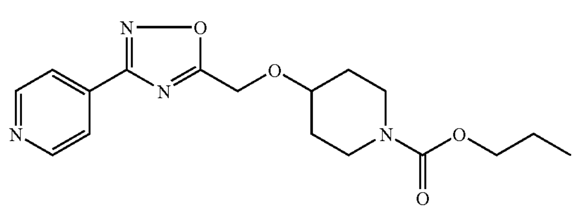 | 4-(3-Pyridin-4-yl-[1,2,4]oxadiazol-5-ylmethoxy)piperidine-1-carboxylic acid propyl ester | 3.40 | 347.1 [M + H]⁺ |
| 74 | 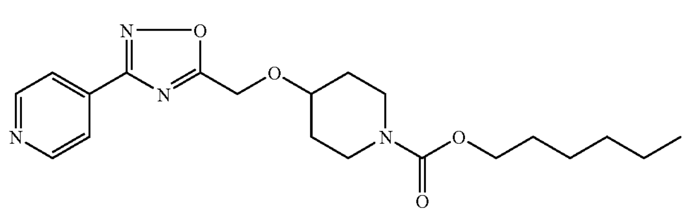 | 4-(3-Pyridin-4-yl-[1,2,4]oxadiazol-5-ylmethoxy)piperidine-1-carboxylic acid hexyl ester | 3.95 | 389.1 [M + H]⁺ |

TABLE 5-continued

| Ex | Structure | Name | RT (min) | m/z (ES+) |
|---|---|---|---|---|
| 75 | 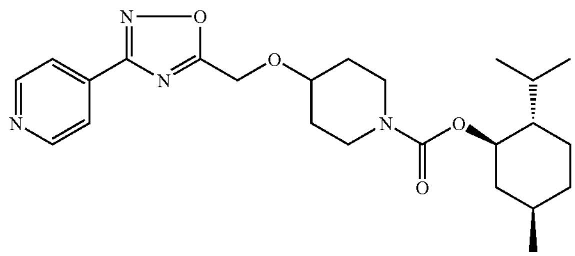 | 4-(3-Pyridin-4-yl-[1,2,4]oxadiazol-5-ylmethoxy)piperidine-1-carboxylic acid (1R,2S,5R)-2-isopropyl-5-methylcyclohexyl ester | 4.44 | 443.2 [M + H]+ |
| 76 | 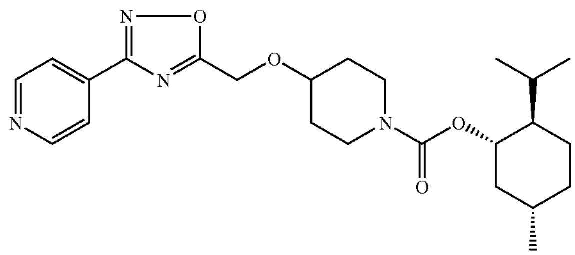 | 4-(3-Pyridin-4-yl-[1,2,4]oxadiazol-5-ylmethoxy)piperidine-1-carboxylic acid (1S,2R,5S)-2-isopropyl-5-methylcyclohexyl ester | 4.39 | 443.2 [M + H]+ |
| 77 | 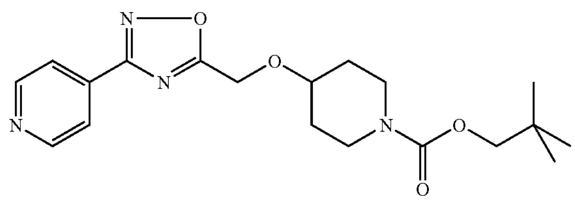 | 4-(3-Pyridin-4-yl-[1,2,4]oxadiazol-5-ylmethoxy)piperidine-1-carboxylic acid 2,2-dimethylpropyl ester | 3.92 | 375.1 [M + H]+ |
| 78 | 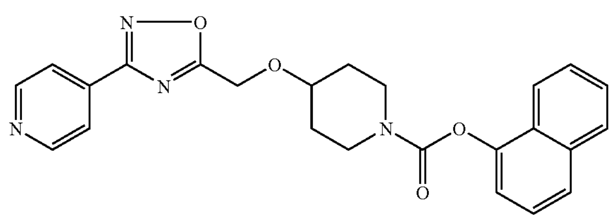 | 4-(3-Pyridin-4-yl-[1,2,4]oxadiazol-5-ylmethoxy)piperidine-1-carboxylic acid naphthalen-1-yl ester | 3.90 | 431.1 [M + H]+ |
| 79 | 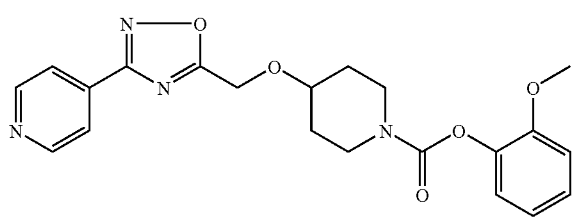 | 4-(3-Pyridin-4-yl-[1,2,4]oxadiazol-5-ylmethoxy)piperidine-1-carboxylic acid 2-methoxy-phenyl ester | 3.67 | 411.1 [M + H]+ |
| 80 | 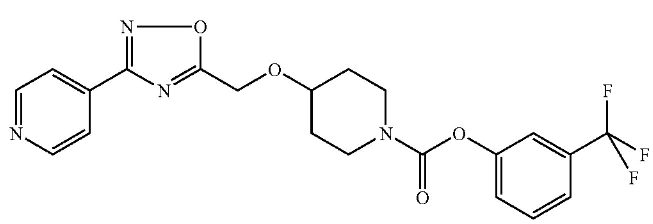 | 4-(3-Pyridin-4-yl-[1,2,4]oxadiazol-5-ylmethoxy)piperidine-1-carboxylic acid 3-trifluoromethylphenyl ester | 3.87 | 449.0 [M + H]+ |
| 81 | 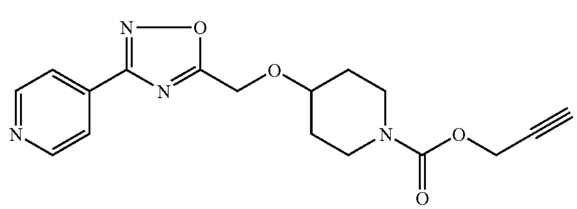 | 4-(3-Pyridin-4-yl-[1,2,4]oxadiazol-5-ylmethoxy)piperidine-1-carboxylic acid prop-2-ynyl ester | 3.36 | 343.1 [M + H]+ |

TABLE 5-continued

| Ex | Structure | Name | RT (min) | m/z (ES+) |
|---|---|---|---|---|
| 82 | 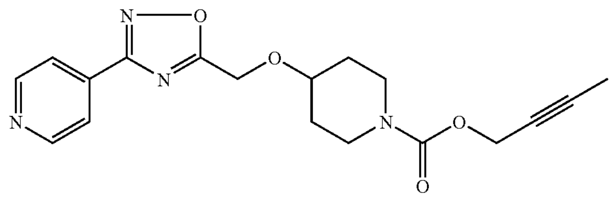 | 4-(3-Pyridin-4-yl-[1,2,4]oxadiazol-5-ylmethoxy)piperidine-1-carboxylic acid but-2-ynyl ester | 3.40 | 357.2 [M + H]+ |
| 83 | 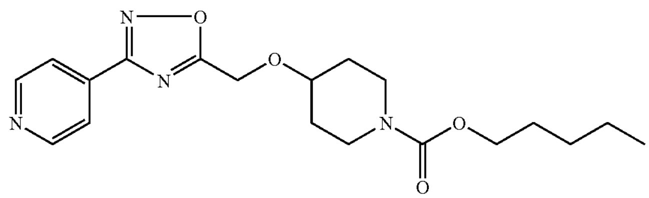 | 4-(3-Pyridin-4-yl-[1,2,4]oxadiazol-5-ylmethoxy)piperidine-1-carboxylic acid pentyl ester | 3.90 | 375.2 [M + H]+ |
| 84 | 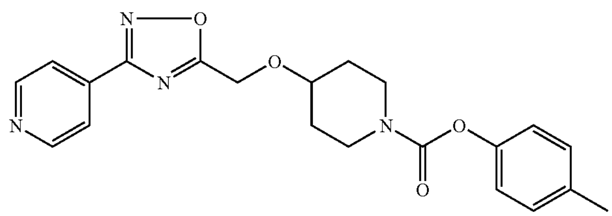 | 4-(3-Pyridin-4-yl-[1,2,4]oxadiazol-5-ylmethoxy)piperidine-1-carboxylic acid p-tolyl ester | 3.72 | 395.2 [M + H]+ |
| 85 | 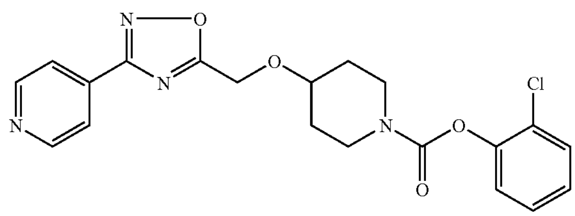 | 4-(3-Pyridin-4-yl-[1,2,4]oxadiazol-5-ylmethoxy)piperidine-1-carboxylic acid 2-chloro-phenyl ester | 3.72 | 415.1 [M + H]+ |
| 86 | 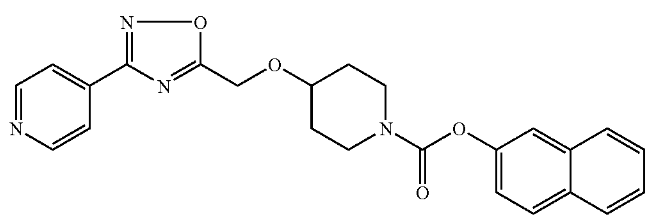 | 4-(3-Pyridin-4-yl-[1,2,4]oxadiazol-5-ylmethoxy)piperidine-1-carboxylic acid naphthalen-2-yl ester | 3.97 | 431.1 [M + H]+ |
| 87 | 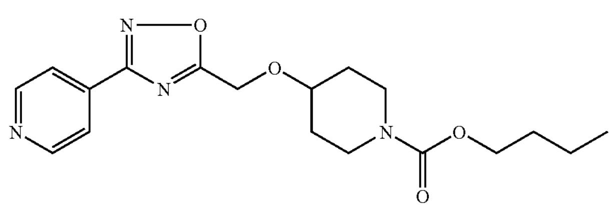 | 4-(3-Pyridin-4-yl-[1,2,4]oxadiazol-5-ylmethoxy)piperidine-1-carboxylic acid butyl ester | 3.86 | 361.1 [M + H]+ |
| 88 | 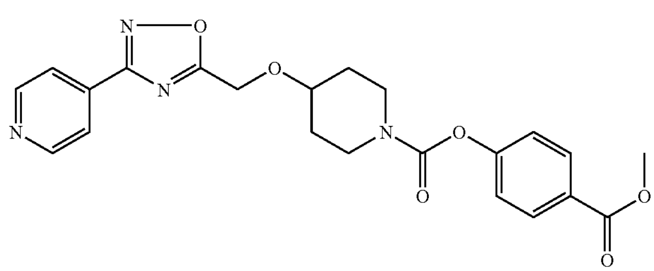 | 4-(3-Pyridin-4-yl-[1,2,4]oxadiazol-5-ylmethoxy)piperidine-1-carboxylic acid 4-methoxycarbonyl-phenyl ester | 4.64 | 438.9 [M + H]+ |

TABLE 5-continued

| Ex | Structure | Name | RT (min) | m/z (ES+) |
|---|---|---|---|---|
| 89 | 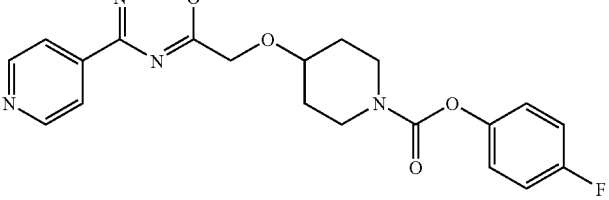 | 4-(3-Pyridin-4-yl-[1,2,4]oxadiazol-5-ylmethoxy)piperidine-1-carboxylic acid 4-fluorophenyl ester | 4.66 | 398.9 [M + H]+ |

4-[5-(Piperidin-4-yloxymethyl)-[1,2,4]oxadiazol-3-yl]pyridine (Preparation 17) was reacted with the appropriate acid chloride, in a manner similar to that described in Example 55, to afford the amides in Table 6.

TABLE 6

| Ex | Structure | Name | RT (min) | m/z (ES+) |
|---|---|---|---|---|
| 90 | 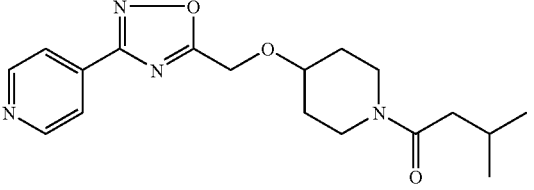 | 3-Methyl-1-[4-(3-pyridin-4-yl-[1,2,4]oxadiazol-5-ylmethoxy)piperidin-1-yl]-butan-1-one | 3.04 | 345.2 [M + H]+ |
| 91 | 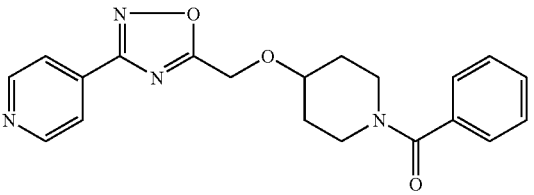 | Phenyl-[4-(3-pyridin-4-yl-[1,2,4]oxadiazol-5-ylmethoxy)piperidin-1-yl]methanone | 3.29 | 365.2 [M + H]+ |
| 92 | 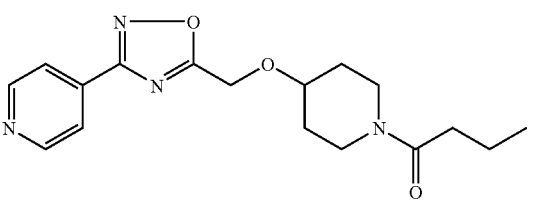 | 1-[4-(3-Pyridin-4-yl-[1,2,4]oxadiazol-5-ylmethoxy)piperidin-1-yl]butan-1-one | 2.90 | 331.2 [M + H]+ |
| 93 | 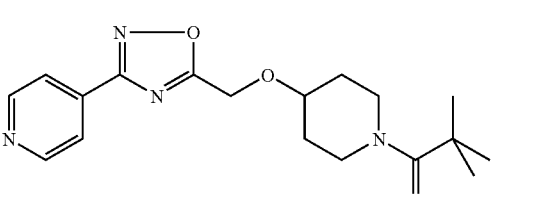 | 2,2-Dimethyl-1-[4-(3-pyridin-4-yl-[1,2,4]oxadiazol-5-ylmethoxy)piperidin-1-yl]propan-1-one | 3.09 | 345.2 [M + H]+ |
| 94 | 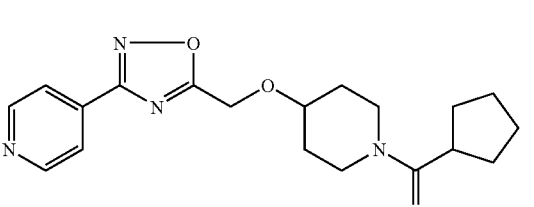 | Cyclopentyl-[4-(3-pyridin-4-yl-[1,2,4]oxadiazol-5-ylmethoxy)piperidin-1-yl]methanone | 3.39 | 357.2 [M + H]+ |

TABLE 6-continued

| Ex | Structure | Name | RT (min) | m/z (ES+) |
|---|---|---|---|---|
| 95 | 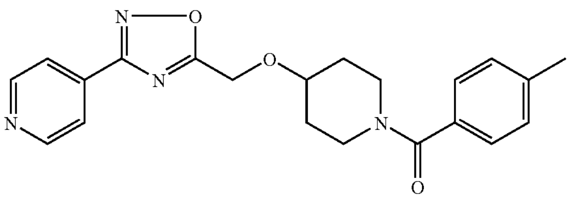 | (4-(3-Pyridin-4-yl-[1,2,4]oxadiazol-5-ylmethoxy)piperidin-1-yl]-p-tolylmethanone | 3.37 | 379.2 [M + H]+ |
| 96 | 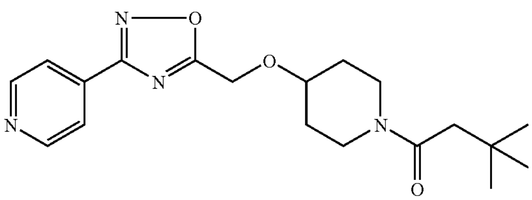 | 3,3-Dimethyl-1-[4-(3-pyridin-4-yl-[1,2,4]oxadiazol-5-ylmethoxy)piperidin-1-yl]butan-1-one | 3.29 | 359.1 [M + H]+ |

4-[5-(Piperidin-4-yloxymethyl)-[1,2,4]oxadiazol-3-yl]pyridine (Preparation 17) was reacted with the appropriate sulfonyl chloride, in a fashion similar to that described in Example 57, to afford the sulfonamides in Table 7.

TABLE 7

| Ex | Structure | Name | RT (min) | m/z (ES+) |
|---|---|---|---|---|
| 97 | 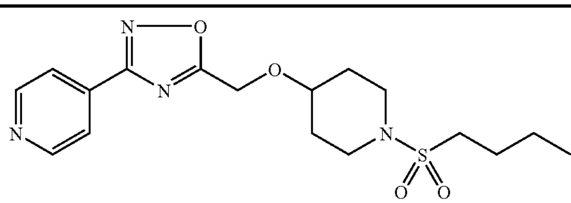 | 4-{5-[1-(Butane-1-sulfonyl)piperidin-4-yloxymethyl]-[1,2,4]oxadiazol-3-yl}pyridine | 3.34 | 381.2 [M + H]+ |
| 98 | 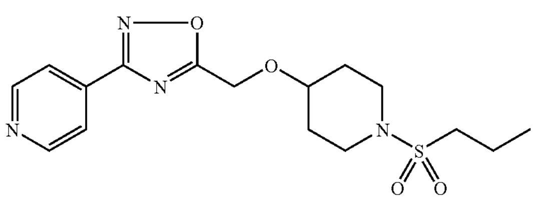 | 4-{5-[1-(Propane-1-sulfonyl)piperidine-4-yloxymethyl]-[1,2,4]oxadiazol-3-yl}pyridine | 3.12 | 367.1 [M + H]+ |

The compounds in Table 8 were synthesized by reacting 4-[5-piperidin-4-yloxymethyl)-[1,2,4]oxadiazol-3-yl]pyridine (Preparation 17) with the appropriate isocyanate, in a manner similar to that described in Example 58.

TABLE 8

| Ex | Structure | Name | RT (min) | m/z (ES+) |
|---|---|---|---|---|
| 99 | 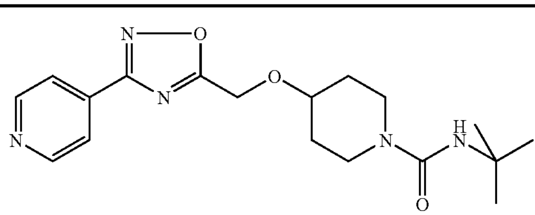 | 4-(3-Pyridin-4-yl-[1,2,4]oxadiazol-5-ylmethoxy)piperidine-1-carboxylic acid tert-butylamide | 2.95 | 360.4 [M + H]+ |

TABLE 8-continued

| Ex | Structure | Name | RT (min) | m/z (ES+) |
|---|---|---|---|---|
| 100 | 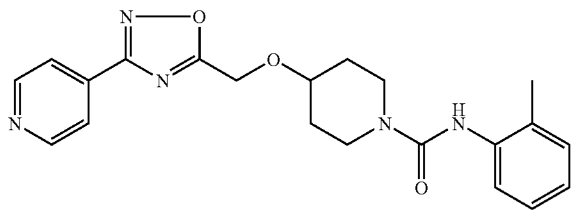 | 4-(3-Pyridin-4-yl-[1,2,4]oxadiazol-5-ylmethoxy)piperidine-1-carboxylic acid o-tolylamide | 3.44 | 394.4 [M + H]+ |

Example 101 trans-4-(3-Pyridin-4-yl-[1,2,4]oxadiazol-5-yl)cyclohexanecarboxylic acid propyl ester

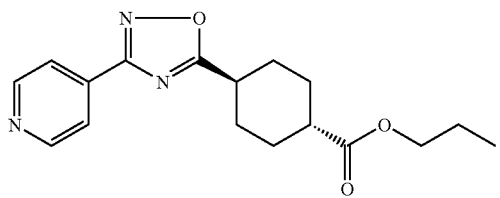

Thionyl chloride (11.5 µl, 0.1 mmol) was added to a solution of trans-4-(3-pyridin-4-yl-[1,2,4]oxadiazol-5-yl)cyclohexanecarboxylic acid (Preparation 4, 22 mg, 0.08 mmol) in 1-propanol (2 ml). The mixture was heated under reflux for 2 h, cooled and the solvent removed in vacuo. The residue was dissolved in EtOAc (10 ml), washed with saturated aqueous NaHCO$_3$ (3 ml) and brine (5 ml), then dried (MgSO$_4$). Removal of the solvent afforded the title compound. RT=3.67 min, m/z (ES+)=316.3 [M+H]+.

The esters in Table 9 were synthesised in a manner similar to that described in Example 101.

Example 104 trans-4-[5-(4-Propoxymethylcyclohexyl)-[1,2,4]oxadiazol-3-yl]pyridine

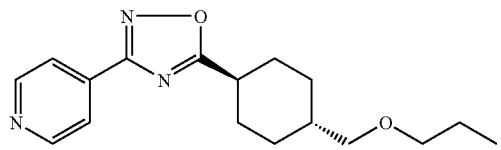

A solution of trans-(3-pyridin-4-yl-[1,2,4]oxadiazol-5-yl)cyclohexylmethanol (Preparation 6, 50 mg, 0.19 mmol) in THF (2.5 ml) was stirred with sodium hydride (27 mg of a 60% dispersion in oil, 0.68 mmol) for 1 h then 1-bromopropane (70 µl, 0.77 mmol) and tetrabutylammonium iodide (7 mg, 19 µmol) were added. The mixture was stirred at rt for 72 h, the solvent removed and the residue dissolved in CH$_2$C$_2$ (10 ml). After washing with water (3 ml), the organic phase was dried (MgSO$_4$) and evaporated. Purification of the resi-

TABLE 9

| Ex | Structure | Name | RT (min) | m/z (ES+) |
|---|---|---|---|---|
| 102 | 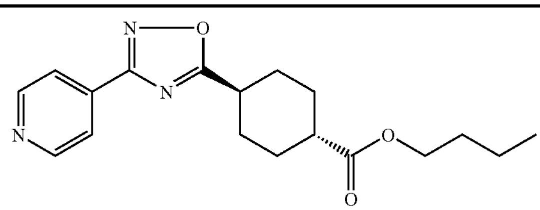 | trans-4-(3-Pyridin-4-yl-[1,2,4]oxadiazol-5-yl)cyclohexanecarboxylic acid butyl ester | 3.92 | 330.3 [M + H]+ |
| 103 | | trans-4-(3-Pyridin-4-yl-[1,2,4]oxadiazol-5-yl)cyclohexanecarboxylic acid isobutyl ester | 3.94 | 330.3 [M + H]+ | due by flash chromatography (IH-EtOAc, 7:3) afforded the title compound: RT=3.92 min, m/z (ES⁺)=302.3

Example 105 trans-4-[5-(4-Butoxymethylcyclohexyl)-[1,2,4]oxadiazol-3-yl]pyridine

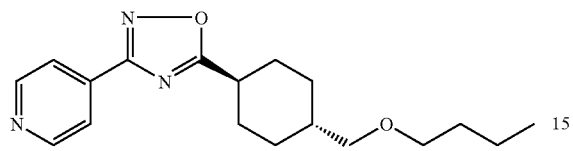

A solution of 4-(3-pyridin-4-yl-[1,2,4]oxadiazol-5-yl)cyclohexylmethanol (Preparation 6) in THF was treated with sodium hydride, 1-bromobutane and tetrabutylammonium iodide, as described for Example 104, to afford the title compound: RT=4.16 min, m/z (ES⁺)=316.3

Example 106 cis-4-[5-(3-Butoxymethylcyclopentyl)-[1,2,4]oxadiazol-3-yl]pyridine

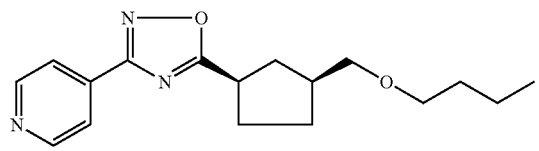

A solution of cis-[3-(3-pyridin-4-yl-[1,2,4]oxadiazol-5-yl)cyclopentyl]methanol (Preparation 5, 40 mg, 0.116 mmol) in anhydrous THF (2 ml) was treated with sodium hydride (23 mg of a 60% dispersion in oil, 0.57 mmol) and tetrabutylammonium iodide (6 mg, 16 μmol). After stirring the mixture at rt for 10 min, 1-bromobutane (59 μl, 0.65 mmol) was introduced and stirring continued for 72 h. The solvent was removed in vacuo, the residue dissolved in CH₂Cl₂ (20 ml) and washed with water (2×5 ml). The organic phase was dried (MgSO₄) and evaporated. Flash chromatography (IH-EtOAc, 7:3) afforded the title compound: RT=3.99 min, m/z (ES⁻)=302.3 [M+H]⁺.

Example 107 cis-4-[5-(3-Propoxymethylcyclopentyl)-[1,2,4]oxadiazol-3-yl]pyridine

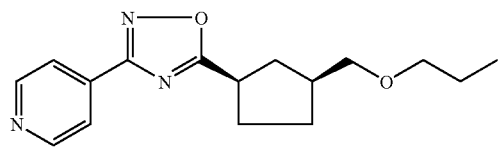

cis-[3-(3-Pyridin-4-yl-[1,2,4]oxadiazol-5-yl)cyclopentyl]methanol (Preparation 5) was reacted with 1-bromopropane in the presence of tetrabutylammonium iodide, using a similar procedure to that described in Example 106, to afford the title compound: RT=3.69 min, m/z (ES⁺)=288.3 [M+H]⁺.

Example 108 cis-4-[5-(3-Butoxymethylcyclohexyl)-[1,2,4]oxadiazol-3-yl]pyridine

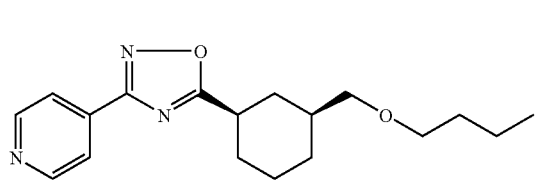

cis-Methyl-3-hydroxymethylcyclohexane-1-carboxylate was reacted with N-hydroxy-isonicotinamidine, using the reaction conditions described in Preparation 5, to afford cis-[3-(3-pyridin-4-yl-[1,2,4]oxadiazol-5-yl)cyclohexyl]methanol: RT=2.70 min, m/z (ES⁺)=246.1 [M+H]⁺. This was subsequently alkylated with 1-bromobutane, under similar conditions to those described in Example 106, to afford the title compound: RT=4.11 min, m/z (ES⁺)=316.3 [M+H]⁺.

Example 109

4-(3-Pyridin-4-yl-[1,2,4]oxadiazol-5-ylmethoxy)-3,4,5,6-tetrahydro-2H-[1,3']bipyridinyl

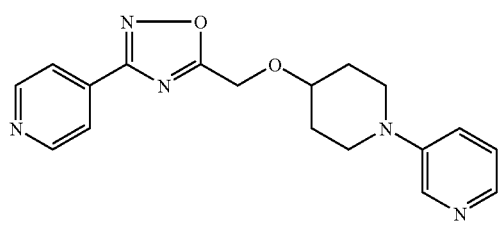

Sodium tert-butoxide (86 mg, 900 μmol) was added to a solution of 3-chloropyridine (23 mg, 200 μmol), 4-[5-(piperidin-4-yloxymethyl)[1,2,4]oxadiazol-3-yl]pyridine (Preparation 17, 65 mg, 250 μmol), Pd₂ dba₃ (4 mg, 4 μmol) and 2,8,9-trisobutyl-2,5,8,9-tetraaza-1-phosphabicyclo[3.3.3]undecane (6 mg, 16 μmol) in toluene (3 ml) and the resulting mixture heated at 80° C. for 48 h. After cooling and filtering through celite, the solvent was removed and the residue purified by HPLC to afford the title compound: RT=2.64 min; m/z (ES⁺)=338.0 [M+H]⁺.

The compounds in Table 10 were prepared in a similar fashion to that described in Example 109.

TABLE 10

| Ex | Structure | Name | RT (min) | m/z (ES+) |
|---|---|---|---|---|
| 110 | 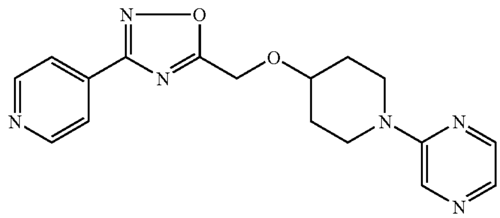 | 2-[4-(3-Pyridin-4-yl-[1,2,4]oxadiazol-5-ylmethoxy)piperidin-1-yl]pyrazine | 3.24 | 339.0 [M + H]+ |
| 111 | 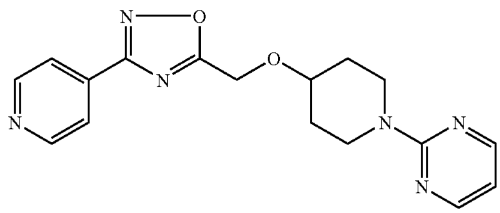 | 2-[4-(3-Pyridin-4-yl-[1,2,4]oxadiazol-5-ylmethoxy)piperidin-1-yl]pyrimidine | 3.19 | 339.0 [M + H]+ |

Example 112

(4-Pentylcyclohexyl)-(3-pyridin-4-yl-[1,2,4]oxadiazol-5-ylmethyl)amine

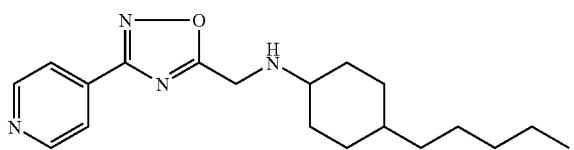

A solution of C-3-pyridin-4-yl-[1,2,4]oxadiazol-5-yl)methylamine (Preparation 9, 50 mg, 284 mmol), 4-pentylcyclohexanone (64 ml, 340 mmol) and sodium triacetoxyborohydride (96 mg, 450 mmol) in $CH_2Cl_2$ (4 ml) were stirred 18 h at rt. The reaction was quenched by the addition of 2M aqueous sodium hydroxide (2 ml) and the mixture diluted with EtOAc (25 ml). The organic phase was separated, washed with brine (5 ml) and dried ($MgSO_4$). The solvent was removed and the residue purified by flash chromatography (IH-EtOAc, 1:1) to afford the title compound: RT=3.12 min; m/z (ES+)=329.3 [M+H]+.

The amines in Table 11 were synthesized in a manner similar to that described in Example 112.

TABLE 11

| Ex | Structure | Name | RT (min) | m/z (ES+) |
|---|---|---|---|---|
| 113 | 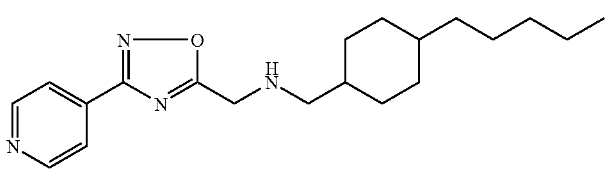 | (4-Pentylcyclohexylmethyl)-(3-pyridin-4-yl-[1,2,4]oxadiazol-5-ylmethyl)amine | 3.19 | 343.2 [M + H]+ |
| 114 | 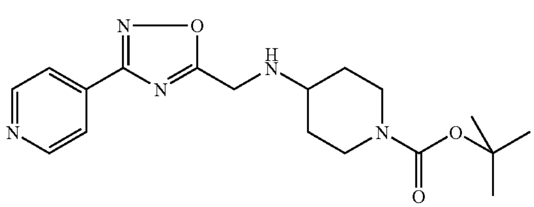 | 4-[(3-Pyridin-4-yl-[1,2,4]oxadiazol-5-ylmethyl)amino]piperidine-1-carboxylic acid tert-butyl ester | 2.42 | 360.2 [M + H]+ |
| 115 | 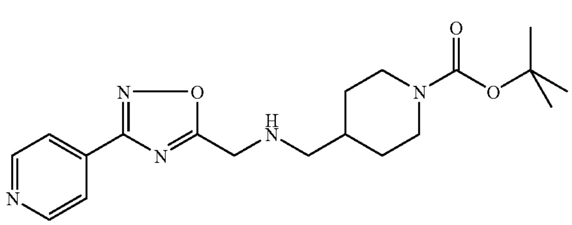 | 4-{[(3-Pyridin-4-yl-[1,2,4]oxadiazol-5-ylmethyl)amino]methyl}-piperidine-1-carboxylic acid tert-butyl ester | 2.65 | 374.2 [M + H]+ |

TABLE 11-continued

| Ex | Structure | Name | RT (min) | m/z (ES+) |
|---|---|---|---|---|
| 116 | 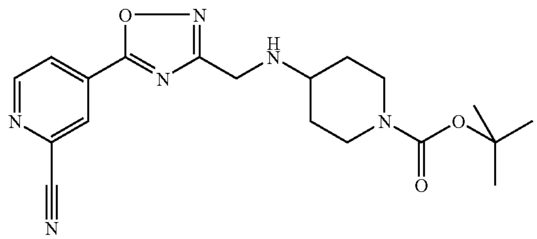 | 4-{[5-(2-Cyanopyridin-4-yl)-[1,2,4]oxadiazol-3-ylmethyl]amino}-piperidine-1-carboxylic acid tert-butyl ester | 2.59 | 385.1 [M + H]+ |

Example 117

Methyl-(4-pentylcyclohexyl)-(3-pyridin yl-[1,2,4]oxadiazol-5-ylmethyl)amine

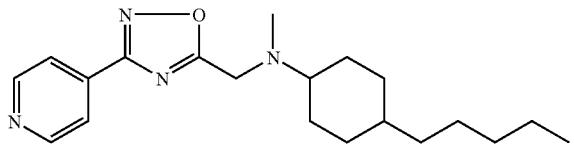

A solution of (4-pentylcyclohexyl)-(3-pyridin-4-yl-[1,2,4]oxadiazol-5-ylmethyl)amine (Example 112, 30.9 mg, 94 µmol) in dichloroethane (1.3 ml) at rt was treated with formaldehyde (8.4 ml of a 37% aqueous solution, 103 µmol) and sodium triacetoxyborohydride (28 mg, 132 µmol). After stirring for 48 h, the solvent was removed and 2M aqueous sodium hydroxide (1 ml) added. The mixture was extracted into EtOAc (25 ml) which was dried (MgSO4) and evaporated. The residue was purified by flash chromatography (IH-EtOAc 7:3) to afford the title compound: RT=3.37 min; m/z (ES+)=343.2 [M+H]+.

The amines in Table 12 were synthesized in a manner similar to that described in Example 117.

TABLE 12

| Ex | Structure | Name | RT (min) | m/z (ES+) |
|---|---|---|---|---|
| 118 | 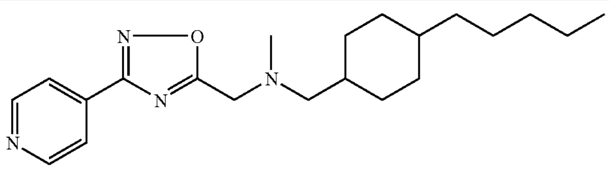 | Methyl-(4-pentylcyclohexylmethyl)-(3-pyridin-4-yl-[1,2,4]oxadiazol-5-ylmethyl)amine | 4.05 | 357.2 [M + H]+ |
| 119 | 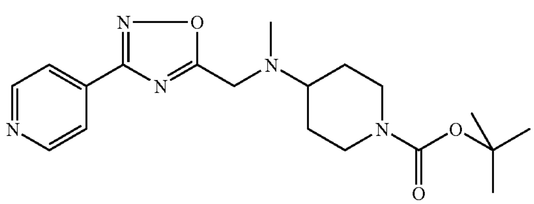 | 4-[Methyl-(3-pyridin-4-yl-[1,2,4]oxadiazol-5-ylmethyl)amino]piperidine-1-carboxylic acid tert-butyl ester | 2.82 | 374.2 [M + H]+ |
| 120 | 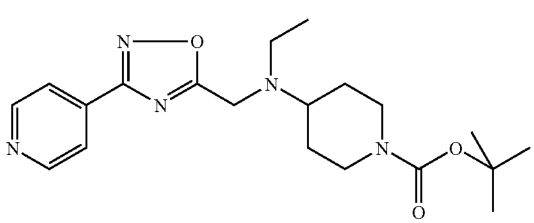 | 4-[Ethyl-(3-pyridin-4-yl-[1,2,4]oxadiazol-5-ylmethyl)amino]piperidine-1-carboxylic acid tert-butyl ester | 3.01 | 388.2 [M + H]+ |
| 121 | 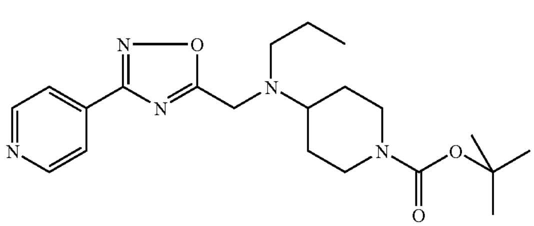 | 4-[Propyl-(3-pyridin-4-yl-[1,2,4]oxadiazol-5-ylmethyl)amino]piperidine-1-carboxylic acid tert-butyl ester | 3.39 | 402.2 [M + H]+ |

TABLE 12-continued

| Ex | Structure | Name | RT (min) | m/z (ES+) |
|---|---|---|---|---|
| 122 | 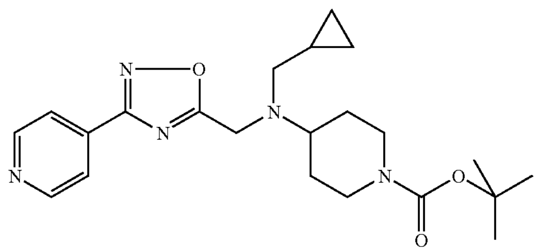 | 4-[Cyclopropylmethyl-(3-pyridin-4-yl-[1,2,4]oxadiazol-5-ylmethyl)amino]piperidine-1-carboxyle acid tert-butyl ester | 3.17 | 414.1 [M + H]+ |
| 123 | 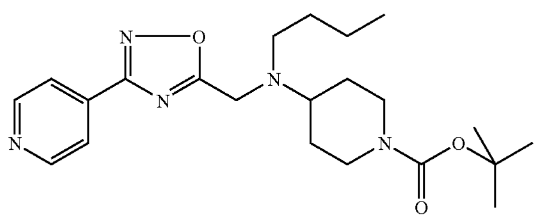 | 4-[Butyl-(3-pyridin-4-yl-[1,2,4]oxadiazol-5-ylmethyl)amino]piperidine-1-carboxylic acid tert-butyl ester | 3.45 | 416.1 [M + H]+ |
| 124 | 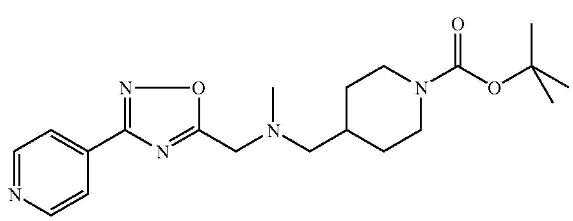 | 4-{[Methyl-(3-pyridin-4-yl-[1,2,4]oxadiazol-5-ylmethyl)amino]methyl}-piperidine-1-carboxylic acid tert-butyl ester | 3.12 | 388.2 [M + H]+ |
| 125 | 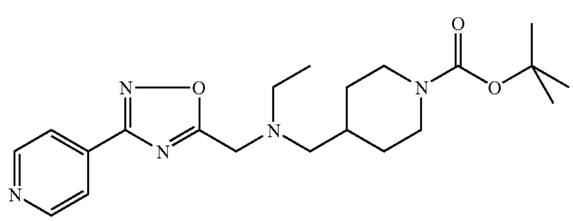 | 4-{[Ethyl-(3-pyridin-4-yl-[1,2,4]oxadiazol-5-ylmethyl)amino]methyl}-piperidine-1-carboxylic acid tert-butyl ester | 3.22 | 402.2 [M + H]+ |
| 126 | 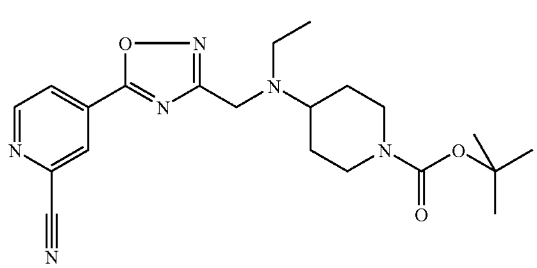 | 4-{[5-(2-Cyanopyridin-4-yl)-[1,2,4]oxadiazol-3-ylmethyl]ethylamino}-piperidine-1-carboxylic acid tert-butyl ester | 2.77 | 413.2 [M + H]+ |

Example 127

4-[Methyl-(3-pyridin-4-yl-[1,2,4]oxadiazol-5-ylmethyl)amino]piperidine-1-carboxylic acid cyclopentyl ester

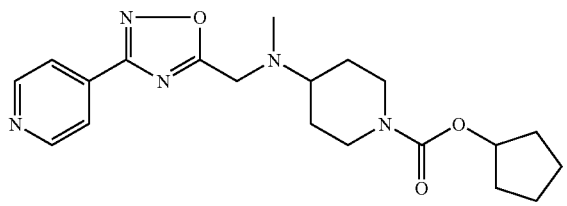

The tert-butoxycarbonyl group of 4-[methyl(3-pyridin-4-yl-[1,2,4]oxadiazol-5-ylmethyl)amino]piperidine-1-carboxylic acid tert-butyl ester (Example 119) was removed using the procedure described in Example 51 to afford methylpiperidin-4-yl-(3-pyridin-4-yl-[1,2,4]oxadiazol-5-ylmethyl)amine: RT=0.65 min; m/z (ES+)=274.0 [M+H]+. Derivatisation of methylpiperidin-4-yl-(3-pyridin-4-yl-[1,2,4]oxadiazol-5-ylmethyl)amine with cyclopentylchloroformate, using the procedure described for Example 52, afforded the title compound: RT=3.02 min; m/z (ES+)=386.0 [M+H]+.

Example 128

4-{[Methyl-(3-pyridin-4-yl-[1,2,4]oxadiazol-5-ylmethyl)amino]methyl}-piperidine-1-carboxylic acid 2,2,2-trichloroethyl ester

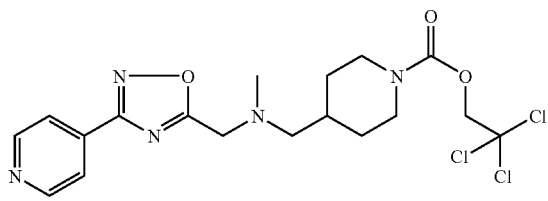

The tert-butoxycarbonyl group of 4-{[methyl(3-pyridin-4-yl-[1,2,4]oxadiazol-5-ylmethyl)amino]methyl}piperidine-1-carboxylic acid tert-butyl ester (Example 124) was removed using the procedure described in Example 51 to afford methylpiperidin-4-ylmethyl-(3 pyridin yl-[1,2,4]oxadiazol-5-ylmethyl)amine: RT=0.75 min; m/z (ES+)=288.0 [M+H]+. Derivatisation of methylpiperidin-4-ylmethyl-(3-pyridin-4-yl-[1,2,4]oxadiazol-5-ylmethyl)amine with 2,2,2-trichloroethylchloroformate, using the procedure described for Example 52, afforded the title compound: RT=3.51 min; m/z (ES+)=461.9 [M+H]+.

Example 129

4-(3-Pyridin-4-yl-[2,4]oxadiazol-5-ylmethoxymethyl)piperidine-1-carboxylic acid tert-butyl ester

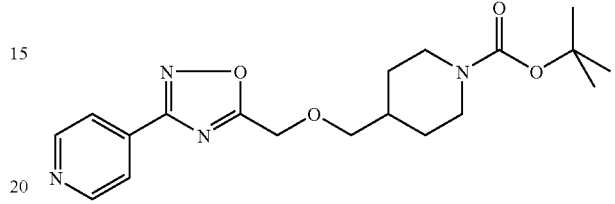

Sodium hydride (19.5 mg, 0.49 mmol) was added to a solution of (3-pyridin-4-yl-[1,2,4]oxadiazol-5-yl)methanol (Preparation 11, 86 mg, 0.49 mmol) in anhydrous THF (3 ml). After stirring at rt for 5 min, 15-crown-5 (97 µl, 0.49 mmol) was added followed by 4-methanesulfonyloxymethylpiperidine-1-carboxylic acid tert-butyl ester (143 mg, 0.487 mmol). The reaction mixture was heated in a microwave oven (750 W) at 100° C. for 15 min, cooled and the solvent evaporated. The residue was taken up in CH$_2$Cl$_2$ (100 ml), washed with water (10 ml), dried (MgSO$_4$) and the solvent evaporated. The residue was purified by flash chromatography (IH-EtOAc, 1:1) to afford the title compound: RT=3.67 min; m/z (ES+)=375.2 [M+H]+.

Example 130

4-(3-Pyridin-4-yl-[1,2,4]oxadiazol-5-ylmethyl)piperazine-1-carboxylic acid tert-butyl ester

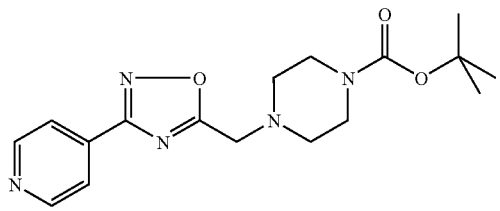

Methanesulfonic acid 3-pyridin-4-yl-[1,2,4]oxadiazol-5-ylmethyl ester (Preparation 12, 56 mg, 0.22 mmol) and potassium carbonate (30 mg, 0.22 mmol) were added to a solution of piperazine-1-carboxylic acid tert-butyl ester (37 mg, 0.2 mmol) in acetonitrile (4 ml). The stirred mixture was heated under reflux for 18 h, the solvent removed and the residue dissolved in EtOAc-water (90:10, 50 ml). The organic phase was separated, washed with brine, dried (MgSO$_4$) and the solvent removed to give a residue which was purified by flash

Example 131

4-(3-Pyridin-4-yl-[1,2,4]oxadiazol-5-ylmethylsulfanyl)piperidine-1-carboxylic acid tert-butyl ester

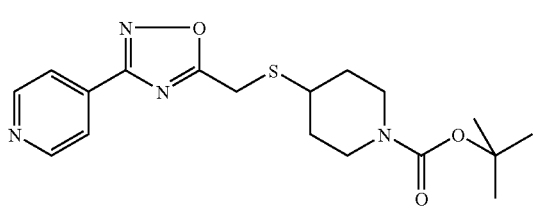

t-BuOK (92 mg, 823 µmol) and methanesulfonic acid 3-pyridin-4-yl-[1,2,4]oxadiazol-5-ylmethyl ester (Preparation 12, 150 mg, 588 µmol) were added to a stirred solution of 4-mercaptopiperidine-1-carboxylic acid tert-butyl ester (191 mg, 881 mol) in anhydrous THF (10 ml). After 100 min, the reaction mixture was diluted with Et$_2$O, before being washed with NaHCO$_3$ and brine. The organic layer was dried (MgSO$_4$), filtered, and concentrated, then the residue was purified by column chromatography (IH-EtOAc, 3:2) to afford the title compound: RT=3.77 min; m/z (ES$^+$)=377.2 [M+H]$^+$.

Example 132

4-(3-Pyridin-4-yl-[1,2,4]oxadiazol-5-ylmethanesulfonyl)piperidine-1-carboxylic acid tert-butyl ester

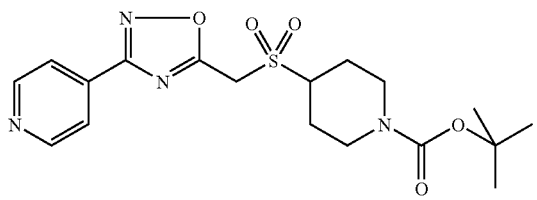

mCPBA (111 mg of 65% pure, 418 µmol) was added to a stirred solution of 4-(3-pyridin-4-yl-[1,2,4]oxadiazol-5-ylmethylsulfanyl)piperidine-1-carboxylic acid tert-butyl ester (Example 131, 105 mg, 279 µmol) in CH$_2$Cl$_2$ (7 ml). After 110 min, the reaction was quenched with saturated aqueous Na$_2$CO$_3$. The organic layer was washed with brine, dried (MgSO$_4$), filtered, and concentrated. Column chromatographic purification (4:1 EtOAc-IH) afforded the title compound: RT=3.40 min; m/z (ES$^+$)=353.1 [M-t-Bu+2H]$^+$.

Example 133

4-(5-Pyridin-4-yl-[1,3,4]oxadiazol-2-ylmethoxy)piperidine-1-carboxylic acid tert-butyl ester

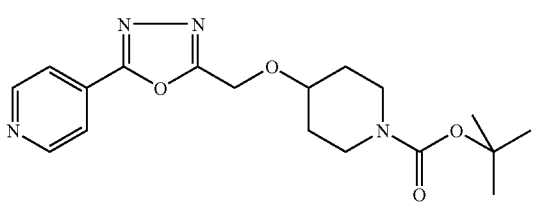

Triethylamine (149 µl, 1.06 mmol was added to stirred solution of 4-{2-oxo-2-[N'-(pyridine-4-carbonyl)hydrazino]ethoxy}piperidine-1-carboxylic acid tert-butyl ester (Preparation 16, 200 mg, 0.53 mmol) and 2-chloro-1,3-dimethyl-2-imidazolinium hexafluorophosphate (147 mg, 0.53 mmol) in CH$_2$Cl$_2$ (10 ml). After 18 h at rt, the solvent was reduced to a small volume and this mixture purified by flash chromatography (EtOAc), affording the title compound: RT=3.42 min; m/z (ES$^+$)=361.1 [M+H]$^+$.

Example 134

3-Pyridin-4-yl-[1,2,4]oxadiazole-5-carboxylic acid (4-pentylcyclohexyl)amide

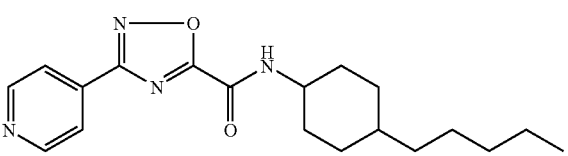

A solution of 3-pyridin-4-yl-[1,2,4]oxadiazole-5-carboxylic acid ethyl ester (50.5 mg, 0.23 mmol) and 4-pentylcyclohexylamine (39 mg, 0.23 mmol) in anhydrous toluene (2 ml) was treated with triethylaluminium (345 µl of a 2M solution in hexanes, 0.69 mmol). After stirring at rt for 18 h, saturated aqueous NaHCO$_3$ (2 ml) was added and the mixture diluted with CH$_2$Cl$_2$ (25 ml). The organic phase was separated, washed with brine (5 ml) and dried (MgSO$_4$). The solvent was

Example 135

[4-(3-Pyridin-4-yl-[1,2,4]oxadiazol-5-ylmethoxy)piperidin-1-yl]phosphonic acid diphenyl ester

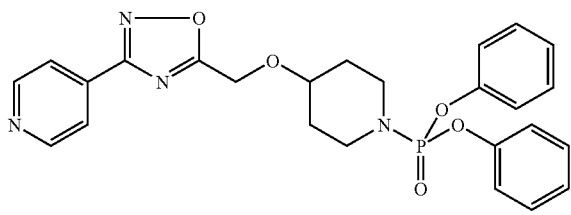

A solution of pyridine (31 µl, 0.38 mmol) and 4-[5-piperidin-4-yloxymethyl]-[1,2,4]oxadiazol-3-yl]pyridine (Preparation 17, 49 mg, 0.19 mmol) in $CH_2Cl_2$ (4 ml) was treated with phosphorochloridic acid diphenyl ester (103 mg, 0.38 mmol). The reaction was stirred at rt for 18 h then quenched with saturated aqueous $NaHCO_3$ (1 ml). The organic phase was separated, evaporated and the residue purified by HPLC to afford the title compound: RT=3.79 min, m/z (ES$^+$)=493.1 [M+H]$^+$.

Example 136

4-(4-Pyridin-4-yl-thiazol-2-ylmethoxy)piperidine-1-carboxylic acid tert-butyl ester

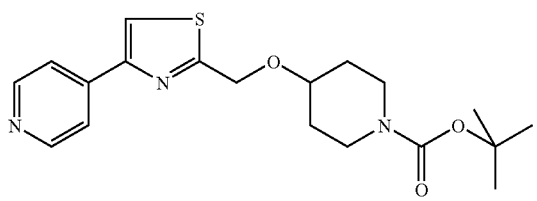

A solution of 2-bromo-1-pyridin-4-yl-ethanone hydrobromide (35 mg, 1241 mol) and 4-thiocarbamoylmethoxypiperidine-1-carboxylic acid tert-butyl ester (Preparation 18, 34 mg, 124 µmol) in methanol (2 ml) was heated at 60° C. for 1.5 h. The reaction mixture was diluted with EtOAc (60 ml), washed with saturated aqueous $NaHCO_3$ (15 ml) and brine (15 ml) then dried ($MgSO_4$). The solvent was removed and the residue purified by flash chromatography (EtOAc) to afford the title compound: RT=2.95 ml, m/z (ES$^+$)=376.1 [M+H]$^+$.

Example 137

4-(2-Pyridin yl-thiazol-4-ylmethyl)piperidine-1-carboxylic acid tert-butyl ester

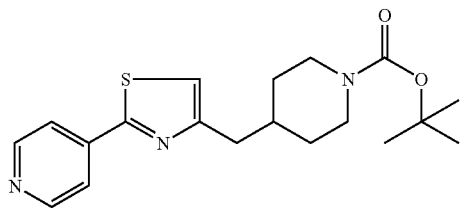

4-(3-Bromo-2-oxopropyl)piperidine-1-carboxylic acid tert-butyl ester was reacted with thioisonicotinamide in a manner similar to that described in Example 136 to afford the title compound: RT=3.39 min, m/z (ES$^+$)=360.1 [M+H]$^+$.

Example 138 trans-4-[5-(4-Pentyl-cyclohexyl)-[1,3,4]thiadiazol-2-yl]pyridine

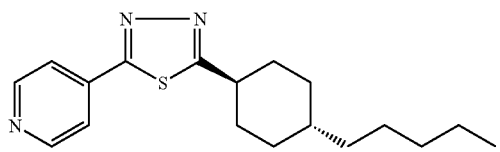

A solution of 4-pentyl-cyclohexanecarboxylic acid N'-(pyridine-4-carbonyl)hydrazide (Preparation 19, 50 mg, 0.158 mmol) and Lawesson's reagent (127 mg, 0.32 mmol) in toluene (2 ml) was heated under reflux for 18 h. The solvent was evaporated and the residue purified by flash chromatography (IH-EtOAc, 4:1 then EtOAc) to afford the title compound: RT=5.02 min; m/z (ES$^+$)=316.0 [M+H]$^+$.

Example 139

4-(5-Pyridin-4-yl-[1,3,4]thiadiazol-2-ylmethoxy)piperidine-1-carboxylic acid tert-butyl ester

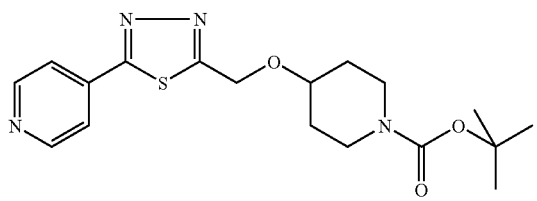

4-{2-Oxo-2-[N'-(pyridine-4-carbonyl)hydrazino]ethoxy}piperidine-1-carboxylic acid tert-butyl ester (Preparation 16) was treated with Lawesson's reagent in a similar manner to that described in Example 138, affording the title compound: RT=3.47 min, m/z (ES⁺)=377.1 [M+H]⁺.

Example 140

4-(5-Pyridin-4-yl-4H-[1,2,4]triazol-3-ylmethoxy) piperidine-1-carboxylic acid tert-butyl ester

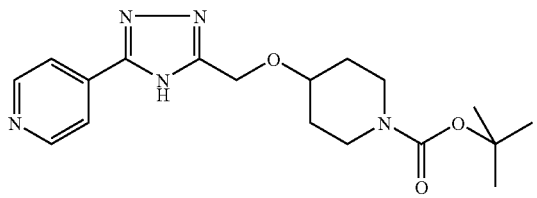

A solution of 4-carboxymethoxypiperidine-1-carboxylic acid tert-butyl ester (Preparation 1, 255 mg, 0.952 mmol) and triethylamine (138 μl, 0.982 mmol) in toluene was cooled to 0° C. and isobutylchloroformate (127 μl, 0.982 mmol) added. After stirring at rt for 45 min 4-pyridinecarboximidic acid hydrazide (100 mg, 0.82 mmol) and 3 Å powdered molecular sieves (0.82 g) were added and the reaction heated under reflux for 18 h. On cooling, the mixture was filtered through celite, the filtrate evaporated and the residue dissolved in EtOAc (50 ml). After washing with saturated aqueous Na₂CO₃ (10 ml) and brine (10 ml), the solvent was removed and the residue purified by flash chromatography (EtOAc then 5% MeOH in EtOAc) to afford the title compound: RT=2.81 min; m/z (ES⁺)=360.1 [M+H]⁺.

Example 141

4-[2-(5-Pyridinyl-isoxazol-3-yl)ethyl]piperidine-1-carboxylic acid tert-butyl ester

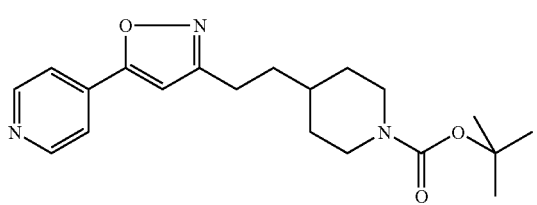

HONH₂.HCl (29 mg, 418 μmol) and Na₂CO₃ (29 mg, 277 μmol) were added to a stirred solution of 4-(3,5-dioxo-5-pyridin-4-ylpentyl)piperidine-1-carboxylic acid tert-butyl ester (Preparation 22, 98 mg, 271 μmol) in EtOH (0.75 ml) and H₂O (0.45 ml). The reaction was heated at 70° C. (bath) for 4 h, then the solvents were removed under reduced pressure. The residue was purified by RP-HPLC to afford the title compound: RT=3.57 min; m/z (ES⁺)=358.3 [M+H]⁺.

Example 142

4-(5-Pyridinyl-isoxazol-3-ylmethoxy)piperidine-1-carboxylic acid tert-butyl ester

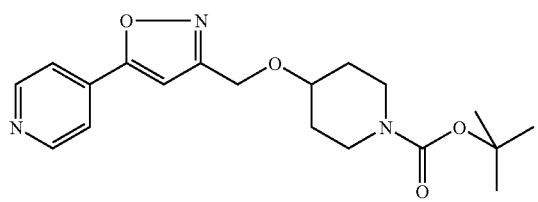

Condensation of HONH₂ with 4-(2,4-dioxo-4-pyridin-4-ylbutoxy)piperidine-1-carboxylic acid tert-butyl ester (Preparation 23), as outlined in Example 141, afforded the title compound: RT=3.34 min; m/z (ES⁺)=360.3 [M+H]⁺.

Example 143

4-(5-Pyridin-4-yl-isoxazol-3-ylmethyl)piperidino-1-carboxylic acid tert-butyl ester

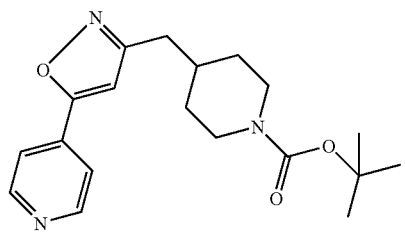

Condensation of HONH₂ with 4-(2,4-dioxo-4-pyridin-4-ylbutyl)piperidine-1-carboxylic acid tert-butyl ester (Preparation 24), as outlined in Example 141, afforded the title compound: RT=3.47 min; m/z (ES⁺)=344.3 [M+H]⁺.

Examples 144 and 145

4-[2-(1-Methyl-5-pyridin-4-yl-1H-pyrazol-3-yl) ethyl]piperidine-1-carboxylic acid tert-butyl ester and 4-[2-(2-Methyl-5-pyridin-4-yl-2H-pyrazol-3-yl) ethyl]-piperidine-1-carboxylic acid tert-butyl ester

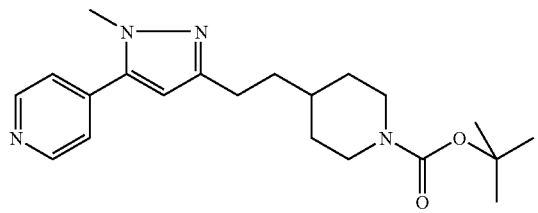

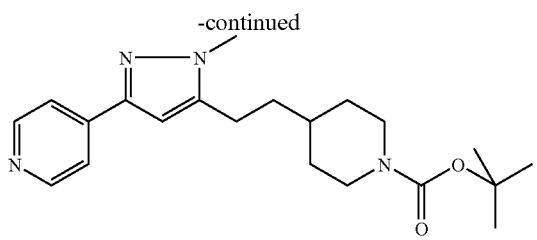

MeNHNH₂ (16 mg, 3481 mol) was added to a stirred solution of 4-(3,5-dioxo-5-pyridin-4-yl-pentyl)piperidine-1-carboxylic acid tert-butyl ester (Preparation 22, 96 mg, 268 µmol) in EtOH (1 ml). The reaction was heated under reflux for 4 h, then the solvents were removed under reduced pressure. The residue was purified by RP-HPLC to afford Example 144: RT=3.22 min; m/z (ES⁺)=371.3 [M+H]⁺; and Example 145: RT=2.99 min; m/z (ES⁺)=371.3 [M+H]⁺.

Example 146

(E)-4-{5-[2-(2-Cyanopyridin-4-yl)vinyl]-[1,2,4]oxadiazol-3-yl}piperidine-1-carboxylic acid tert-butyl ester

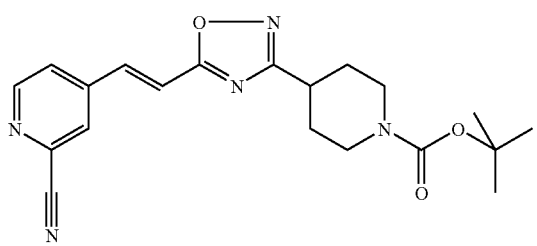

A solution of mCPBA (9.4 mg of 77% pure, 421 mmol) in CHCl₃ (0.5 ml) was added to a stirred solution of (E)-4-[5-(2-pyridin-4-ylvinyl)-[1,2,4]oxadiazol-3-yl]piperidine-1-carboxylic acid tert-butyl ester (Example 46, 15 mg, 4211 mol) in CHCl₃ (1 ml) at 0° C. The mixture was stirred at 20° C. for 16 h, before being treated with more mCPBA (2.5 mg of 77% pure, 11 µmol). After 2 h, the reaction was concentrated, then the residue was purified by column chromatography (EtOAc then THF) to yield (E)-4-{5-[2-(1-oxypyridin-4-yl)vinyl]-[1,2,4]oxadiazol-3-yl}piperidine-1-carboxylic acid tert-butyl ester: m/z (ES⁺)=373.3 [M+H]⁺. This N-oxide (13 mg, 35 µmol) was treated with TMS-CN (14 µl, 130 µmol), NEt₃ (10 µl, 70 µmol), CH₂Cl₂ (250 µl) and Me₂NCOCl (3 µl). After 18 h, the solvents were evaporated and the residue purified by column chromatography (IH-EtOAc, 1:1) to afford the title compound: RT=3.99 min; m/z (ES⁺)=382.3 [M+H]⁺.

Example 147

4-{5-[2-(2H-Tetrazol-5-yl)pyridin-4-yl]-[2,4]oxadiazol-3-ylmethoxy}-piperidine-1-carboxylic acid tert-butyl ester

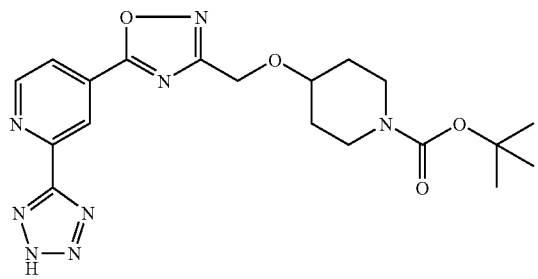

To a stirred solution of 4-[5-(2-cyanopyridin-4-yl)-[1,2,4]oxadiazol-3-ylmethoxy]piperidine-1-carboxylic acid tert-butyl ester (Example 42, 52 mg, 0.14 mmol) in DMF (3 ml) heated to 90° C. was added sodium azide (9 mg, 0.15 mmol) as a suspension in DMF (2 ml). After 3 h, sodium azide (18 mg, 0.29 mmol) was added in one portion and the reaction mixture stirred at 90° C. for a further 16 h. The reaction mixture was allowed to cool to rt then all solvents were removed in vacuo. The residue was suspended in EtOAc then filtered through a sinter, washing with EtOAc. The solid was partitioned between EtOAc (20 ml) and water (10 ml) containing AcOH (5 drops). The layers were separated then the aqueous extracted with EtOAc (3×20 ml). The combined organics were washed with brine (20 ml), dried (MgSO₄), filtered and concentrated in vacuo to afford the title compound which needed no further purification: RT=3.44 min; m/z (ES⁺)=429.1 [M+H]⁺.

Example 148

4-[5-(2-Cyanopyridin-4-yl)-[1,2,4]oxadiazol-3-ylmethoxy]piperidine-1-carboxylic acid isopropyl ester

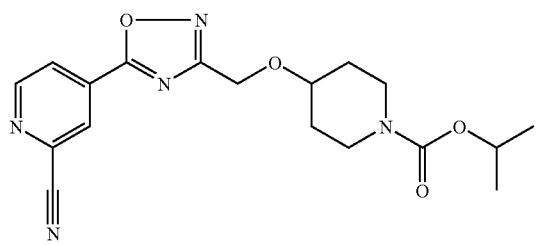

To a stirred solution of 4-[3-piperidin-4-yloxymethyl)-[1,2,4]oxadiazol-5-yl]pyridine-2-carbonitrile (Preparation 25, 300 mg, 1.1 mmol) in DCM (10 ml) was added triethylamine (0.3 ml, 2.1 mmol). The resulting solution was transferred to a stirred solution of isopropylchloroformate (2.1 ml of a 1M solution in PhMe, 2.1 mmol) in DCM (30 ml) and stirring was continued for 30 min at rt. The reaction mixture was diluted with EtOAc (30 ml) then washed successively with water (50 ml), saturated aqueous sodium carbonate (50 ml) and brine (50 ml). The organics were dried (MgSO$_4$) then adsorbed onto silica gel. Purification via chromatography (EtOAc-IH, 1:1) afforded the title compound: RT=3.44 min; m/z (ES$^+$) =372.04 [M+H]$^+$.

Example 149

4-[5-(2-Cyanopyridin-4-yl)[1,2,4]oxadiazol-3-yl-methoxy]piperidine-1-carboxylic acid phenyl ester

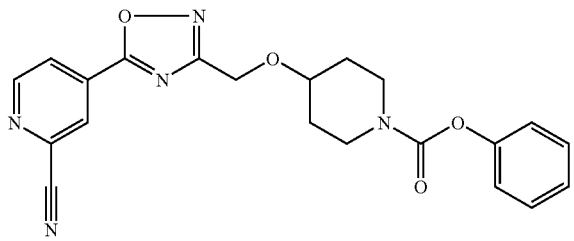

To a stirred solution of 4-[3-(piperidin-4-yloxymethyl)[1,2,4]oxadiazol-5-yl]pyridine-2-carbonitrile (Preparation 25, 700 mg, 2.5 mmol) in DCM (30 ml) was added triethylamine (0.7 ml, 4.9 mmol). The resulting solution was transferred to a stirred solution of phenylchloroformate (0.62 ml, 4.9 mmol) in DCM (30 ml) and stirring was continued for 30 min at rt. The reaction mixture was diluted with EtOAc (250 ml) then washed successively with water (100 mL), saturated aqueous sodium carbonate (100 ml) and brine (100 ml). The organics were dried (MgSO$_4$) then adsorbed onto silica gel. Purification via chromatography (EtOAc-IH, 1:1 to 3:2) afforded the title compound: RT=3.63 nm in; m/z (ES$^+$)=406.01 [M+H]$^+$.

The biological activity of the compounds of the invention may be tested in the following assay systems:
Yeast Reporter Assay The yeast cell-based reporter assays have previously been described in the literature (e.g. see Miret J. J. et al, 2002, J. Biol. Chem., 277: 6881-6887; Campbell R. M. et al, 1999, Bioorg. Med. Chem. Lett., 9: 2413-2418; King K. et al, 1990, Science, 250: 121-123); WO 99/14344; WO 00/12704; and U.S. Pat. No. 6,100,042). Briefly, yeast cells have been engineered such that the endogenous yeast G-alpha (GPA1) has been deleted and replaced with G-protein chimeras constructed using multiple techniques. Additionally, the endogenous yeast alpha-cell GPCR, Ste 3 has been deleted to allow for a homologous expression of a mammalian GPCR of choice. In the yeast, elements of the pheromone signaling transduction pathway, which are conserved in eukaryotic cells (for example, the mitogen-activated protein kinase pathway), drive the expression of Fus1. By placing β-galactosidase (LacZ) under the control of the Fus1 promoter (Fus1p), a system has been developed whereby receptor activation leads to an enzymatic read-out.

Yeast cells were transformed by an adaptation of the lithium acetate method described by Agatep et al, (Agatep, R. et al, 1998, Transformation of Saccharomyces cerevisiae by the lithium acetate/single-stranded carrier DNA/polyethylene glycol (LiAc/ss-DNA/PEG) protocol. Technical Tips Online, Trends Journals, Elsevier). Briefly, yeast cells were grown overnight on yeast tryptone plates (YT). Carrier single-stranded DNA (10 μg), 2 μg of each of two Fus1p-LacZ reporter plasmids (one with URA selection marker and one with TRP), 2 μg of GPR116 (human or mouse receptor) in yeast expression vector (2 μg origin of replication) and a lithium acetate/polyethylene glycol/TE buffer was pipetted into an Eppendorf tube. The yeast expression plasmid containing the receptor/no receptor control has a LEU marker. Yeast cells were inoculated into this mixture and the reaction proceeds at 30° C. for 60 min. The yeast cells were then heat-shocked at 42° C. for 15 min. The cells were then washed and spread on selection plates. The selection plates are synthetic defined yeast media minus LEU, URA and TRP (SD-LUT). After incubating at 30-C for 2-3 days, colonies that grow on the selection plates were then tested in the LacZ assay.

In order to perform fluorimetric enzyme assays for β-galactosidase, yeast cells carrying the human or mouse GPR116 receptor were grown overnight in liquid SD-LUT medium to an unsaturated concentration (i.e. the cells were still dividing and had not yet reached stationary phase). They were diluted in fresh medium to an optimal assay concentration and 90 μl of yeast cells are added to 96-well black polystyrene plates (Costar). Compounds, dissolved in DMSO and diluted in a 10% DMSO solution to 10× concentration, were added to the plates and the plates placed at 30° C. for 4 h After 4 h, the substrate for the β-galactosidase was added to each well. In these experiments, Fluorescein di (β-D-galactopyranoside) was used (FDG), a substrate for the enzyme that releases fluorescein, allowing a fluorimetric read-out. 20 μl per well of 500 μM FDG/2.5% Triton X100 was added (the detergent was necessary to render the cells permeable). After incubation of the cells with the substrate for 60 min, 20 μl per well of 1M sodium carbonate was added to terminate the reaction and enhance the fluorescent signal. The plates were then read in a fluorimeter at 485/535 nm.

The compounds of the invention give an increase in fluorescent signal of at least ~1.5-fold that of the background signal (i.e. the signal obtained in the presence of 1% DMSO without compound).
cAMP Assay A stable cell line expressing recombinant human GPR116 was established and this cell line was used to investigate the effect of compounds of the invention on intracellular levels of cyclic AMP (cAMP). The cells monolayers were washed with phosphate buffered saline and stimulated at 37° C. for 30 min with various concentrations of compound in stimulation buffer plus 1% DMSO. Cells were then lysed and cAMP content determined using the Perkin Elmer AlphaScreen™ (Amplified Luminescent Proximity Homogeneous Assay) cAMP kit. Buffers and assay conditions were as described in the manufacturer's protocol. Compounds of the invention showed a concentration-dependant increase in intracellular cAMP level and generally had an EC$_{50}$ of <10 μM.
In vivo Feeding Study The effect of compounds of the invention on body weight and food and water intake was examined in freely-feeding male Sprague-Dawley rats maintained on reverse-phase Lighting. Test compounds and reference compounds were dosed by appropriate routes of administration (e.g. intraperitoneally or orally) and measurements made over the following 24 h. Rats were individually housed in polypropylene cages with metal grid floors at a temperature of 21±4° C. and 55±20% humidity. Polypropylene trays with cage pads were placed beneath each cage to detect any food spillage. Animals were maintained on a reverse phase light-dark cycle (lights off for 8 h from 09.30-17.30 h) during which time the room was illuminated by red light. Animals had free access to a standard powdered rat diet and tap water during a two week acclimatization period. The diet was contained in glass feeding jars with aluminum lids. Each lid had a 3-4 cm hole in it to allow access to the food. Animals, feeding jars and water bottles were weighed (to the nearest 0.1 g) at the onset of the dark period. The feeding jars and water bottles were subsequently measured 1, 2, 4, 6 and 24 h after animals were dosed with a compound of the invention and any significant differences between the treatment groups at baseline compared to vehicle-treated controls.

Selected compounds of the invention showed a statistically significant hyperphagic effect at one or more time points at a dose of <100 mg/kg.

What is claimed is:

1. A compound of formula (I), or a pharmaceutically acceptable salt thereof:

$$R^1\text{-V-B}\text{—}R^2 \qquad (I)$$

wherein V represents a 5-membered heteroaryl ring of the formula:

wherein W is N and one of X and Y is N and the other is O;
B is —CH═CH— or $(CH_2)_n$, where one of the $CH_2$ groups may be replaced by O, $NR^5$, $S(O)_m$, $C(O)$ or $C(O)NR^{12}$;
n is 2 or 3;
m is 0, 1 or 2;
$R^1$ is 4-pyridyl optionally substituted by 1 or 2 halo, $C_{1-4}$ alkyl, $C_{1-4}$ fluoroalkyl, $C_{2-4}$ alkenyl, $C_{2-4}$ alkynyl, $C_{3-7}$ cycloalkyl, aryl, $OR^6$, CN, $NO_2$, $S(O)_mR^6$, $CON(R^6)_2$, $N(R^6)_2$, $NR^{10}COR^6$, $NR^{10}SO_2R^6$, $SO_2N(R^6)_2$, 4- to 7-membered heterocyclyl or 5- or 6-membered heteroaryl groups;
$R^2$ is 4- to 7-membered cycloalkyl substituted by $R^3$, $C(O)OR^3$, $C(O)R^3$ or $S(O)_2R^3$, or $R^2$ is 4- to 7-membered heterocyclyl, wherein the heterocycle contains one nitrogen atom which is substituted by $C(O)OR^4$, $C(O)R^3$, $S(O)_2R^3$, $C(O)NHR^4$, $P(O)(OR^{11})_2$ or a 5- or 6-membered nitrogen containing heteroaryl group;
$R^3$ is $C_{3-8}$ alkyl, $C_{3-8}$ alkenyl or $C_{3-8}$ alkynyl, any of which may be optionally substituted with up to 5 fluoro or chloro atoms, and may contain a $CH_2$ group that may be replaced by O, or $C_{3-7}$ cycloalkyl, aryl, heterocyclyl, heteroaryl, $C_{1-4}$ alkyl$C_{3-7}$ cycloalkyl, $C_{1-4}$ alkylaryl, $C_{1-4}$ alkylheterocyclyl or $C_{1-4}$ alkylheteroaryl, any of which may be optionally substituted with one or more substituents selected from halo, $C_{1-4}$ alkyl, $C_{1-4}$ fluoroalkyl, $OR^6$, CN, $CO_2C_{1-4}$ alkyl, $N(R^6)_2$ and $NO_2$;
$R^4$ is $C_{2-8}$ alkyl, $C_{2-8}$ alkenyl or $C_{2-8}$ alkynyl, any of which may be optionally substituted with up to 5 fluoro or chloro atoms, and may contain a $CH_2$ group that may be replaced by O, or $C_{3-7}$ cycloalkyl, aryl, heterocyclyl, heteroaryl, $C_{1-4}$ alkyl$C_{3-7}$ cycloalkyl, $C_{1-4}$ alkylaryl, $C_{1-4}$ alkylheterocyclyl or $C_{1-4}$ alkylheteroaryl, any of which may be substituted with one or more substituents selected from halo, $C_{1-4}$ alkyl, $C_{1-4}$ fluoroalkyl, $OR^6$, CN, $CO_2C_{1-4}$ alkyl, $N(R^6)_2$ and $NO_2$;
$R^5$ is hydrogen, $C(O)R^7$, $S(O)_2R^8$, $C_{3-7}$ cycloalkyl or $C_{1-4}$ alkyl optionally substituted by $OR^6$, $C_{3-7}$ cycloalkyl aryl, heterocyclyl or heteroaryl, wherein the cyclic groups may be substituted with one or more substituents selected from halo, $C_{1-2}$ alkyl $C_{1-2}$ fluoroalkyl, $OR^6$, CN, $N(R^6)_2$ and $NO_2$;
$R^6$ are independently hydrogen $C_{1-4}$ alkyl, $C_{3-7}$ cycloalkyl, aryl, heterocyclyl or heteroaryl, wherein the cyclic groups may be substituted with one or more substituents selected from halo, $C_{1-4}$ alkyl $C_{1-4}$ fluoroalkyl, $OR^9$, CN, $SO_2CH_3$, $N(R^{10})_2$ and $NO_2$; or a group $N(R^{10})_2$ may form a 4- to 7-membered heterocyclic ring optionally containing a further heteroatom selected from O and $NR^{10}$;
$R^7$ is hydrogen, $C_{1-4}$ alkyl, $OR^6$, $N(R^6)_2$, aryl or heteroaryl;
$R^8$ is $C_{1-4}$ alkyl, $C_{1-4}$ fluoroalkyl, aryl or heteroaryl;
$R^9$ is hydrogen, $C_{1-2}$ alkyl or $C_{1-2}$ fluoroalkyl;
$R^{10}$ is hydrogen or $C_{1-4}$ alkyl;
$R^{11}$ is phenyl; and
$R^{12}$ is hydrogen, $C_{1-4}$ alkyl or $C_{3-7}$ cycloalkyl.

2. A compound according to claim 1, or a pharmaceutically acceptable salt thereof; wherein $R^1$ is 4-pyridyl optionally substituted by halo, $C_{1-4}$ alkyl $C_{1-4}$ alkoxy or CN.

3. A compound according to claim 1, or a pharmaceutically acceptable salt thereof, wherein $R^2$ is a 4- to 7-membered cycloalkyl substituted by $R^3$, or 4- to 7-membered heterocyclyl containing one nitrogen atom which is substituted by $C(O)OR^4$.

4. A compound according to claim 1, or a pharmaceutically acceptable salt thereof, wherein $R^3$ is $C_{3-8}$ alkyl which may contain a $CH_2$ group that may be replaced by O, or $C_{3-7}$ cycloalkyl.

5. A compound according to claim 1, or a pharmaceutically acceptable salt thereof, wherein $R^4$ is $C_{2-8}$ alkyl, $C_{2-8}$ alkenyl or $C_{2-8}$ alkynyl, any of which may be optionally substituted with up to 5 fluoro or chloro atoms, and may contain a $CH_2$ group that may be replaced by O, or $C_{3-7}$ cycloalkyl, aryl, 5- to 6-membered heteroaryl containing one or two nitrogen atoms, $C_{1-4}$ alkyl$C_{3-7}$ cycloalkyl or $C_{1-4}$ alkylaryl, any of which may be substituted with one or more substituents selected from halo, $C_{1-4}$ alkyl, $C_{1-4}$ fluoroalkyl, $OR^6$ and $CO_2C_{1-4}$ alkyl.

6. A compound according to claim 5, or a pharmaceutically acceptable salt thereof, wherein $R^4$ is $C_{3-6}$ alkyl optionally substituted with up to 5 fluoro or chloro atoms, and which may contain a $CH_2$ group that may be replaced by O, or $C_{3-7}$ cycloalkyl.

7. A compound according to claim 1, or a pharmaceutically acceptable salt thereof, wherein $R^5$ is $C_{1-4}$ alkyl.

8. A compound selected from
4-(3-Pyridin-4-yl-[1,2,4]oxadiazol-5-ylmethoxy)piperidine-1-carboxylic acid tert-butyl ester;
3-(3-Pyridin-4-yl-[1,2,4]oxadiazol-5-ylmethoxy)piperidine-1-carboxylic acid tert-butyl ester;
4-[5-(4-Pentylcyclohexylmethyl)-[1,2,4]oxadiazol-3-yl] pyridine;
trans-2-Chloro-4-[5-(4-pentylcyclohexane)[1,2,4]oxadiazol-3-yl]pyridine;
4-[5-(4-n-Propylcyclohexyl)-[1,2,4]oxadiazol-3-yl]pyridine;
trans-4-[5-(4-Pentylcyclohexane)-[1,2,4]oxadiazol-3-yl] pyridine ;
4-[2-(3-Pyridin-4-yl-[1,2,4]oxadiazol-5-yl)-ethyl]piperidine-1-carboxylic acid tert-butyl ester;
4-(3-Pyridin-4-yl-[1,2,4]oxadiazol-5-ylmethyl)piperidine-1-carboxylic acid tert-butyl ester;
trans-4-[3-(4-Pentylcyclohexyl)-[1,2,4]oxadiazol-5-yl] pyridine-2-carboxylic acid methylamide;
trans-4-[5-(4-Pentylcyclohexyl)-[1,2,4]oxadiazol-3-yl] pyridine-2-carboxylic acid amide;
trans-4-[3-(4-Pentylcyclohexyl)-[1,2,4]oxadiazol-5-yl] pyridine;

trans-2-Chloro-4-[3-(4-pentylcyclohexyl)-[1,2,4]oxadiazol-5-yl]pyridine;
trans-3-[3-(4-Pentylcyclohexyl)-[1,2,4]oxadiazol-5-yl]pyridine;
trans-2-Methyl-3-[3-(4-pentylcyclohexyl)-[1,2,4]oxadiazol-5-yl]pyridine;
trans-2-Chloro-6-methyl-4-[3-(4-pentylcyclohexyl)-[1,2,4]oxadiazol-5-yl]pyridine;
trans-4-[3-(4-Pentylcyclohexyl)-[1,2,4]oxadiazol-5-yl]pyridine-2-carbonitrile;
trans-2-Chloro-3[3-(4-pentylcyclohexyl)-[1,2,4]oxadiazol-5-yl]pyridine;
trans-2-Chloro-6-methyl-3-[3-(4-pentylcyclohexyl)-[1,2,4]oxadiazol-5-yl]pyridine;
trans-2-Methyl-5-[3-(4-pentylcyclohexyl)-[1,2,4]oxadiazol-5-yl]pyridine;
trans-3-Methyl-5-[3-(4-pentylcyclohexyl)-[1,2,4]oxadiazol-5-yl]pyridine;
trans-2,6-Dichloro-4-[3-(4-pentylcyclohexyl)[1,2,4]oxadiazol-5-yl]pyridine;
trans-2-Chloro-6-methoxy-4-[3-(4-pentylcyclohexyl)-[1,2,4]oxadiazol-5-yl]pyridine;
trans-5-[3-(4-Pentylcyclohexyl)[1,2,4]oxadiazol-5-yl]-[1,2,4]triazol-1-ylpyridine;
2-[3-(4-Pentylcyclohexyl)-[1,2,4]oxadiazol-5-yl]pyrazine;
4-[3-(4-Pentylcyclohexyl)-[1,2,4]oxadiazol-5-yl]pyrimidine;
trans-5-[3-(4-Pentylcyclohexyl)-[1,2,4]oxadiazol-5-yl]pyridine-2-carbonitrile;
trans-5-Chloro-2-methylsulfanyl-4-[3-(4-pentylcyclohexyl)-[1,2,4]oxadiazol-5-yl]pyrimidine;
trans-2-Fluoro-5-[3-(4-pentylcyclohexyl)[1,2,4]oxadiazol-5-yl]pyridine;
trans-2-Fluoro-4-[3-(4-pentylcyclohexyl)-[1,2,4]oxadiazol-5-yl]pyridine;
trans-2-Imidazol-1-yl-5-[3-(4-pentylcyclohexyl)-[1,2,4]oxadiazol-5-yl]pyridine;
trans-2-Methyl-4-[3-(4-pentylcyclohexyl)-[1,2,4]oxadiazol-5-yl]pyridine;
trans-3-Methyl-4-[3-(4-pentylcyclohexyl)-[1,2,4]oxadiazol-5-yl]pyridine;
4-(5-Pyridin-4-yl-[1,2,4]oxadiazol-3-ylmethoxy)piperidine-1-carboxylic acid tert-butyl ester;
4-[5-(2-Cyanopyridin-4-yl)-[1,2,4]oxadiazol-3-ylmethoxy]piperidine-1-carboxylic acid tert-butyl ester;
4-(3-Pyridin-4-yl-[1,2,4]oxadiazol-5-yl)piperidine-1-carboxylic acid isobutyl ester;
4-(3-Pyridin-4-yl-[1,2,4]oxadiazol-5-yl)piperidine-1-carboxylic acid 2-methoxyethyl ester;
4-(3-Pyridin-4-yl-[1,2,4]oxadiazol-5-yl)piperidine-1-carboxylic acid ethyl ester;
3,3-Dimethyl-1-[4-(3-pyridin-4-yl-[1,2,4]oxadiazol-5-yl)piperidin-1-yl]butan-1-one;
2-Cyclopentyl-1-[4-(3-pyridin-4-yl-[1,2,4]oxadiazol-5-yl)piperidin-1-yl]ethanone;
4- {5-[1-(Butane- 1-sulfonyl)piperidin-4-yl]-[1,2,4]oxadiazol-3-yl}pyridine;
4-(3-Pyridin-4-yl-[1,2,4]oxadiazol-5-yl)piperidine-1-carboxylic acid propylamide;
4-(3-Pyridin-4-yl-[1,2,4]oxadiazol-5-yl)piperidine-1-carboxylic acid tert-butylamide;
4-(3-Pyridin-4-yl-[1,2,4]oxadiazol-5-ylmethoxy)piperidine-1-carboxylic acid cyclopentyl ester;
4-(3-Pyridin-4-yl-[1,2,4]oxadiazol-5-ylmethoxy)piperidine-1-carboxylic acid benzyl ester;
4-(3-Pyridin-4-yl-[1,2,4]oxadiazol-5-ylmethoxy)piperidine-1-carboxylic acid isobutyl ester;
4-(3-Pyridin-4-yl-[1,2,4]oxadiazol-5-ylmethoxy)piperidine-1-carboxylic acid ethyl ester;
4-(3-Pyridin-4-yl-[1,2,4]oxadiazol-5-ylmethoxy)piperidine-1-carboxylic acid cycloheptyl ester;
4-(3-Pyridin-4-yl-[1,2,4]oxadiazol-5-ylmethoxy)piperidine-1-carboxylic acid methyl ester;
4-(3-Pyridin-4-yl-[1,2,4]oxadiazol-5-ylmethoxy)piperidine-1-carboxylic acid 2-methoxy-ethyl ester;
4-(3-Pyridin-4-yl-[1,2,4]oxadiazol-5-ylmethoxy)piperidine-1-carboxylic acid isopropyl ester;
4-(3-Pyridin-4-yl-[1,2,4]oxadiazol-5-ylmethoxy)piperidine-1-carboxylic acid 4-methoxy-phenyl ester;
4-(3-Pyridin-4-yl-[1,2,4]oxadiazol-5-ylmethoxy)piperidine-1-carboxylic acid 2,2,2-trichloroethyl ester;
4-(3-Pyridin-4-yl-[1,2,4]oxadiazol-5-ylmethoxy)piperidine-1-carboxylic acid 4-chloro-phenyl ester;
4-(3-Pyridin-4-yl-[1,2,4]oxadiazol-5-ylmethoxy)piperidine-1-carboxylic acid phenyl ester;
4-(3-Pyridin-4-yl-[1,2,4]oxadiazol-5-ylmethoxy)piperidine-1-carboxylic acid 2-ethyl-hexyl ester;
4-(3-Pyridin-4-yl-[1,2,4]oxadiazol-5-ylmethoxy)piperidine-1-carboxylic acid propyl ester;
4-(3-Pyridin-4-yl-[1,2,4]oxadiazol-5-ylmethoxy)piperidine-1-carboxylic acid hexyl ester;
4-(3-Pyridin-4-yl-[1,2,4]oxadiazol-5-ylmethoxy)piperidine-1-carboxylic acid (1R,2S,5R)-2-isopropyl-5-methylcyclohexyl ester;
4-(3-Pyridin-4-yl-[1,2,4]oxadiazol-5-ylmethoxy)piperidine-1-carboxylic acid (1S,2R,5S)-2-isopropyl-5-methylcyclohexyl ester;
4-(3-Pyridin-4-yl-[1,2,4]oxadiazol-5-ylmethoxy piperidine-1-carboxylic acid 2,2-dimethylpropyl ester;
4-(3-Pyridin-4-yl-[1,2,4]oxadiazol-5-ylmethoxy)piperidine-1-carboxylic acid naphthalen-1-yl ester;
4-(3-Pyridin-4-yl-[1,2,4]oxadiazol-5-ylmethoxy)piperidine-1-carboxylic acid 2-methoxy-phenyl ester;
4-(3-Pyridin-4-yl-[1,2,4]oxadiazol-5-ylmethoxy)piperidine-1-carboxylic acid 3-trifluoromethylphenyl ester;
4-(3-Pyridin-4-yl-[1,2,4]oxadiazol-5-ylmethoxy)piperidine-1-carboxylic acid prop-2-ynyl ester;
4-(3-Pyridin-4-yl-[1,2,4]oxadiazol-5-ylmethoxy)piperidine-1-carboxylic acid but-2-ynyl ester;
4-(3-Pyridin-4-yl-[1,2,4]oxadiazol-5-ylmethoxy)piperidine-1-carboxylic acid pentyl ester;
4-(3-Pyridin-4-yl-[1,2,4]oxadiazol-5-ylmethoxy)piperidine-1-carboxylic acid p-tolyl ester;
4-(3-Pyridin-4-yl-[1,2,4]oxadiazol-5-ylmethoxy)piperidine-1-carboxylic acid 2-chloro-phenyl ester;
4-(3-Pyridin-4-yl-[1,2,4]oxadiazol-5-ylmethoxy)piperidine-1-carboxylic acid naphthalen-2-yl ester;
4-(3-Pyridin-4-yl-[1,2,4]oxadiazol-5-ylmethoxy)piperidine-1-carboxylic acid butyl ester;
4-(3-Pyridin-4-yl-[1,2,4]oxadiazol-5-ylmethoxy)piperidine-1-carboxylic acid 4-methoxycarbonyl-phenyl ester;
4-(3-Pyridin-4-yl-[1,2,4]oxadiazol-5-ylmethoxy)piperidine-1-carboxylic acid 4-fluoro-phenyl ester;
3-Methyl- 1-[4-(3-pyridin-4-yl-[1,2,4]oxadiazol-5-ylmethoxy)piperidin- 1-yl]-butan-1-one;
Phenyl[4-(3-pyridin-4-yl-[1,2,4]oxadiazol-5-ylmethoxy)piperidin-1-yl]methanone;
1-[4-(3-Pyridin-4-yl-[1,2,4]oxadiazol-5-ylmethoxy)piperidin-1-yl]butan-1-one;
2,2-Dimethyl-1-[4-(3-pyridin-4-yl-[1,2,4]oxadiazol-5-ylmethoxy)piperidin-1-yl]propan-1-one;

Cyclopentyl-[4-(3-pyridin-4-yl-[1,2,4]oxadiazol-5-yl-methoxy)piperidin-1-yl]methanone;
[4-(3-Pyridin-4-yl-[1,2,4]oxadiazol-5-ylmethoxy)piperidin-1-yl]-p-tolylmethanone;
3,3-Dimethyl-1-[4-(3-pyridin-4-yl-[1,2,4]oxadiazol-5-ylmethoxy)piperidin-1-yl]butan-1-one;
4- {5-[1-(Butane- 1-sulfonyl) piperidin-4-yloxymethyl]-[1,2,4]oxadiazol-3-yl}pyridine;
4-{5[1-(Propane-1-sulfonyl) piperidin-4-yloxymethyl]-[1,2,4]oxadiazol-3-yl}pyridine;
4-(3-Pyridin-4-yl-[1,2,4]oxadiazol-5-ylmethoxy)piperidine-1-carboxylic acid tert-butylamide;
4-(3-Pyridin-4-yl-[1,2,4]oxadiazol-5-ylmethoxy)piperidine-1-carboxylic acid o-tolylamide;
trans-4-(3-Pyridin-4-yl-[1,2,4]oxadiazol-5-yl)cyclohexanecarboxylic acid propyl ester;
trans-4-(3-Pyridin-4-yl-[1,2,4]oxadiazol-5-yl)cyclohexanecarboxylic acid butyl ester;
trans-4-(3-Pyridin-4-yl-[1,2,4]oxadiazol-5-yncyclohexanecarboxylic acid isobutyl ester;
trans-4-[5-(4-Propoxymethylcyclohexyl)-[1,2,4]oxadiazol-3-yl]pyridine;
trans-4-[5-(4-Butoxymethylcyclohexyl)-[1,2,4]oxadiazol-3-yl]pyridine;
cis-4-[5-(3-Butoxymethylcyclopentyl)-[1,2,4]oxadiazol-3-yl]pyridine;
cis-4-[5-(3-Propoxymethylcyclopentyl)-[1,2,4]oxadiazol-3-yl]pyridine;
cis-4-[5-(3-Butoxymethylcyclohexyl)-[1,2,4]oxadiazol-3-yl]pyridine;
4-(3-Pyridin-4-yl-[1,2,4]oxadiazol-5-ylmethoxy)-3,4,5,6-tetrahydro-2H[1,3']bipyridinyl;
2-[4-(3-Pyridin-4-yl-[1,2,4]oxadiazol-5-ylmethoxy)piperidin-1-yl]pyrazine;
2-[4-(3-Pyridin-4-yl-[1,2,4]oxadiazol-5-ylmethoxy)piperidin-1-yl]pyrimidine;
(4-Pentylcyclohexyl)-(3-pyridin-4-yl-[1,2,4]oxadiazol-5-ylmethyl)amine;
(4-Pentylcyclohexyl-methyl)-(3-pyridin-4-yl-[1,2,4]oxadiazol-5-ylmethyl)amine;
4-[(3-Pyridin-4-yl-[1,2,4]oxadiazol-5-ylmethyl)amino]piperidine-1-carboxylic acid tert-butyl ester;
4-{[(3-Pyridin-4-yl-[1,2,4]oxadiazol-5-ylmethyl)amino]methyl}-piperidine-1-carboxylic acid tert-butyl ester;
4-{[5-(2-Cyanopyridin-4-yl)[1,2,4]oxadiazol-3-ylmethyl]amino}-piperidine-1-carboxylic acid tert-butyl ester;
Methyl-(4-pentylcyclohexyl)-(3-pyridin-4-yl-[1,2,4]oxadiazol-5-ylmethyl)amine;
Methyl-(4-pentylcyclohexylmethyl)-(3-pyridin-4-yl-[1,2,4]oxadiazol-5-ylmethyl)amine;
4-[Methyl-(3-pyridin-4-yl-[1,2,4]oxadiazol-5-ylmethyl)amino]piperidine-1-carboxylic acid tert-butyl ester:
4-[Ethyl-(3-pyridin-4-yl-[1,2,4]oxadiazol-5-ylmethyl)amino]piperidine-1-carboxylic acid tert-butyl ester;
4-[Propyl-(3-pyridin-4-yl-[1,2,4]oxadiazol-5-ylmethyl)amino]piperidine-1-carboxylic acid tert-butyl ester;
4-[Cyclopropylmethyl-(3-pyridin-4-yl-[1,2,4]oxadiazol-5-ylmethyl)amino]piperidine-1-carboxylic acid tert-butyl ester;
4-[Butyl-(3-pyridin-4-yl-[1,2,4]oxadiazol-5-ylmethyl)amino]piperidine-1-carboxylic acid tert-butyl ester;
4-{[Methyl-(3-pyridin-4-yl-[1,2,4]oxadiazol-5-ylmethyl)amino]methyl}-piperidine-1-carboxylic acid tert-butyl ester;
4-{[Ethyl-(3-pyridin-4-yl-[1,2,4]oxadiazol-5-ylmethyl)amino]methyl}-piperidine-1-carboxylic acid tert-butyl ester;
4-{[5-(2-Cyanopyridin-4-yl)-[1,2,4]oxadiazol-3-ylmethyl]ethylamino}-piperidine-1-carboxylic acid tert-butyl ester;
4-[Methyl-(3-pyridin-4-yl-[1,2,4]oxadiazol-5-ylmethyl)amino]piperidine-1-carboxylic acid cyclopentyl ester;
4-[Methyl-(3-pyridin-4-yl-[1,2,4]oxadiazol-5-ylmethyl)amino]piperidine-1-carboxylic acid cyclopentyl ester;
4-(3-Pyridin-4-yl-[1,2,4]oxadiazol-5-ylmethoxymethyl) piperidine-1-carboxylic acid tert-butyl ester;
4-(3-Pyridin-4-yl-[1,2,4]oxadiazol-5-ylmethyl)piperazine-1-carboxylic acid tert-butyl ester;
4-(3-Pyridin-4-yl-[1,2,4]oxadiazol-5-ylmethylsulfanyl) piperidine-1-carboxylic acid tert-butyl ester;
4-(3-Pyridin-4-yl-[1,2,4]oxadiazol-5-ylmethanesulfonyl) piperidine-1-carboxylic acid tert-butyl ester
3-Pyridin-4-yl-[1,2,4]oxadiazole-5-carboxylic acid (4-pentylcyclohexyl)amide;
[4-(3-Pyridin-4-yl-[1,2,4]oxadiazol-5-ylmethoxy)piperidin-1-yl]phosphonic acid diphenyl ester;
4-{5-[2(2H-Tetrazol-5-yl)pyridin-4-yl]-[1,2,4]oxadiazol-3-ylmethoxy}-piperidine-1-carboxylic acid tert-butyl ester;
4-[5-(2-Cyanopyridin-4-yl)-[1,2,4]oxadiazol-3-ylmethoxy]piperidine-1-carboxylic acid isopropyl ester; or
4-[5-(2-Cyanopyridin-4-yl)-[1,2,4]oxadiazol-3-ylmethoxy]piperidine-1-carboxylic acid phenyl ester;

and a pharmaceutically acceptable salt thereof.

9. A compound according to claim 1, or a pharmaceutically acceptable salt thereof, wherein B is —CH═CH— or $(CH_2)_n$, where one of the $CH_2$ groups may be replaced by O, $NR^5$, $S(O)_m$, or C(O);

n is 2 or 3;

m is 0, 1 or 2;

$R^2$ is 4- to 7-membered heterocyclyl containing one nitrogen atom which is substituted by $C(O)OR^4$ or a 6-membered nitrogen containing heteroaryl group;

$R^4$ is $C_{2-8}$ alkyl, $C_{2-8}$ alkenyl or $C_{2-8}$ alkynyl, any of which may be optionally substituted with up to 5 fluoro or chloro atoms, and may contain a $CH_2$ group that may be replaced by O, or $C_{3-7}$ cycloalkyl, aryl, heterocyclyl, heteroaryl, $C_{1-4}$ alkyl$C_{3-7}$ cycloalkyl, $C_{1-4}$ alkylaryl, $C_{1-4}$ alkylheterocyclyl or $C_{1-4}$ alkylheteroaryl, any of which may be substituted with one or more substituents selected from halo, $C_{1-4}$ alkyl, $C_{1-4}$ fluoroalkyl, $OR^6$, CN, $CO_2C_{1-4}$ alkyl, $N(R^6)_2$ and $NO_2$;

$R^5$ is hydrogen or $C_{1-4}$ alkyl;

$R^6$ are independently hydrogen, or $C_{1-4}$ alkyl, $C_{3-7}$ cycloalkyl, aryl, heterocyclyl or heteroaryl, wherein the cyclic groups may be substituted with one or more substituents selected from halo, $C_{1-4}$ alkyl, $C_{1-4}$ fluoroalkyl, $OR^9$, CN, $SO_2CH_3$, $N(R^{10})_2$ and $NO_2$; or a group $N(R^{10})_2$ may form a 4- to 7-membered heterocyclic ring optionally containing a further heteroatom selected from O and $NR^{10}$;

$R^9$ is hydrogen, $C_{1-2}$ alkyl or $C_{1-2}$ fluoroalkyl; and $R^{10}$ is hydrogen or $C_{1-4}$ alkyl.

10. A compound having the formula (Ie), or a pharmaceutically acceptable salt thereof:

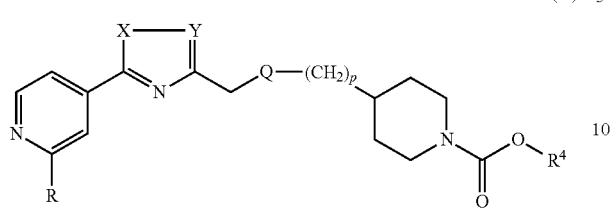

wherein one of X and Y is N, and the other is O;
Q is O, $NR^5$ or $CH_2$;
R is hydrogen, halo, $C_{1-4}$ alkyl, $C_{1-4}$ fluoroalkyl, $C_{2-4}$ alkenyl, $C_{2-4}$ alkynyl, $C_{3-7}$ cycloalkyl, aryl, $OR^6$, CN, $NO_2$, $S(O)_m R^6$, $CON(R^6)_2$, $N(R^6)_2$, $NR^{10}COR^6$, $NR^{10}SO_2 R^6$, $SO_2 N(R^6)_2$, a 4- to 7-membered heterocyclyl group or a 5- or 6-membered heteroaryl group;
$R^4$ is $C_{2-8}$ alkyl, $C_{2-8}$ alkenyl or $C_{2-8}$ alkynyl, any of which may be optionally substituted with up to 5 fluoro or chloro atoms, and contain a $CH_2$ group that may be replaced by O, or $C_{3-7}$ cycloalkyl, aryl, heterocyclyl, heteroaryl, $C_{1-4}$ alkyl$C_{3-7}$ cycloalkyl, $C_{1-4}$ alkylaryl, $C_{1-4}$ alkylheterocyclyl or $C_{1-4}$ alkylheteroaryl, any of which may be substituted with one or more substituents selected from halo, $C_{1-4}$ alkyl, $C_{1-4}$ fluoroalkyl, $OR^6$, CN, $CO_2 C_{1-4}$ alkyl, $N(R^6)_2$ and $NO_2$;
$R^5$ is $C_{1-4}$ alkyl;
$R^6$ are independently hydrogen, or $C_{1-4}$ alkyl, $C_{3-7}$ cycloalkyl, aryl, heterocyclyl or heteroaryl, wherein the cyclic groups may be substituted with one or more substituents selected from halo, $C_{1-4}$ alkyl, $C_{1-4}$ fluoroalkyl, $OR^9$, CN, $SO_2 CH_3$, $N(R^{10})_2$ and $NO_2$; or a group $N(R^{10})_2$ may form a 4- to 7-membered heterocyclic ring optionally containing a further heteroatom selected from O and $NR^{10}$;
$R^9$ is hydrogen, $C_{1-2}$ alkyl or $C_{1-2}$ fluoroalkyl;
$R^{10}$ is hydrogen or $C_{1-4}$ alkyl; and
p is 0 or 1.

11. A pharmaceutical composition comprising a compound according to claim 1, or a pharmaceutically acceptable salt thereof; and a pharmaceutically acceptable carrier.

* * * * *

UNITED STATES PATENT AND TRADEMARK OFFICE
CERTIFICATE OF CORRECTION

PATENT NO. : 8,207,147 B2  Page 1 of 1
APPLICATION NO. : 10/584025
DATED : June 26, 2012
INVENTOR(S) : Fyfe et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 998 days.

Signed and Sealed this
Twenty-third Day of October, 2012

David J. Kappos
*Director of the United States Patent and Trademark Office*